United States Patent
Shinohata et al.

(10) Patent No.: US 9,637,445 B2
(45) Date of Patent: May 2, 2017

(54) ISOCYANATE PRODUCTION PROCESS USING COMPOSITION CONTAINING CARBAMIC ACID ESTER AND AROMATIC HYDROXY COMPOUND, AND COMPOSITION FOR TRANSFER AND STORAGE OF CARBAMIC ACID ESTER

(71) Applicant: Asahi Kasei Chemicals Corporation, Tokyo (JP)

(72) Inventors: Masaaki Shinohata, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 14/705,545

(22) Filed: May 6, 2015

(65) Prior Publication Data

US 2015/0259279 A1 Sep. 17, 2015

Related U.S. Application Data

(62) Division of application No. 12/593,805, filed as application No. PCT/JP2008/055772 on Mar. 26, 2008, now Pat. No. 9,056,819.

(30) Foreign Application Priority Data

Mar. 30, 2007 (JP) ................................ 2007-091073

(51) Int. Cl.
| | | |
|---|---|---|
| *C07C 271/28* | (2006.01) | |
| *C07C 263/04* | (2006.01) | |
| *C07C 269/08* | (2006.01) | |
| *C07C 271/20* | (2006.01) | |
| *C07C 271/24* | (2006.01) | |

(52) U.S. Cl.
CPC .......... *C07C 271/28* (2013.01); *C07C 263/04* (2013.01); *C07C 269/08* (2013.01); *C07C 271/20* (2013.01); *C07C 271/24* (2013.01)

(58) Field of Classification Search
None
See application file for complete search history.

(56) References Cited

U.S. PATENT DOCUMENTS

| | | | |
|---|---|---|---|
| 2,692,275 A | 10/1954 | Bortnick | |
| 3,734,941 A | 5/1973 | Sydor | |
| 3,992,430 A | 11/1976 | Bacskai | |
| 4,081,472 A | 3/1978 | Tsumura et al. | |
| 4,290,970 A | 9/1981 | Merger et al. | |
| 4,307,029 A | 12/1981 | Takeuchi et al. | |
| 4,354,979 A | 10/1982 | Schwendemann et al. | |
| 4,381,405 A | 4/1983 | Takeuchi et al. | |
| 4,386,033 A | 5/1983 | Konig et al. | |
| 4,388,238 A | 6/1983 | Heitkamper et al. | |
| 4,388,246 A | 6/1983 | Sundermann et al. | |
| 4,388,426 A | 6/1983 | Schure et al. | |
| 4,395,565 A | 7/1983 | Romano et al. | |
| 4,430,505 A | 2/1984 | Heitkamper et al. | |
| 4,480,110 A | 10/1984 | Heitkamper et al. | |
| 4,482,499 A | 11/1984 | Merger et al. | |
| 4,497,963 A | 2/1985 | Merger et al. | |
| 4,514,339 A | 4/1985 | Romano et al. | |
| 4,596,678 A | 6/1986 | Merger et al. | |
| 4,596,679 A | 6/1986 | Hellbach et al. | |
| 4,613,466 A | 9/1986 | Merger et al. | |
| 4,659,845 A | 4/1987 | Rivetti et al. | |
| 4,692,550 A | 9/1987 | Engbert et al. | |
| 5,043,471 A | 8/1991 | Hammen et al. | |
| 5,386,053 A | 1/1995 | Otterbach et al. | |
| 5,545,600 A | 8/1996 | Knudsen et al. | |
| 5,731,458 A | 3/1998 | Dahmer et al. | |
| 5,773,643 A | 6/1998 | Yagii et al. | |
| 7,435,842 B2 | 10/2008 | Miyake et al. | |
| 7,446,218 B2 | 11/2008 | Miyake et al. | |
| 2003/0055282 A1 | 3/2003 | Bosman et al. | |
| 2008/0275262 A1 | 11/2008 | Miyake et al. | |

FOREIGN PATENT DOCUMENTS

| | | |
|---|---|---|
| CA | 2015223 A1 | 11/1990 |
| CA | 2209754 A1 | 1/1998 |
| EP | 125726 A1 | 11/1984 |

(Continued)

OTHER PUBLICATIONS

English Translation of Takeuchi et al., JP 59062561, 1984.*
Printout of https://en.wikipedia.org/wiki/Boiling_point (downloaded on Mar. 31, 2016).*
Melting and boiling point tables, Carnelley, 1885, vol. 1, London, Harrison.*
Melting and boiling point tables, Carnelley, 1885, vol. 2, London, Harrison.*
Search Report issued in related European Patent Application No. 08722869.8 dated Jul. 11, 2013.
Berchte der Deutechen Chemischen Gesellschaft, 3: 653 (1970).
Combined Chemical Dictionary 9, 357, Kyoritsu Shuppan Co., Ltd., Japan 2003.
Dyer et al., "Thermal degradation of alkyl N-phenylcarbamates," Journal of the American Chemical Society, 81: 2138-2143 (1959).
International Preliminary Report on Patentability issued in related International Patent Application No. PCT/JP2008/055772 dated Sep. 30, 2009.
Office Action issued in related Taiwanese Patent Application No. 097111525 dated Aug. 12, 2011.

*Primary Examiner* — Sudhakar Katakam
*Assistant Examiner* — Jennifer C Sawyer
(74) *Attorney, Agent, or Firm* — Morgan, Lewis & Bockius LLP

(57) ABSTRACT

An object of the present invention is to provide an isocyanate production process, which is free of the various problems found in the prior art, and which uses a composition containing a carbamic acid ester and an aromatic hydroxy compound when producing isocyanate without using phosgene, as well as a carbamic acid ester composition for transferring or storing carbamic acid ester. The present invention discloses an isocyanate production process including specific steps and using a composition containing a carbamic acid ester and an aromatic hydroxy compound, as well as a composition for transfer or storage of carbamic acid ester comprising the carbamic acid ester and the specific aromatic hydroxy compound.

1 Claim, 8 Drawing Sheets

(56) References Cited

FOREIGN PATENT DOCUMENTS

| | | |
|---|---|---|
| EP | 0320235 A2 | 6/1989 |
| EP | 0355443 A2 | 2/1990 |
| EP | 0396976 A2 | 11/1990 |
| EP | 0396977 A2 | 11/1990 |
| EP | 0611243 A1 | 8/1994 |
| EP | 1323708 A1 | 7/2003 |
| EP | 1640357 A1 | 3/2006 |
| JP | S56-065858 A | 6/1981 |
| JP | S57-159752 A | 10/1982 |
| JP | S59-048452 A | 3/1984 |
| JP | 59062561 * | 4/1984 |
| JP | S64-085956 A | 3/1989 |
| JP | H06-172292 A | 6/1994 |
| JP | H07-165696 A | 6/1995 |
| JP | H09-087239 A | 3/1997 |
| JP | H09-249633 A | 9/1997 |
| JP | H10-087598 A | 4/1998 |
| JP | 2001-031629 A | 2/2001 |
| JP | 2001-048839 A | 2/2001 |
| JP | 2001-247519 A | 9/2001 |
| JP | 3382289 B2 | 12/2002 |
| JP | 2003-525267 A | 8/2003 |
| JP | 2004-244349 A | 9/2004 |
| JP | 2004-262831 A | 9/2004 |
| WO | 98/54128 A1 | 12/1998 |
| WO | 03/055840 A1 | 7/2003 |
| WO | 2004/014840 A1 | 2/2004 |
| WO | 2005/111049 A1 | 11/2005 |
| WO | 2008/059953 A1 | 5/2008 |
| WO | 2008/084824 A1 | 7/2008 |

* cited by examiner

ISOCYANATE PRODUCTION PROCESS USING COMPOSITION CONTAINING CARBAMIC ACID ESTER AND AROMATIC HYDROXY COMPOUND, AND COMPOSITION FOR TRANSFER AND STORAGE OF CARBAMIC ACID ESTER

TECHNICAL FIELD

The present invention relates to a process for producing an isocyanate using a composition containing a carbamic acid ester and an aromatic hydroxy compound. Moreover, the present invention relates to a composition for transfer and storage of carbamic acid ester, containing such a composition.

BACKGROUND ART

Carbamic acid esters (urethanes) are compounds that are widely used in applications such as polyurethane foam, surface coatings, elastomers, paints and adhesives, and are industrially extremely useful. In addition, carbamic acid esters are also useful as raw materials for producing isocyanates without using phosgene.

Industrial production of isocyanates mainly uses a reaction between an amine compound and phosgene ("phosgene method"), and nearly the entire amount of isocyanates produced worldwide is produced using the phosgene method. However, the phosgene method has numerous problems.

Firstly, a large amount of phosgene is used as a raw material. Phosgene is an extremely highly toxic substance, its handling requires special precautions to prevent handlers from being exposed, and special measures are also required to detoxify waste.

Secondly, since a large amount of highly corrosive hydrogen chloride is produced as a by-product of the phosgene method, in addition to requiring a process for detoxifying this hydrogen chloride, since hydrolysable salts are frequently contained in the isocyanates produced, in the case of using isocyanates produced according to the phosgene method, there are cases in which they have a detrimental effect on the weather resistance and heat resistance of polyurethane products.

In consideration of these factors, there is a need for a process for producing isocyanate compounds that does not use phosgene. One process that has been proposed for the production of isocyanates without using phosgene involves thermal decomposition of carbamic acid ester. Isocyanates and hydroxy compounds have long been known to be obtained from thermal decomposition of carbamic acid esters (see, for example, Non-Patent Document 1: Berchte der Deutechen Chemischen Gesellschaft, Vol. 3, p. 653, 1870). The basis reaction thereof is indicated by the following formula:

$$R(NHCOOR')_x \rightarrow R(NCO)_x + xR'OH \quad (1)$$

(wherein R represents an organic residue having a valence of x, R' represents a monovalent organic residue, and x represents an integer of 1 or more).

In this manner, although carbamic acid esters are industrially useful compounds, since carbamic acid esters easily form hydrogen bonds between molecules from ester groups forming the carbamic acid ester, they frequently have a high melting point. Typically, in the case of using a substance industrially, operations such as those for transferring that substance or storing that substance in a storage tank for a fixed period of time are required. In the transfer of a carbamic acid ester having a high melting point, a solid carbamic acid ester, for example, is crushed or treated with a vehicle for processing into the pellets and the like prior to transfer, or the carbamic acid ester is liquefied prior to transfer by heating to a temperature higher than the melting point of the carbamic acid ester. However, in the case of transferring the solid carbamic ester that has been treated with the vehicle for processing into the pellets, there is a need for a complex apparatus to ensure stable transfer of a fixed amount of carbamic acid ester or the need for a process for maintaining the form of the carbamic acid ester within a certain range in cases of the risk of clogging of the transfer line or frequent fluctuations in the form of the carbamic acid ester. On the other hand, in the case of transferring carbamic acid ester in the form of a liquid by heating, it is necessary to heat to a temperature higher than the melting point of the carbamic acid ester (for example, 200° C.) in consideration of preventing solidification during transfer. In the case of holding a carbamic acid ester under such high temperatures, undesirable side reactions may occur that cause a decrease in the yield of the carbamic acid ester. Examples of such side reactions may include the reactions of the following formulas (2) and (3) that occur due to isocyanate formed by the occurrence of a thermal decomposition reaction of carbamic acid ester as shown in formula (1) above, and the thermal denaturation reaction of carbamic acid ester as shown in the following formula (4) (see Non-Patent Document 1 and Non-Patent Document 2).

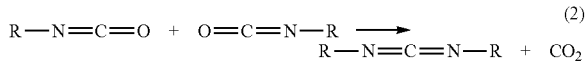

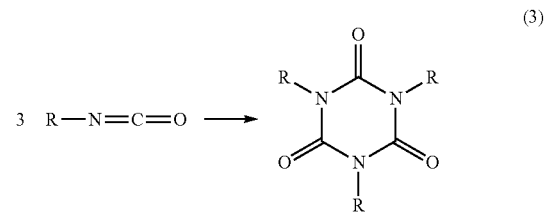

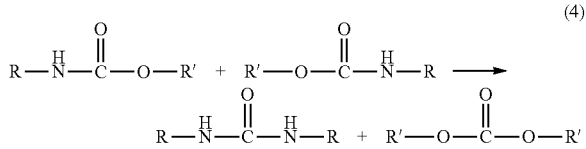

(wherein each of R and R' independently represents an organic group such as a aliphatic group or alicyclic group).

These side reactions not only lead to a decrease in the yield of carbamic acid ester, but in the case of handling carbamic acid esters in particular, there may also be precipitation of polymeric solids resulting in clogging of transfer lines or accumulation in storage tanks.

Several methods have been proposed to solve these problems.

Patent Document 1 discloses a method for storing or transporting aromatic urethane (carbamic acid ester equivalent to the product of a reaction between an aromatic isocyanate and a hydroxy compound) in the presence of an organic solvent. Although this method is characterized by the use of from 1 to 10 times the weight, based on the aromatic urethane, of an organic solvent that is inert with respect to the urethane and the isocyanate corresponding to that urethane, in this method, a decrease in the urethane cannot be inhibited, and a large amount of substances having unknown structures are produced.

In addition, Patent Document 2 discloses a method for storing an aromatic urethane solution by using 1,4-dioxane as a solvent for dissolving the urethane. However, in this method, since an equivalent amount (for example, 20 times the weight) of 1,4-dioxane must be used with respect to the urethane, this method had the problem of resulting in a decrease in the storage efficiency of the urethane.

In this manner, methods used to transfer or store carbamic acid esters without causing denaturation thereof still have problems remaining.

On the other hand, various processes have been proposed thus far for the production of carbamic acid esters.

According to the description of Patent Document 3, an aliphatic diurethane and/or alicyclic diurethane and/or aliphatic polyurethane and/or alicyclic polyurethane are obtained by reacting an aliphatic primary diamine and/or alicyclic primary diamine and/or aliphatic primary polyamine and/or alicyclic primary polyamine with O-alkylcarbamate in the presence of an alcohol and in the presence or absence of a catalyst at 160 to 300° C. at a ratio of amine $NH_2$ group: carbamate:alcohol of 1:0.8 to 10:0.25 to 50, followed by removing the ammonia formed as necessary.

In addition, according to Patent Document 4, an aryl diurethane and/or aryl polyurethane is produced by reacting an aromatic primary amine and/or aromatic primary polyamine with O-alkylcarbamate in the presence or absence of a catalyst and in the presence or absence of urea and alcohol to form an aryl diurethane and/or aryl polyurethane followed by removing the ammonia formed as necessary.

Other publications contain descriptions relating to partial substitution of urea and/or diamine by a carbonyl-containing compound such as N-substituted carbamate and/or dialkyl carbonate, or mono-substituted urea, di-substituted urea, mono-substituted polyurea or di-substituted polyurea (see Patent Document 5, Patent Document 6, Patent Document 7, Patent Document 8 and Patent Document 9). Patent Document 10 describes a process for producing aliphatic O-arylurethane by reacting a (cyclic) aliphatic polyamine with urea and an aromatic hydroxy compound.

In addition, according to Patent Document 11, a process is disclosed for producing a carbamic acid ester from an amine compound and dimethyl carbonate. This process reacts an amine compound and dimethyl carbonate in the presence of Lewis acid catalyst, lead, titanium, zirconium catalyst or alkaline catalyst and the like.

In this manner, although various methods are known for producing carbamic acid esters, at the time of using these carbamic acid ester, an operation is required for recovering the carbamic acid ester from a mixture containing the carbamic acid ester produced according to these methods. Several methods have been disclosed for recovering carbamic acid esters.

Patent Document 12 discloses a method distilling one or more types of diurethanes in the presence of a low boiling point alcohol having an alkyl group having 1 to 6 carbon atoms or an alicyclic hydrocarbon group having 5 or 6 carbon atoms. However, this method also had the problem of solid substances remaining in the distillation apparatus.

In addition, Patent Document 13 describes a method for distillative separation of an unreacted amine compound and alcohol from a reaction liquid obtained by reacting a carbonic acid ester and an amine compound. However, since a solution mainly containing carbamic acid ester is heated in the bottom of a distillation column during the time the distillative separation operation is being carried out, a thermal denaturation reaction like that described above may occur according to this method as well, thereby preventing the obtaining of an adequate recovery rate. In addition, Patent Document 14 describes a process for producing isocyanate by thermal decomposition of a carbamic acid ester after having synthesized the carbamic acid ester by reacting a diamine and dimethyl carbonate. In this process, although the carbamic acid ester is isolated by distillative purification, this distillative purification is preferably carried out in the presence of an inert solvent having a boiling point at least 10° C. lower than the carbamic acid ester. In this distillative purification method, since the carbamic acid ester is heated in the bottom of a distillation column in the same manner as the previously described method, the recovery rate cannot be said to be adequate.

In this manner, methods for separating carbamic acid esters from a mixture obtained in a carbamic acid ester production process still have problems remaining.

On the other hand, various methods have been proposed for producing isocyanates by using a carbamic acid ester as a raw material.

According to the description of Patent Document 3, an aliphatic diurethane and/or alicyclic diurethane and/or aliphatic polyurethane and/or alicyclic polyurethane are obtained by reacting an aliphatic primary diamine and/or alicyclic primary diamine and/or aliphatic primary polyamine and/or alicyclic primary polyamine with O-alkylcarbamate in the presence of an alcohol and in the presence or absence of a catalyst at from 160 to 300° C. at a ratio of amine $NH_2$ group: carbamate: alcohol of 1:0.8 to 10:0.25 to 50, followed by removing the ammonia formed as necessary. The resulting diurethane and/or polyurethane can be converted to the corresponding diisocyanate and/or highly functional polyisocyanate as necessary. Detailed reaction conditions with respect to thermal decomposition are not described in this publication.

According to Patent Document 4, an aromatic diisocyanate and/or polyisocyanate are produced by going through the following two steps. In the first step, an aromatic primary amine and/or aromatic primary polyamine are reacted with O-alkylcarbamate in the presence or absence of a catalyst and in the presence or absence of urea and alcohol to form an aryl diurethane and/or aryl polyurethane followed by removing the ammonia formed as necessary. In the second step, an aromatic isocyanate and/or aromatic polyisocyanate are obtained by thermal decomposition of the aryl diurethane and/or aryl polyurethane.

Several methods are known for forming a corresponding isocyanate and alcohol by thermal decomposition of a (cyclic) aliphatic, and particularly aromatic monourethane and diurethane, and although these methods may include methods carried out in a gaseous phase at a high temperature and methods carried out in a liquid phase under comparatively low temperature conditions, since there are cases in which the reaction mixture forms precipitates, polymeric substances and occlusions in the reaction vessel and recovery apparatus due to the occurrence of side reactions as described above, for example, economic efficiency is poor in the case of producing isocyanates over a long period of time.

Thus, chemical methods such as the use of a special catalyst (see Patent Document 15 and Patent Document 16) or a catalyst in combination with an inert solvent (see Patent Document 17) have been disclosed to improve yield during thermal decomposition of urethanes.

More specifically, Patent Document 18 describes a process for producing hexamethylene diisocyanate comprising thermal decomposition of hexamethylene diethylurethane in the presence of dibenzyl toluene used as a solvent, and in the presence of a catalyst mixture containing methyl toluenesulfonate and diphenyl tin dichloride. However, since there is no detailed description provided regarding production of the starting components or isolation, purification or voluntary recovery of the solvent and catalyst mixture, it is not possible to assess the economic efficiency of this process.

According to the method described in Patent Document 19, urethane can be easily decomposed to an isocyanate and an alcohol in a carbon-containing fluidized bed without using a catalyst. In addition, according to Patent Document 20, hexamethylene dialkyl urethane can be decomposed in a gaseous phase at a temperature in excess of 300° C. in the presence or absence of a gas-permeable packaging material composed of, for example, carbon, copper, bronze, steel, zinc, aluminum, titanium, chromium, cobalt or quartz to form hexamethylene diisocyanate. According to the description of Patent Document 14, the process is carried out in the presence of a hydrogen halide and/or hydrogen halide donor. However, this method is unable to achieve a hexamethylene diisocyanate yield of 90% or more. This is because the decomposition products are partially rebonded resulting in the formation of urethane bonds. Thus, further purification of hexamethylene diisocyanate by distillation is required, and this frequently results in an increase in yield loss.

Moreover, Patent Document 21 discloses that a monocarbamate can be decomposed at a satisfactory yield without using a solvent in the presence or absence of a catalyst and/or stabilizer advantageously under reduced pressure and at a comparatively low temperature. The decomposition products (monoisocyanate and alcohol) are removed from the boiling reaction mixture by distillation and are captured separately by fractional condensation. A method is described in a generic form for partially removing the reaction mixture in order to remove by-products formed during thermal decomposition. Thus, although by-products can be removed from the bottom of the reaction vessel, the problem with respect to the case of adhering to the walls of the reaction vessel as previously described remains, and the problem with respect to long-term operation is unresolved. In addition, there is no description regarding the industrial use of the removed residue (containing a large amount of useful components).

According to the description of Patent Document 22, thermal decomposition of an aliphatic, alicyclic or aromatic polycarbamate is carried at from 150 to 350° C. and from 0.001 to 20 bar in the presence of an inert solvent and in the presence or absence of a catalyst, auxiliary agent in the form of hydrogen chloride, organic acid chloride, alkylating agent or organic tin chloride. By-products formed can be removed continuously from the reaction vessel together with the reaction solution, for example, and a corresponding amount of fresh solvent or recovered solvent is added simultaneously. A disadvantage of this method is that, for example, a decrease in the space-time yield of polyisocyanate occurs due to the use of a refluxing solvent, and what is more, a large amount of energy is required, including that for recovering the solvent, for example. Moreover, the auxiliary agent that is used is volatile under the reaction conditions, and the decomposition products may be contaminated. In addition, the amount of residue is large relative to the amount of polyisocyanate formed, thereby making the economic efficiency and reliability as an industrial method suspect.

Patent Document 23 describes one method for continuous thermal decomposition of a carbamate, such as an alicyclic diurethane 5-(ethoxycarbonylamino)-1-(ethoxycarbonylaminomethyl)-1,3,3-trimethylcyclohexane, supplied along the inner surface of a tubular reaction vessel in a liquid form in the presence of a high boiling point solvent. This method has the disadvantages of low yield and low selectivity during production of a (cyclic) aliphatic diisocyanate. In addition, there is no description of a continuous method accompanying recovery of rebonded or partially decomposed carbamate, and post-treatment of solvent containing by-products and catalyst is also not mentioned.

The description of Patent Document 24 relates to a circulation method for producing (cyclic) aliphatic diisocyanate by converting a corresponding diamine to diurethane followed by thermal decomposition of this urethane. This method minimizes the decrease in yield by recirculating the product from a urethane decomposition step to an urethanation step following reaction with alcohol. By-products that are unable to be recirculated are removed by separation by distilling a mixture of urethanation products, and in this case, unwanted residue forms in the form of bottom products while all comparatively low boiling point components, including diurethane, are removed from the top of the column. This method, however has a disadvantage of using a large amount of energy. This is because all diurethane is required to be evaporated in the presence of a catalyst, and this diurethane must be evaporated at a temperature level within the range of the decomposition temperature of urethane. Isocyanate groups formed in useful products react with residual urethane groups, frequently resulting in the formation of comparatively high molecular weight by-products that cause a reduction in yield.

In addition, according to the description of Patent Document 25, a method is disclosed whereby unwanted by-products are partially removed prior to carrying out thermal decomposition of polyurethane. The disadvantage of this method is that the yield of isocyanate decreases as a result of polyurethane being contained in the partially removed by-products. In addition, since polymeric compounds form and adhere to the reaction vessel as a result of heating of by-products remaining in the reaction vessel without being discharged from the reaction vessel, long-term, continuous operation is difficult.

As has been described above, processes for producing isocyanates using carbamic acid esters as raw materials have numerous problems to be solved and have yet to be industrialized.

Patent Document 1: Japanese Patent Application Laid-open No. S59-48452
Patent Document 2: Japanese Patent Application Laid-open No. 2004-262831
Patent Document 3: U.S. Pat. No. 4,497,963
Patent Document 4: U.S. Pat. No. 4,290,970
Patent Document 5: U.S. Pat. No. 4,388,238)
Patent Document 6: U.S. Pat. No. 4,430,505)
Patent Document 7: U.S. Pat. No. 4,480,110
Patent Document 8: U.S. Pat. No. 4,596,678
Patent Document 9: U.S. Pat. No. 4,596,679
Patent Document 10: European Patent Laid-open No. 0320235
Patent Document 11: U.S. Pat. No. 4,395,565
Patent Document 12: Japanese Patent Application Laid-open No. H10-87598
Patent Document 13: Japanese Patent Application Laid-open No. 2001-48839

Patent Document 14: Japanese Patent Application Laid-open No. S64-85956
Patent Document 15: U.S. Pat. No. 2,692,275
Patent Document 16: U.S. Pat. No. 3,734,941
Patent Document 17: U.S. Pat. No. 4,081,472
Patent Document 18: U.S. Pat. No. 4,388,426
Patent Document 19: U.S. Pat. No. 4,482,499
Patent Document 20: U.S. Pat. No. 4,613,466
Patent Document 21: U.S. Pat. No. 4,386,033
Patent Document 22: U.S. Pat. No. 4,388,246
Patent Document 23: U.S. Pat. No. 4,692,550
Patent Document 24: European Patent No. 0355443
Patent Document 25: Japanese Patent No. 3382289
Non-Patent Document 1: Berchte der Deutechen Chemischen Gesellschaft, Vol. 3, p. 653, 1870
Non-Patent Document 2: Journal of American Chemical Society, Vol. 81, p. 2138, 1959

DISCLOSURE OF INVENTION

Problems to be Solved by the Invention

An object of the present invention is to provide an isocyanate production process, which is free of the various problems found in the prior art, that uses a composition containing a carbamic acid ester and an aromatic hydroxy compound, and a carbamic acid ester composition for transferring or storing carbamic acid ester.

Means for Solving the Problems

Therefore, as a result of conducting extensive studies on the above-mentioned problems, the inventors of the present invention found that isocyanate can be produced in good yield by an isocyanate production process containing specific steps that uses a composition containing a carbamic acid ester and a specific aromatic hydroxy compound, thereby leading to completion of the present invention. In addition, the inventors of the present invention also found that the carbamic acid ester composition containing the carbamic acid ester and the specific aromatic hydroxy compound is preferable as a composition for transferring or storing carbamic acid ester, thereby leading to completion of the present invention.

Namely, according to the first aspect of the present invention, there are provided:

[1] a process for producing an isocyanate using a composition containing a carbamic acid ester and an aromatic hydroxy compound, the process comprising the step of transferring the composition to a reaction vessel in which a thermal decomposition reaction of the carbamic acid ester occurs, wherein when number of mole of an ester group constituting the carbamic acid ester is defined as A, and number of mole of the aromatic hydroxy compound is defined as B, then a ratio of B to A is within a range of from 0.1 to 50, a melting point of the carbamic acid ester is 200° C. or lower, and a melting point of the aromatic hydroxy compound is 190° C. or lower,

[2] the process according to item [1], wherein isocyanate is produced by a process comprising the following steps (1), (3), (4) and (5), or a process comprising the following steps (2), (3), (4) and (5):

step (1): reacting an amine compound and the carbonic acid ester so as to obtain a mixture containing a carbamic acid ester, an alcohol and a carbonic acid ester;

step (2): reacting an amine compound, an urea and an alcohol so as to obtain a mixture containing a carbamic acid ester, an alcohol and a urea compound;

step (3): separating the alcohol and the carbonic acid ester or the urea contained in the mixture by using the mixture of step (1) or step (2) and the aromatic hydroxy compound so as to obtain a composition containing the carbamic acid ester and the aromatic hydroxy compound;

step (4): transferring the composition obtained in step (3) in a liquid state to a reaction vessel in which step (5) is carried out; and step (5): producing the isocyanate using the composition transferred in step (4),

[3] the process according to item [2], wherein a normal boiling point of the aromatic hydroxy compound is higher than a normal boiling point of a compound represented by ROH having a structure in which a hydrogen atom is added to RO constituting the ester group of the carbamic acid ester (wherein R represents an alkyl group and O represents an oxygen atom),

[4] the process according to item [3], wherein a normal boiling point of the aromatic hydroxy compound is higher than a normal boiling point of a compound represented by ROCOOR having a structure in which an RO group constituting the ester group of the carbamic acid ester (wherein R represents an alkyl group and O represents an oxygen atom) is bonded through a carbonyl group,

[5] the process according to item [4], wherein the step (3) is a step in which the composition containing the carbamic acid ester and the aromatic hydroxy compound is obtained from a mixture of the mixture of the step (1) or the step (2) and the aromatic hydroxy compound by separating the alcohol and the carbonic acid ester or the urea,

[6] the process according to item [5], wherein the step (3) is a step carried out in a distillation column, in which the composition containing the carbamic acid ester and the aromatic hydroxy compound is obtained from a bottom of the distillation column by supplying the mixture of the step (1) or the step (2) to the distillation column in a form of a mixture with the aromatic hydroxy compound, and recovering the alcohol and the carbonic acid ester or the urea from a top of the column,

[7] the process according to item [4], wherein the step (3) is a step in which a mixture obtained by separating all or a portion of the alcohol and/or a portion of the carbonic acid ester or the urea from the mixture of the step (1) or the step (2) is mixed with the aromatic hydroxy compound to obtain a mixture, and the carbonic acid ester or the urea is separated from the mixture,

[8] the process according to item [7], wherein the step (3) is a step carried out in a distillation column, and further comprises the following steps (3-1) and (3-2):

step (3-1): supplying the mixture of the step (1) or the step (2) to the distillation column, an alcohol and/or a carbonic acid ester or an urea being recovered from a top of the column, and a mixture containing the carbamic acid ester, the alcohol and/or the carbonic acid ester or the urea being recovered from a bottom of the column; and step (3-2): supplying the mixture of the step (3-1) to the distillation column in a form of a mixture with the aromatic hydroxy compound, the alcohol and/or the carbonic acid ester or the urea being recovered from the top of the column, and the composition containing the carbamic acid ester and the aromatic hydroxy compound being recovered from the bottom of the column,

[9] the process according to item [2], further comprising a step in which the carbonic acid ester or the urea separated in the step (3) is reused as the carbonic acid ester of the step (1) or the urea of the step (2),

[10] the process according to item [2], wherein the step (4) is carried out at 180° C. or lower,

[11] the process according to item [2], wherein the step (5) is a step in which the carbamic acid ester contained in the composition of the step (4) is subjected to a thermal decomposition reaction, and in which a low boiling point component formed by the thermal decomposition reaction is recovered as a gaseous component from the reaction vessel in which the thermal decomposition reaction occurs, and all or a portion of the mixture containing the carbamic acid ester and/or the aromatic hydroxy compound is recovered from the bottom of the reaction vessel,

[12] the process according to item [11], wherein the low boiling point component is an alcohol derived from the carbamic acid ester,

[13] the process according to item [2], wherein the step (5) is a step in which the composition of the step (4) is heated, the carbamic acid ester and the aromatic hydroxy compound which are contained in the composition are reacted to obtain an aryl carbamate having a group derived from the aromatic hydroxy compound, and the aryl carbamate is subjected to a thermal decomposition reaction so as to produce an isocyanate,

[14] the process according to item [13], wherein the step (5) comprises the following step (5-1) and step (5-2):

step (5-1): reacting the carbamic acid ester and aromatic hydroxy compound which are contained in the composition of the step (4), a low boiling point component formed being recovered in a form of a gaseous component, and a reaction liquid containing the aryl carbamate and the aromatic hydroxy compound being removed from the bottom of the reaction vessel in which the reaction occurs; and step (5-2): supplying the reaction liquid of the step (5-1) to a reaction vessel in which a thermal decomposition reaction occurs, the aryl carbamate being subjected to a thermal decomposition reaction, at least one of either an isocyanate or an aromatic hydroxy compound which are formed being recovered in a form of a gaseous component, and all or a portion of a mixture containing the isocyanate and/or the aromatic hydroxy compound and/or the aryl carbamate not recovered in a form of a gaseous component being recovered from the bottom of the reaction vessel,

[15] the process according to item [14], wherein the low boiling point component of the step (5-1) is an alcohol derived from the carbamic acid ester,

[16] the process according to item [11] or [14], wherein the aromatic hydroxy compound is recovered from the mixture according to item [11] recovered from the bottom of the reaction vessel and containing the carbamic acid ester and/or the aromatic hydroxy compound, or the reaction liquid of the step (5-1) according to item [14], the mixture recovered from the bottom of the reaction vessel and/or the compound recovered in the form of a gaseous component in step the (5-2) according to item [14], and the aromatic hydroxy compound is reused as the aromatic hydroxy compound of the step (3),

[17] the process according to item [2], wherein the alcohol separated in the step (3) according to item [2] and/or the alcohol according to item [10] and/or item [13], is used as all or a portion of the alcohol in the step (2) according to item [2],

[18] the process according to item [4], wherein a molecular weight of the aromatic hydroxy compound is within a range of from 120 to 370,

[19] the process according to item [18], wherein the aromatic hydroxy compound is a compound having one hydroxyl group directly bonded to an aromatic hydrocarbon ring constituting the aromatic hydroxy compound,

[20] the process according to item [19], wherein the aromatic hydroxy compound is an aromatic hydroxy compound which is represented by the following formula (5), and which has at least one substituent $R^1$:

(wherein ring A represents a single or multiple aromatic hydrocarbon ring which may have a substituent, and which have 6 to 20 carbon atoms, and $R^1$ represents an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the above groups containing an atom selected from the group consisting of carbon, oxygen and nitrogen atoms, and $R^1$ may bond with A to form a ring structure),

[21] the process according to item [20], wherein the aromatic hydroxy compound has a structure in which ring A contains at least one structure selected from the group consisting of a benzene ring, a naphthalene ring and an anthracene ring,

[22] the process according to item [21], wherein the aromatic hydroxy compound is a compound represented by the following formula (6):

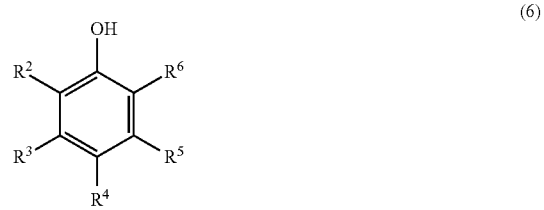

(wherein, each of $R^2$, $R^3$, $R^4$, $R^5$ and $R^6$ independently represents a hydrogen atom, or an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the above groups containing an atom selected from the group consisting of carbon, oxygen and nitrogen atoms, and at least one of $R^2$, $R^3$, $R^4$, $R^5$ and $R^6$ is not a hydrogen atom),

[23] the process according to item [22], wherein the aromatic hydroxy compound is a compound represented by the formula (2) in which $R^2$ is not a hydrogen atom,

[24] the process according to item [23], wherein the aromatic hydroxy compound is a compound represented by the formula (2) in which a total number of carbon atoms constituting $R^2$ and $R^6$ is from 2 to 20,

[25] the process according to item [2], wherein the amine compound of the step (1) is a polyamine compound,

[26] the process according to item [25], wherein the amine compound is a compound represented by the following formula (7):

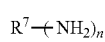
(7)

(wherein $R^7$ represents a group which is selected from the group consisting of an aliphatic group having 1 to 20 carbon atoms and an aromatic group having 6 to 20 carbon atoms, the aliphatic group and the aromatic group contain an atom selected from carbon and oxygen atoms, and have a valence equal to n, and n represents an integer of 2 to 10),

[27] the process according to item [26], wherein the polyamine compound is a diamine compound in which n in the formula (3) is 2,

[28] the process according to item [27], wherein the diamine compound is a compound in which $R^7$ in the formula (3) is an aliphatic group which has 1 to 20 carbon atoms, and which contains an atoms selected from carbon and oxygen atoms,

[29] the process according to item [28], wherein the diamine compound is at least one compound selected from the group consisting of compounds represented by the following formulas (8), (9) and (10):

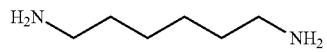
(8)

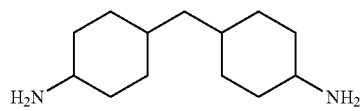
(9)

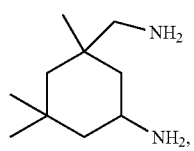
(10)

[30] the process according to item [2], wherein the carbonic acid ester is a compound represented by the following formula (11):

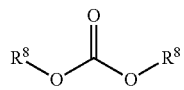
(11)

(wherein $R^8$ represents a linear or branched alkyl group having 1 to 8 carbon atoms),

[31] the process according to item [30], wherein the carbonic acid ester is produced by a process comprising the following step (A) and step (B):

step (A): reacting an organic tin compound having a tin-oxygen-carbon bond and carbon dioxide so as to obtain a reaction mixture containing the carbonic acid ester; and step (B): separating the carbonic acid ester from the reaction mixture as well as obtaining a distillation residue,

[32] the process according to item [31], further comprising the following step (C) and step (D) in addition to the step (A) and the step (B) according to item [31]:

step (C): reacting the distillation residue obtained in step (B) with alcohol so as to form an organic tin compound having a tin-oxygen-carbon bond and a water, followed by removing the water from a reaction system; and step (D): reusing the organic tin compound having the tin-oxygen-carbon bond obtained in the step (C) as the organic tin compound having a tin-oxygen-carbon bond of step (A),

[33] the process according to item [32], wherein the alcohol separated in the step (3) according to item [2] and/or the alcohol according to item [10] and/or item [13] is used as all or a portion of the alcohol in the step (C) according to item [32],

[34] the process according to item [2], wherein the alcohol of the step (1) is an alcohol having an alkyl group derived from the carbonic acid ester,

[35] the process according to item [2], wherein the reaction between the amine compound and the carbonic acid ester in the step (1) is carried out in the presence of a metal alkoxide compound,

[36] the process according to item [35], wherein the metal alkoxide compound is an alkoxide compound of an alkaline metal or an alkaline earth metal,

[37] the process according to item [36], wherein an alkyl group constituting the carbonic acid ester is identical to an alkyl group constituting the metal alkoxide compound,

[38] the process according to item [2], wherein the alcohol of the step (2) is a compound represented by the following formula (12):

(12)

(wherein $R^9$ represents a linear or branched alkyl group having 1 to 10 carbon atoms),

[39] the process according to item [2], wherein the carbamic acid ester is a polycarbamic acid ester,

[40] the process according to item [39], wherein the polycarbamic acid ester is a compound represented by the following formula (13):

(13)

(wherein $R^7$ has the same meaning as defined above, $R^{11}$ represents an aliphatic group or an aromatic group which has 1 to 10 carbon atoms, and which contains an atom selected from carbon and oxygen atoms, and n represents an integer of 2 to 10),

[41] the process according to item [40], wherein the polycarbamic acid ester is a compound represented by the formula (9) in which n is 2,

[42] the process according to item [41], wherein the polycarbamic acid ester is a compound represented by the formula (9) in which $R^{11}$ is an aliphatic group which has 1 to 10 carbon atoms, and which contains an atom selected from carbon and oxygen atoms,

[43] the process according to item [42], wherein the polycarbamic acid ester is a compound represented by the formula (9) in which $R^7$ is a group selected from the group consisting of an alkyl group having 1 to 20 carbon atoms and a cycloalkyl group having 5 to 20 carbon atoms,

[44] the process according to item [43], wherein the polycarbamic acid ester is at least one of compound selected from the group consisting of compounds represented by the following formulas (14), (15) and (16):

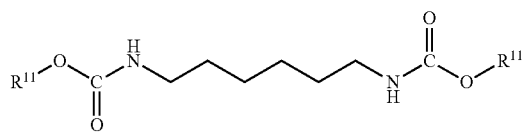
(14)

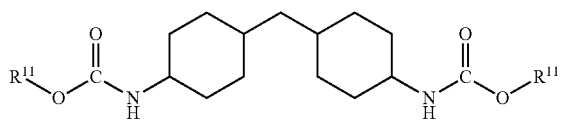
(15)

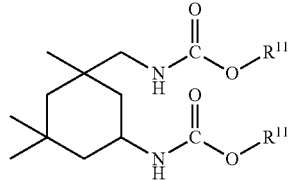
(16)

(wherein $R^{11}$ has the same meaning as defined above).

In addition, according to the second aspect of the present invention, there is provides:

[45] a composition for transfer and storage of a carbamic acid ester comprising: a carbamic acid ester; and an aromatic hydroxy compound, wherein when number of mole of an ester group constituting the carbamic acid ester is defined as A, and number of mole of an aromatic hydroxy compound is defined as B, then a ratio of B to A is within a range of from 0.1 to 50, a melting point of the carbamic acid ester is 200° C. or lower, and a melting point of the aromatic hydroxy compound is 190° C. or lower.

Advantageous Effects of the Invention

Use of the composition according to the present invention enables isocyanate to be efficiently produced without using phosgene. In addition, the composition according to the present invention is able to inhibit a thermal decomposition reaction of carbamic acid ester during transfer and storage thereof.

BEST MODE FOR CARRYING OUT THE INVENTION

The following provides a detailed explanation of the best mode for carrying out the present invention (to be referred to as the "present embodiment"). Furthermore, the present invention is not limited to the following present embodiment, but rather can be modified in various ways within the scope of the gist thereof.

An explanation is first provided of a composition comprising a carbamic acid ester and an aromatic hydroxy compound in the present embodiment.

In the composition comprising the carbamic acid ester and the aromatic hydroxy compound in the present embodiment:

when the number of mole of an ester group constituting the carbamic acid ester contained in the composition is defined as A, and the number of mole of the aromatic hydroxy compound contained in the composition is defined as B, then a ratio of B to A (B/A) is preferably within a range of from 0.1 to 50, and a melting point of the composition is 150° C. or lower. In a preferable aspect of the present embodiment, the composition is a composition for transfer and storage of carbamic acid ester.

Since carbamic acid esters used in the present embodiment easily form hydrogen bonds between molecules by the ester groups constituting the carbamic acid esters, they frequently have a high melting point. In the transfer of such a carbamic acid ester, a solid carbamic acid ester, for example, is crushed or treated with a vehicle for processing into pellets and the like prior to transfer, or the carbamic acid ester is liquefied prior to transfer by heating to a temperature higher than the melting point of the carbamic acid ester. However, in the case of transferring the solid carbamic ester that has been treated with the vehicle, there is a need for a complex apparatus to ensure stable transfer of a fixed amount of carbamic acid ester or the need for a process for maintaining the form of the carbamic acid ester within a certain range in cases of the risk of clogging of the transfer line or frequent fluctuations in the form of the carbamic acid ester. On the other hand, in the case of transferring carbamic acid ester in the form of a liquid by heating, although it is necessary to heat to a temperature higher than the melting point of the carbamic acid ester (for example, 200° C.) in consideration of preventing solidification during transfer, in the case of holding a carbamic acid ester under such high temperatures, there are frequently cases in which isocyanate may be formed at undesirable locations due to the occurrence of a thermal decomposition reaction of the carbamic acid ester or the occurrence of a thermal denaturation reaction of the carbamic acid ester as previously described. The composition of the present embodiment demonstrates the effect of being able to maintain the stability of the carbamic acid ester by inhibiting thermal denaturation of the carbamic acid ester in the composition during transfer or storage of the composition. Although the mechanism by which the effect of inhibiting thermal denaturation of the carbamic acid ester is demonstrated is not clear, the inventors of the present invention presumed that, as a result of the aromatic hydroxy compound that forms the composition forming hydrogen bonds between urethane bonds (—NHCOO—) of the carbamic acid ester and the aromatic hydroxy compound, a state is formed in which the urethane bonds have difficulty in approaching each other, thereby making it difficult for a reaction that forms urea bonds to occur as in, for example, a reaction that forms urea bonds represented by formula (2) above.

In the composition of the present embodiment, although the number of mole (B) of the aromatic hydroxy compound is preferably greater than the number of mole (A) of the ester group constituting the carbamic acid ester, on the other hand, in consideration of carbamic acid ester transfer efficiency and the size of the storage tank at the time of storage, the ratio of B to A (B/A) is preferably from 0.2 to 30, more preferably from 0.3 to 20 and even more preferably from 0.5 to 10.

In addition, the melting point of the carbamic acid ester constituting the composition of the present embodiment is 200° C. or lower, the melting point of the aromatic hydroxy compound is preferably 190° C. or lower, and the composition composed of the carbamic acid ester and the aromatic hydroxy compound is preferably a homogeneous liquid at 180° C. When transferring the composition in liquid form, although the composition is made to be in a liquid form by heating the composition to a temperature equal to or higher than the melting point thereof, in the case the temperature at which the composition becomes a homogeneous liquid is higher than 180° C., thermal decomposition of the carbamic acid ester constituting the composition occurs when transforming the composition into liquid form, thereby resulting in the case of isocyanate being formed at undesirable locations and making this undesirable. From such a viewpoint, the temperature at which the composition becomes a homogeneous liquid is preferably 180° C. or lower, and in consideration of the ease of maintaining the temperature of the transfer line and the like, the temperature is more preferably 150° C. or lower and even more preferably 100° C. or lower.

In general, the term "melting point" refers to a temperature when a solid phase and liquid phase are considered to be in a state of equilibrium, and indicates a value based on a pressure of one atmosphere. In the present embodiment, the melting point can be measured by the known method, such as with a melting point measuring apparatus described in the literature (Combined Chemical Dictionary 9, p. 357, Kyoritsu Shuppan Co., Ltd., Japan, 2003). In addition, melting point can readily be measured by differential scanning calorimetry (DSC) or differential thermal analysis (DTA), and for example, the endothermic peak measured during heating of a solid substance at a heating rate of 5° C./min under a nitrogen atmosphere with a differential scanning calorimeter can be defined as the melting point.

<Carbamic Acid Ester>

There are no particular limitations on the carbamic acid ester used in the present embodiment, and polycarbamic acid esters are used preferably. Examples of polycarbamic acid esters may include compounds represented by the following formula (17):

(17)

(wherein $R^7$ represents a group selected from the group consisting of an aliphatic group having 1 to 20 carbon atoms and an aromatic group having 6 to 20 carbon atoms, the above groups containing an atom selected from carbon and oxygen atoms, and having a valence equal to n, $R^{11}$ represents an aliphatic group or aromatic group having 1 to 10 carbon atoms which contains an atom selected from carbon and oxygen atoms, and n represents an integer of 2 to 10).

In formula (17) above, n is preferably a number selected from integers of 2 or more, and more preferably polycarbamic acid esters in which n is 2.

$R^{11}$ in the formula (17) preferably represents an aliphatic group having 1 to 10 carbon atoms containing an atom selected from carbon and oxygen atoms, and more preferably a hydrocarbon group having 1 to 10 carbon atoms. Examples of such $R^{11}$ may include alkyl groups in which the number of carbon atoms constituting the group is a number selected from integers of 1 to 10, such as a methyl group, an ethyl group, a propyl group (including isomers), a butyl group (including isomers), a pentyl group (including isomers), a hexyl group (including isomers), a heptyl group (including isomers) or an octyl group (including isomers); and cycloalkyl groups in which the number of carbon atoms constituting the group is a number selected from integers of 5 to 10, such as a cyclopentyl group, a cyclohexyl group, a cycloheptyl group or a cyclooctyl group.

$R^7$ in the formula (17) more preferably represents an alkyl group having 1 to 20 carbon atoms or a cycloalkyl group having 5 to 20 carbon atoms, and examples of such $R^7$ may include linear hydrocarbon groups such as methylene, dimethylene, trimethylene, tetramethylene, pentamethylene, hexamethylene or octamethylene; unsubstituted alicyclic hydrocarbon groups such as cyclopentane, cyclohexane, cycloheptane, cyclooctane or bis(cyclohexyl)alkane; alkyl-substituted cyclohexanes such as methylcyclopentane, ethylcyclopentane, methylcyclohexane (including isomers), ethylcyclohexane (including isomers), propylcyclohexane (including isomers), butylcyclohexane (including isomers), pentylcyclohexane (including isomers) or hexylcyclohexane (including isomers); dialkyl-substituted cyclohexanes such as dimethylcyclohexane (including isomers), diethylcyclohexane (including isomers) or dibutylcyclohexane (including isomers); trialkyl-substituted cyclohexanes such as 1,5,5-trimethylcyclohexane, 1,5,5-triethylcyclohexane, 1,5,5-tripropylcyclohexane (including isomers) or 1,5,5-tributylcyclohexane (including isomers); monoalkyl-substituted benzenes such as toluene, ethylbenzene or propylbenzene; dialkyl-substituted benzenes such as xylene, diethylbenzene or dipropylbenzene; and aromatic hydrocarbons such as diphenylalkane or benzene. In particular, hexamethylene, phenylene, diphenylmethane, toluene, cyclohexane, xylenyl, methylcyclohexane, isophorone and dicyclohexylmethane are used preferably.

Examples of carbamic acid esters represented by the formula (17) may include alkyl carbamates such as N,N'-hexanediyl-bis-carbamic acid dimethyl ester, N,N'-hexanediyl-bis-carbamic acid diethyl ester, N,N'-hexanediyl-bis-carbamic acid dibutyl ester (including isomers), N,N'-hexanediyl-bis-carbamic acid dipentyl ester (including isomers), N,N'-hexanediyl-bis-carbamic acid dihexyl ester (including isomers), N,N'-hexanediyl-bis-carbamic acid dioctyl ester (including isomers), dimethyl-4,4'-methylene-dicyclohexyl carbamate, diethyl-4,4'-methylene-dicyclohexyl carbamate, dipropyl-4,4'-methylene-dicyclohexyl carbamate (including isomers), dibutyl-4,4'-methylene-dicyclohexyl carbamate (including isomers), di pentyl-4,4'-methylene-dicyclohexyl carbamate (including isomers), di hexyl-4,4'-methylene-dicyclohexyl carbamate (including isomers), diheptyl-4,4'-methylene-dicyclohexyl carbamate (including isomers), dioctyl-4,4'-methylene-dicyclohexyl carbamate (including isomers), 3-(methoxycarbonylamino-methyl)-3,5,5-trimethylcyclohexyl carbamic acid methyl ester, 3-(ethoxycarbonylamino-methyl)-3,5,5-trimethylcyclohexyl carbamic acid ethyl ester, 3-(propyloxycarbonylamino-methyl)-3,5,5-trimethylcyclohexyl carbamic acid propyl ester (including isomers), 3-(butyloxycarbonylamino-methyl)-3,5,5-trimethylcyclohexyl carbamic acid butyl ester (including isomers), 3-(pentyloxycarbonylamino-methyl)-3,5,5-trimethylcyclohexyl carbamic acid pentyl ester (including isomers), 3-(hexyloxycarbonylamino-methyl)-3,5,5-trimethylcyclohexyl carbamic acid hexyl ester (including isomers), 3-(heptyloxycarbonylamino-methyl)-3,5,5-trimethylcyclohexyl carbamic acid heptyl ester (including isomers), 3-(octyloxycarbonylamino-methyl)-3,5,5-trimethylcyclohexyl carbamic acid octyl ester (including isomers), toluene-dicarbamic acid dimethyl ester (including isomers), toluene-dicarbamic acid diethyl ester (including isomers), toluene-dicarbamic acid dipropyl ester (including isomers), toluene-dicarbamic acid dibutyl ester (including isomers), toluene-dicarbamic acid dipentyl ester (including isomers), toluene-dicarbamic acid dihexyl ester (including isomers), toluene-dicarbamic acid diheptyl ester (including isomers), toluene-dicarbamic acid dioctyl ester (including isomers), N,N'-(4,4'-methanediyl-diphenyl)-biscarbamic acid dimethyl ester, N,N'-(4,4'-methanediyl-diphenyl)-biscarbamic acid diethyl ester, N,N'-(4,4'-methanediyl-diphenyl)-biscarbamic acid dipropyl ester, N,N'-(4,4'-methanediyl-diphenyl)-biscarbamic acid dibutyl ester, N,N'-(4,4'-methanediyl-diphenyl)-biscarbamic acid dipentyl ester, N,N'-(4,4'-methanediyl-diphenyl)-biscarbamic acid dihexyl ester, N,N'-(4,4'-methanediyl-diphenyl)-biscarbamic acid diheptyl ester, or N,N'-(4,4'-methanediyl-diphenyl)-biscarbamic acid dioctyl ester.

Among these, an alkyl carbamate in which $R^7$ in formula (17) above is a group selected from the group consisting of an alkyl group having 1 to 20 carbon atoms and a cycloalkyl group having 5 to 20 carbon atoms is used preferably, while an alkyl carbamate represented by any of the following formulas (18) to (20) is used particularly preferably:

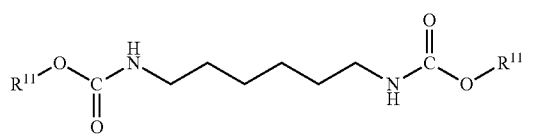
(18)

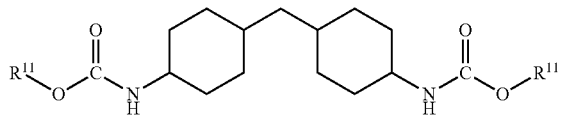
(19)

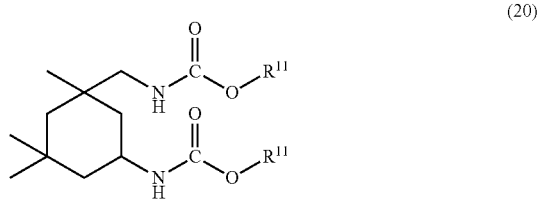
(20)

(wherein $R^{11}$ has the same meaning as defined above).

Examples of alkyl polycarbamates represented by formula (18) may include N,N'-hexanediyl-bis-carbamic acid dimethyl ester, N,N'-hexanediyl-bis-carbamic acid diethyl ester, N,N'-hexanediyl-bis-carbamic acid dibutyl ester (including isomers), N,N'-hexanediyl-bis-carbamic acid dipentyl ester (including isomers), N,N'-hexanediyl-bis-carbamic acid dihexyl ester (including isomers) and N,N'-hexanediyl-bis-carbamic acid dioctyl ester (including isomers). In addition, examples of alkyl polycarbamates represented by formula (19) may include dimethyl-4,4'-methylene-dicyclohexyl carbamate, diethyl-4,4'-methylene-dicyclohexyl carbamate, dipropyl-4,4'-methylene-dicyclohexyl carbamate (including isomers), dibutyl-4,4'-methylene-dicyclohexyl carbamate (including isomers), dipentyl-4,4'-methylene-dicyclohexyl carbamate (including isomers), dihexyl-4,4'-methylene-dicyclohexyl carbamate (including isomers), diheptyl-4,4'-methylene-dicyclohexyl carbamate (including isomers) and dioctyl-4,4'-methylene-dicyclohexyl carbamate (including isomers). Moreover, examples of alkyl polycarbamates represented by formula (20) may include alkyl polycarbamates such as 3-(methoxycarbonylamino-methyl)-3,5,5-trimethylcyclohexyl carbamic acid methyl ester, 3-(ethoxycarbonylamino-methyl)-3,5,5-trimethylcyclohexyl carbamic acid ethyl ester, 3-(propyloxycarbonylamino-methyl)-3,5,5-trimethylcyclohexyl carbamic acid propyl ester (including isomers), 3-(butyloxycarbonylamino-methyl)-3,5,5-trimethylcyclohexyl carbamic acid butyl ester (including isomers), 3-(pentyloxycarbonylamino-methyl)-3,5,5-trimethylcyclohexyl carbamic acid pentyl ester (including isomers), 3-(hexyloxycarbonylamino-methyl)-3,5,5-trimethylcyclohexyl carbamic acid hexyl ester (including isomers), 3-(heptyloxycarbonylamino-methyl)-3,5,5-trimethylcyclohexyl carbamic acid heptyl ester (including isomers) or 3-(octyloxycarbonylamino-methyl)-3,5,5-trimethylcyclohexyl carbamic acid octyl ester (including isomers).

The known method can be used to produce the carbamic acid ester. For example, carbamic acid esters may be produced by reacting amine compounds with carbon monoxide, oxygen and aliphatic alcohols or aromatic hydroxy compounds, reacting amine compounds with urea and aliphatic alcohols or aromatic hydroxy compounds, or reacting carbonic acid esters with amine compounds.

<Aromatic Hydroxy Compound>

There are no particular limitations on the aromatic hydroxy compound in the present embodiment, it is preferably an aromatic hydroxy compound in which the normal boiling point of the aromatic hydroxy compound is higher than the normal boiling point of a compound $R^{11}OH$ having a structure in which a hydrogen atom has been added to $R^{11}O$ (wherein O represents an oxygen atom) constituting an ester group of the carbamic acid ester represented by formula (17) above, more preferably an aromatic hydroxy compound in which the normal boiling point is 20° C. or more higher than that of $R^{11}OH$, and even more preferably an aromatic hydroxy compound in which the normal boiling point is 50° C. or more higher than that of $R^{11}OH$. The term "normal boiling point" referred herein indicates the boiling point at one atmosphere.

In addition, the normal boiling point of the aromatic hydroxy compound is preferably higher than the normal boiling point of a compound $R^{11}OCOOR^{11}$ having a structure in which the group $R^{11}O$ (wherein O represents an oxygen atom) constituting an ester group of a carbamic acid ester represented by formula (17) above is bonded through a carbonyl group, more preferably 10° C. or more higher than the normal boiling point of $R^{11}OCOOR^{11}$, and even more preferably 20° C. or more higher than the normal boiling point of $R^{11}OCOOR^{11}$.

In this manner, although an aromatic hydroxy compound is preferably used in which the normal boiling point thereof is higher than the normal boiling point of $R^{11}OH$ or $R^{11}OCOOR^{11}$, this is for recovering a carbamic acid ester in the form of a composition with an aromatic hydroxy compound from a bottom of a distillation column during distillative separation with a distillation column of alcohol and/or carbonic acid ester or urea in the presence of an aromatic hydroxy compound from a mixture obtained in step (1) or step (2) above in a preferable production process of the composition of the present embodiment to be described later.

In addition, the molecular weight of the aromatic hydroxy compound is preferably within a range of from 120 to 370, and more preferably within a range of from 200 to 350, in consideration of the preferable normal boiling point range described above, and preventing an excessive decrease in transfer efficiency due to an excessively low weight percentage of carbamic acid ester in the composition of the present embodiment.

Moreover, the aromatic hydroxy compound is preferably a compound having one hydroxyl group directly bonded to an aromatic hydrocarbon ring constituting the aromatic hydroxy compound. Although an aromatic hydroxy compound having two or more hydroxyl groups directly bonded to an aromatic hydrocarbon ring constituting the aromatic hydroxy compound can also be used as the aromatic hydroxy compound constituting the composition of the present embodiment, since there are cases in which the viscosity of the composition may be high, this can lead to a decrease in efficiency during transfer.

Preferable examples of compounds used as such aromatic hydroxy compounds may include aromatic hydroxy compounds which are represented by the following formula (21), and which have at least one substituent $R^1$:

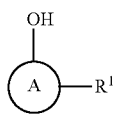

(21)

(wherein ring A represents a single or multiple aromatic hydrocarbon ring which have 6 to 20 carbon atoms, and which may have a substituent;

$R^1$ represents an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms, or an aralkyloxy group having 7 to 20 carbon atoms, the above groups containing an atom selected from the group consisting of carbon, oxygen and nitrogen atoms, and $R^1$ may bond with A to form a ring structure).

Examples of ring A in formula (21) above may include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring and an acephenanthrylene ring. Preferable examples may include rings selected from the group consisting of a benzene ring, a naphthalene ring and an anthracene ring. In addition, these rings may have a substituent other than the above-mentioned $R^1$, examples of which may include aliphatic alkyl groups in which the number of carbon atoms constituting the group is a number selected from integers of 1 to 20, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers) or an octadecyl group (including isomers); aliphatic alkoxy groups in which the number of carbon atoms constituting the group is a number selected from integers of 1 to 20, such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers) or an octadecyloxy group (including isomers); aryl groups in which the number of carbon atoms constituting the group is 6 to 20, such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); aryloxy groups in which the number of carbon atoms constituting the group is 6 to 20, such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers) or a tributylphenoxy group (including isomers); aralkyl groups in which the number of carbon atoms constituting the group is 7 to 20, such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers); and aralkyloxy groups in which the number of carbon atoms constituting the group is 7 to 20, such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers) or a phenylnonyloxy group (including isomers). These groups are preferably groups that do not contain atoms other than carbon, oxygen, nitrogen and hydrogen atoms.

Examples of $R^1$ in formula (21) above may include aliphatic alkyl groups in which the number of carbon atoms constituting the group is a number selected from integers of 1 to 20, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers) or an octadecyl group (including isomers); aliphatic alkoxy groups in which the number of carbon atoms constituting the group is a number selected from integers of 1 to 20, such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers) or an octadecyloxy group (including isomers); aryl groups in which the number of carbon atoms constituting the group is 6 to 20, such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); aryloxy groups in which the number of carbon atoms constituting the group is 6 to 20, such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers) or a tributylphenoxy group (including isomers); aralkyl groups in which the number of carbon atoms constituting the group is 7 to 20, such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers); and aralkyloxy groups in which the number of carbon atoms constituting the group is 7 to 20, such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers) or a phenylnonyloxy group (including isomers). These groups are preferably groups that do not contain atoms other than carbon, oxygen, nitrogen and hydrogen atoms.

Examples of such an aromatic hydroxy compound may include compounds represented by the following formula (22):

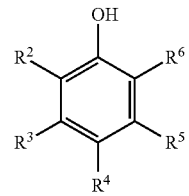

(22)

(wherein each of $R^2$, $R^3$, $R^4$, $R^5$ and $R^6$ independently represents a hydrogen atom, or an aliphatic group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the above groups containing an atom selected from the group consisting of carbon, oxygen and nitrogen atoms, and at least one of $R^2$, $R^3$, $R^4$, $R^5$ and $R^6$ does not represent a hydrogen atom).

Examples of $R^2$, $R^3$, $R^4$, $R^5$ and $R^6$ may include aliphatic alkyl groups in which the number of carbon atoms constituting the group is a number selected from integers of 1 to 20, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers) or an octadecyl group (including isomers); aliphatic alkoxy groups in which the number of carbon atoms constituting the group is a number selected from integers of 1 to 20, such as a methoxy group, an ethoxy group, a propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers) or an octadecyloxy group (including isomers); aryl groups in which the number of carbon atoms constituting the group is 6 to 20, such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers);

aryloxy groups in which the number of carbon atoms constituting the group is 6 to 20, such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers) or a tributylphenoxy group (including isomers); aralkyl groups in which the number of carbon atoms constituting the group is 7 to 20, such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers); and aralkyloxy groups in which the number of carbon atoms constituting the group is 7 to 20, such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers) or a phenylnonyloxy group (including isomers).

Examples of aromatic hydroxy compounds may include mono-substituted phenols such as ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), phenylphenol (including isomers), phenoxyphenol (including isomers) or cumylphenol (including isomers); di-substituted phenols such as dimethylphenol (including isomers), diethylphenol (including isomers), dipropylphenol (including isomers), dibutylphenol (including isomers), dipentylphenol (including isomers), dihexylphenol (including isomers), diheptylphenol (including isomers), dioctylphenol (including isomers), dinonylphenol (including isomers), didecylphenol (including isomers), didodecylphenol (including isomers), diphenylphenol (including isomers), diphenoxyphenol (including isomers), dicumylphenol (including isomers), methylethylphenol (including isomers), methylpropylphenol (including isomers), methylbutylphenol (including isomers), methylpentylphenol (including isomers), methylhexylphenol (including isomers), methylheptylphenol (including isomers), methyloctylphenol (including isomers), methylnonylphenol (including isomers), methyldecylphenol (including isomers), methyldodecylphenol (including isomers), methylphenylphenol (including isomers), methylphenoxyphenol (including isomers), methylcumylphenol (including isomers), ethylpropylphenol (including isomers), ethylbutylphenol (including isomers), ethylpentylphenol (including isomers), ethylhexylphenol (including isomers), ethylheptylphenol (including isomers), ethyloctylphenol (including isomers), ethylnonylphenol (including isomers), ethyldecylphenol (including isomers), ethyldodecylphenol (including isomers), ethylphenylphenol (including isomers), ethylphenoxyphenol (including isomers), ethylcumylphenol (including isomers), propylbutylphenol (including isomers), propylpentylphenol (including isomers), propylhexylphenol (including isomers), propylheptylphenol (including isomers), propyloctylphenol (including isomers), propylnonylphenol (including isomers), propyldecylphenol (including isomers), propyldodecylphenol (including isomers), propylphenylphenol (including isomers), propylphenoxyphenol (including isomers), propylcumylphenol (including isomers), butylpentylphenol (including isomers), butylhexylphenol (including isomers), butylheptylphenol (including isomers), butyloctylphenol (including isomers), butylnonylphenol (including isomers), butyldecylphenol (including isomers), butyldodecylphenol (including isomers), butylphenylphenol (including isomers), butylphenoxyphenol (including isomers), butylcumylphenol (including isomers), pentylhexylphenol (including isomers), pentylheptylphenol (including isomers), pentyloctylphenol (including isomers), pentylnonylphenol (including isomers), pentyldecylphenol (including isomers), pentyldodecylphenol (including isomers), pentylphenylphenol (including isomers), pentylphenoxyphenol (including isomers), pentylcumylphenol (including isomers), hexylheptylphenol (including isomers), hexyloctylphenol (including isomers), hexylnonylphenol (including isomers), hexyldecylphenol (including isomers), hexyldodecylphenol (including isomers), hexylphenylphenol (including isomers), hexylphenoxyphenol (including isomers), hexylcumylphenol (including isomers), heptyloctylphenol (including isomers), heptylnonylphenol (including isomers), heptyldecylphenol (including isomers), heptyldodecylphenol (including isomers), heptylphenylphenol (including isomers), heptylphenoxyphenol (including isomers), heptylcumylphenol (including isomers), octylnonylphenol (including isomers), octyldecylphenol (including isomers), octyldodecylphenol (including isomers), octylphenylphenol (including isomers), octylphenoxyphenol (including isomers), octylcumylphenol (including isomers), nonyldecylphenol (including isomers), nonyldodecylphenol (including isomers), nonylphenylphenol (including isomers), nonylphenoxyphenol (including isomers), nonylcumylphenol (including isomers), dodecylphenylphenol (including isomers), dodecylphenoxyphenol (including isomers) or dodecylcumylphenol (including isomers); and, tri-substituted phenols such as trimethylphenol (including isomers), triethylphenol (including isomers), tripropylphenol (including isomers), tributylphenol (including isomers), tripentylphenol (including isomers), trihexylphenol (including isomers), triheptylphenol (including isomers), trioctylphenol (including isomers), trinonylphenol (including isomers), tridecylphenol (including isomers), tridodecylphenol (including isomers), triphenylphenol (including isomers), triphenoxyphenol (including isomers), tricumylphenol (including isomers), dimethylethylphenol (including isomers), dimethylpropylphenol (including isomers), dimethylbutylphenol (including isomers), dimethylpentylphenol (including isomers), dimethylhexylphenol (including isomers), dimethylheptylphenol (including isomers), dimethyloctylphenol (including isomers), dimethylnonylphenol (including isomers), dimethyldecylphenol (including isomers), dimethyldodecylphenol (including isomers), dimethylphenylphenol (including isomers), dimethylphenoxyphenol (including isomers), dimethylcumylphenol (including isomers), diethylmethylphenol (including isomers), diethylpropylphenol (including isomers), diethylbutylphenol (including isomers), diethylpentylphenol (including isomers), diethylhexylphenol (including isomers), diethylheptylphenol (including isomers), diethyloctylphenol (including isomers), diethylnonylphenol (including isomers), diethyldecylphenol (including isomers), diethyldodecylphenol (including isomers), diethylphenylphenol (including isomers), diethylphenoxyphenol (including isomers), diethylcumylphenol (including isomers), dipropylmethylphenol (including isomers), dipropylethylphenol (including isomers), dipropylbutylphenol (including isomers), dipropylpentylphenol (including isomers), dipropylhexylphenol (including isomers), dipropylheptylphenol (including isomers), dipropyloctylphenol (including isomers), dipropylnonylphenol (including isomers), dipropyldecylphenol (including isomers), dipropyldodecylphenol (including isomers), dipropylphenylphenol (including isomers), dipropylphenoxyphenol (including isomers), dipropylcumylphenol (including isomers), dibutylmethylphenol (including isomers), dibutylethylphenol (including isomers), dibutylpropylphenol (including isomers), dibutylpentylphenol (including isomers), dibutylhexylphenol (including isomers), dibutylheptylphenol (including isomers), dibutyloctylphenol (including isomers), dibutylnonylphenol (including isomers), dibutyldecylphenol (including isomers), dibutyldodecylphenol (including isomers), dibutylphenylphenol (including isomers), dibutylphenoxyphenol (including isomers), dibutylcumylphenol (including isomers), dipentylmethylphenol (including isomers), dipentylethylphenol (including isomers), dipentylpropylphenol (including isomers), dipentylbutylphenol (including isomers), dipentylhexylphenol (including isomers), dipentylheptylphenol (including isomers), dipentyloctylphenol (including isomers), dipentylnonylphenol (including isomers), dipentyldecylphenol (including isomers), dipentyldodecylphenol (including isomers), dipentylphenylphenol (including isomers), dipentylphenoxyphenol (including isomers), dipentylcumylphenol (including isomers), dihexylmethylphenol (including isomers), dihexylethylphenol (including isomers), dihexylpropylphenol (including isomers), dihexylbutylphenol (including isomers), dihexylpentylphenol (including isomers), dihexylheptylphenol (including isomers), dihexyloctylphenol (including isomers), dihexylnonylphenol (including isomers), dihexyldecylphenol (including isomers), dihexyldodecylphenol (including isomers), dihexylphenylphenol (including isomers), dihexylphenoxyphenol (including isomers), dihexylcumylphenol (including isomers), diheptylmethylphenol (including isomers), diheptylethylphenol (including isomers), diheptylpropylphenol (including isomers), diheptylbutylphenol (including isomers), diheptylpentylphenol (including isomers), diheptylhexylphenol (including isomers), diheptyloctylphenol (including isomers), diheptylnonylphenol (including isomers), diheptyldecylphenol (including isomers), diheptyldodecylphenol (including isomers), diheptylphenylphenol (including isomers), diheptylphenoxyphenol (including isomers), diheptylcumylphenol (including isomers), dioctylmethylphenol (including isomers), dioctylethylphenol (including isomers), dioctylpropylphenol (including isomers), dioctylbutylphenol (including isomers), dioctylpentylphenol (including isomers), dioctylhexylphenol (including isomers), dioctylheptylphenol (including isomers), dioctylnonylphenol (including isomers), dioctyldecylphenol (including isomers), dioctyldodecylphenol (including isomers), dioctylphenylphenol (including isomers), dioctylphenoxyphenol (including isomers), dioctylcumylphenol (including isomers), dinonylmethylphenol (including isomers), dinonylethylphenol (including isomers), dinonylpropylphenol (including isomers), dinonylbutylphenol (including isomers), dinonylpentylphenol (including isomers), dinonylhexylphenol (including isomers), dinonylheptylphenol (including isomers), dinonyloctylphenol (including isomers), dinonyldecylphenol (including isomers), dinonyldodecylphenol (including isomers), dinonylphenylphenol (including isomers), dinonylphenoxyphenol (including isomers), dinonylcumylphenol (including isomers), didecylmethylphenol (including isomers), didecylethylphenol (including isomers), didecylpropylphenol (including isomers), didecylbutylphenol (including isomers), didecylpentylphenol (including isomers), didecylhexylphenol (including isomers), didecylheptylphenol (including isomers), didecyloctylphenol (including isomers), didecylnonylphenol (including isomers), didecyldodecylphenol (including isomers), didecylphenylphenol (including isomers), didecylphenoxyphenol (including isomers), didecylcumylphenol (including isomers), didodecylmethylphenol (including isomers), didodecylethylphenol (including isomers), didodecylpropylphenol (including isomers), didodecylbutylphenol (including isomers), didodecylpentylphenol (including isomers), didodecylhexylphenol (including isomers), didodecylheptylphenol (including isomers), didodecyloctylphenol (including isomers), didodecylnonylphenol (including isomers), didodecyldecylphenol (including isomers), didodecyldodecylphenol (including isomers), didodecylphenylphenol (including isomers), didodecylphenoxyphenol (including isomers), didodecylcumylphenol (including isomers), diphenylmethylphenol (including isomers), diphenylethylphenol (including isomers), diphenylpropylphenol (including isomers), diphenylbutylphenol (including isomers), diphenylpentylphenol (including isomers), diphenylhexylphenol (including isomers), diphenylheptylphenol (including isomers), diphenyloctylphenol (including isomers), diphenylnonylphenol (including isomers), diphenyldecylphenol (including isomers), diphenyldodecylphenol (including isomers), diphenylphenoxyphenol (including isomers), diphenylcumylphenol (including isomers), diphenoxymethylphenol (including isomers), diphenoxyethylphenol (including isomers), diphenoxypropylphenol (including isomers), diphenoxybutylphenol (including isomers), diphenoxypentylphenol (including isomers), diphenoxyhexylphenol (including isomers), diphenoxyheptylphenol (including isomers), diphenoxyoctylphenol (including isomers), diphenoxynonylphenol (including isomers), diphenoxydecylphenol (including isomers), diphenoxydodecylphenol (including isomers), diphenoxyphenylphenol (including isomers), diphenoxycumylphenol (including isomers), dicumylmethylphenol (including isomers), dicumylethylphenol (including isomers), dicumylpropylphenol (including isomers), dicumylbutylphenol (including isomers), dicumylpentylphenol (including isomers), dicumylhexylphenol (including isomers), dicumylheptylphenol (including isomers), dicumyloctylphenol (including isomers), dicumylnonylphenol (including isomers), dicumyldecylphenol (including isomers), dicumyldodecylphenol (including isomers), dicumylphenylphenol (including isomers), dicumylphenoxyphenol (including isomers), methylethylpropylphenol (including isomers), methylethylbutylphenol (including isomers), methylethylpentylphenol (including isomers), methylethylhexylphenol (including isomers), methylethylheptylphenol (including isomers), methylethyloctylphenol (including isomers), methylethylnonylphenol (including isomers), methylethyldecylphenol (including isomers), methylethyldodecylphenol (including isomers), methylethylphenylphenol (including isomers), methylethylphenoxyphenol (including isomers), methylethylcumylphenol (including isomers), methylpropylbutylphenol (including isomers), methylpropylpentylphenol (including isomers), methylpropylhexylphenol (including isomers), methylpropylheptylphenol (including isomers), methylpropyloctylphenol (including isomers), methylpropylnonylphenol (including isomers), methylpropyldecylphenol (including isomers), methylpropyldodecylphenol (including isomers), methylpropylphenylphenol (including isomers), methylpropylphenoxyphenol (including isomers), methylpropylcumylphenol (including isomers), methylbutylpentylphenol (including isomers), methylbutylhexylphenol (including isomers), methylbutylheptylphenol (including isomers), methylbutyloctylphenol (including isomers), methylbutylnonylphenol (including isomers), methylbutyldecylphenol (including isomers), methylbutyldodecylphenol (including isomers), methylbutylphenylphenol (including isomers), methylbutylphenoxyphenol (including isomers), methylbutylcumylphenol (including isomers), methylpentylhexylphenol, methylpentylheptylphenol (including isomers), methylpentyloctylphenol (including isomers), methylpentylnonylphenol (including isomers), methylpentyldecylphenol (including isomers), methylpentyldodecylphenol (including isomers), methylpentylphenylphenol (including isomers), methylpentylphenoxyphenol (including isomers), methylpentylcumylphenol (including isomers), methylhexylheptylphenol (including isomers), methylhexyloctylphenol (including isomers), methylhexylnonylphenol (including isomers), methylhexyldecylphenol (including isomers), methylhexyldodecylphenol (including isomers), methylhexylphenylphenol (including isomers), methylhexylphenoxyphenol (including isomers), methylhexylcumylphenol (including isomers), ethylpropylbutylphenol (including isomers), ethylpropylpentylphenol (including isomers), ethylpropylhexylphenol (including isomers), ethylpropylheptylphenol (including isomers), ethylpropyloctyl phenol (including isomers), ethylpropylnonylphenol (including isomers), ethylpropyldecylphenol (including isomers), ethylpropyldodecylphenol (including isomers), ethylpropylphenylphenol (including isomers), ethylpropylphenoxyphenol (including isomers), ethylpropylcumylphenol (including isomers), ethylbutylphenol (including isomers), ethylbutylpentylphenol (including isomers), ethylbutylhexylphenol (including isomers), ethylbutylheptylphenol (including isomers), ethylbutyloctylphenol (including isomers), ethylbutylnonylphenol (including isomers), ethylbutyldecylphenol (including isomers), ethylbutyldodecylphenol (including isomers), ethylbutylphenylphenol (including isomers), ethylbutylphenoxyphenol (including isomers), ethylbutylcumylphenol (including isomers), ethylpentylhexylphenol (including isomers), ethylpentylheptylphenol (including isomers), ethylpentyloctylphenol (including isomers), ethylpentylnonylphenol (including isomers), ethylpentyldecylphenol (including isomers), ethylpentyldodecylphenol (including isomers), ethylpentylphenylphenol (including isomers), ethylpentylphenoxyphenol (including isomers), ethylpentylcumylphenol (including isomers), ethylhexylheptylphenol (including isomers), ethylhexyloctylphenol (including isomers), ethylhexylnonylphenol (including isomers), ethylhexyldecylphenol (including isomers), ethylhexyldodecylphenol (including isomers), ethylhexylphenylphenol (including isomers), ethylhexylphenoxyphenol (including isomers), ethylhexylcumylphenol (including isomers), ethylheptyloctylphenol (including isomers), ethylheptylnonylphenol (including isomers), ethylheptyldecylphenol (including isomers), ethylheptyldodecylphenol (including isomers), ethylheptylphenylphenol (including isomers), ethylheptylphenoxyphenol (including isomers), ethylheptylcumylphenol (including isomers), ethyloctylphenol (including isomers), ethyloctylnonylphenol (including isomers), ethylocyldecylphenol (including isomers), ethyloctyldodecylphenol (including isomers), ethyloctylphenylphenol (including isomers), ethyloctylphenoxyphenol (including isomers), ethyloctylcumylphenol (including isomers), ethylnonyldecylphenol (including isomers), ethylnonyldodecylphenol (including isomers), ethylnonylphenylphenol (including isomers), ethylnonylphenoxyphenol (including isomers), ethylnonylcumylphenol (including isomers), ethyldecyldodecylphenol (including isomers), ethyldecylphenylphenol (including isomers), ethyldecylphenoxyphenol (including isomers), ethyldecylcumylphenol (including isomers), ethyldodecylphenylphenol (including isomers), ethyldodecylphenoxyphenol (including isomers), ethyldodecylcumylphenol (including isomers), ethylphenylphenoxyphenol (including isomers), ethylphenylcumylphenol (including isomers), propylbutylphenol (including isomers), propylbutylpentylphenol (including isomers), propylbutylhexylphenol (including isomers), propylbutylheptylphenol (including isomers), propylbutyloctylphenol (including isomers), propylbutylnonylphenol (including isomers), propylbutyldecylphenol (including isomers), propylbutyldodecylphenol (including isomers), propylbutylphenylphenol (including isomers), propylbutylphenoxyphenol (including isomers), propylbutylcumylphenol (including isomers), propylpentylphenol (including isomers), propylpentylhexylphenol (including isomers), propylpentylheptylphenol (including isomers), propylpentyloctylphenol (including isomers), propylpentylnonylphenol (including isomers), propylpentyldecylphenol (including isomers), propylpentyldodecylphenol (including isomers), propylpentylphenylphenol (including isomers), propylpentylphenoxyphenol (including isomers), propylpentylcumylphenol (including isomers), propylhexylphenol (including isomers), propylhexylheptylphenol (including isomers), propylhexyloctylphenol (including isomers), propylhexylnonylphenol (including isomers), propylhexyldecylphenol (including isomers), propylhexyldodecylphenol (including isomers), propylhexylphenylphenol (including isomers), propylhexylphenoxyphenol (including isomers), propylhexylcumylphenol (including isomers), propylheptyloctylphenol (including isomers), propylheptylnonylphenol (including isomers), propylheptyldecylphenol (including isomers), propylheptyldodecylphenol (including isomers), propylheptylphenylphenol (including isomers), propylheptylphenoxyphenol (including isomers), propylheptylcumylphenol (including isomers), propyloctylnonylphenol (including isomers), propyloctyldecylphenol (including isomers), propyloctyldodecylphenol (including isomers), propyloctylphenylphenol (including isomers), propyloctylphenoxyphenol (including isomers), propyloctylcumylphenol (including isomers), propylnonyldecylphenol (including isomers), propylnonyldodecylphenol (including isomers), propylnonylphenylphenol (including isomers), propylnonylphenoxyphenol (including isomers), propylnonylcumylphenol (including isomers), propyldecyldodecylphenol (including isomers), propyldecylphenylphenol (including isomers), propyldecylphenoxyphenol (including isomers), propyldecylcumylphenol (including isomers), propyldodecylphenylphenol (including isomers), propyldodecylphenoxyphenol (including isomers), propyldodecylcumylphenol (including isomers), methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), phenylphenol (including isomers), phenoxyphenol (including isomers), cumylphenol (including isomers), propylphenylphenoxyphenol (including isomers), propylphenylcumylphenol (including isomers), propylphenoxycumylphenol (including isomers), propylbutylpentylphenol (including isomers), propylbutylhexylphenol (including isomers), propylbutylheptylphenol (including isomers), propylbutyloctylphenol (including isomers), propylbutylnonylphenol (including isomers), propylbutyldecylphenol (including isomers), propylbutyldodecylphenol (including isomers), propylbutylphenylphenol (including isomers), propylbutylphenoxyphenol (including isomers), propylbutylcumylphenol (including isomers), propylpentylphenol (including isomers), propylpentylhexylphenol (including isomers), propylpentylheptylphenol (including isomers), propylpentyloctylphenol (including isomers), propylpentylnonylphenol (including isomers), propylpentyldecylphenol (including isomers), propylpentyldodecylphenol (including isomers), propylpentylphenylphenol (including isomers), propylpentylphenoxyphenol (including isomers), propylpentylcumylphenol (including isomers), propylhexylheptylphenol (including isomers), propylhexyloctylphenol (including isomers), propylhexylnonylphenol (including isomers), propylhexyldecylphenol (including isomers), propylhexyldodecylphenol (including isomers), propylhexylphenylphenol (including isomers), propylhexylphenoxyphenol (including isomers), propylhexylcumylphenol (including isomers), propylheptyloctylphenol (including isomers), propylheptylnonylphenol (including isomers), propylheptyldecylphenol (including isomers), propylheptyldodecylphenol (including isomers), propylheptylphenylphenol (including isomers), propylheptylphenoxyphenol (including isomers), propylheptylcumylphenol (including isomers), propyloctylnonylphenol (including isomers), propyloctyldecylphenol (including isomers), propyloctyldodecylphenol (including isomers), propyloctylphenylphenol (including isomers), propyloctylphenoxyphenol (including isomers), propyloctylcumylphenol (including isomers), propylnonyldecylphenol (including isomers), propylnonyldodecylphenol (including isomers), propylnonylphenylphenol (including isomers), propylnonylphenoxyphenol (including isomers), propylnonylcumylphenol (including isomers), propyldecyldodecylphenol (including isomers), propyldecylphenylphenol (including isomers), propyldecylphenoxyphenol (including isomers), propyldecylcumylphenol (including isomers), propyldodecylphenylphenol (including isomers), propyldodecylphenoxyphenol (including isomers), cumylphenol (including isomers), propylphenylphenoxyphenol (including isomers), propylphenylcumylphenol (including isomers), butylpentylhexylphenol (including isomers), butylpentylheptylphenol (including isomers), butylpentyloctylphenol (including isomers), butylpentylnonylphenol (including isomers), butylpentyldecylphenol (including isomers), butylpentyldodecylphenol (including isomers), butylpentylphenylphenol (including isomers), butylpentylphenoxyphenol (including isomers), butylpentylcumylphenol (including isomers), butylhexylheptylphenol (including isomers), butylhexyloctylphenol (including isomers), butylhexylnonylphenol (including isomers), butylhexyldecylphenol (including isomers), butylhexyldodecylphenol (including isomers), butylhexylphenylphenol (including isomers), butylhexylphenoxyphenol (including isomers), butylhexylcumylphenol (including isomers), butylheptyloctylphenol (including isomers), butylheptylnonylphenol (including isomers), butylheptyldecylphenol (including isomers), butylheptyldodecylphenol (including isomers), butylheptylphenylphenol (including isomers), butylheptylphenoxyphenol (including isomers), butylheptylcumylphenol (including isomers), butyloctylnonylphenol (including isomers), butyloctyldecylphenol (including isomers), butyloctyldodecylphenol (including isomers), butyloctylphenylphenol (including isomers), butyloctylphenoxyphenol (including isomers), butyloctylcumylphenol (including isomers), butylnonyldecylphenol (including isomers), butylnonyldodecylphenol (including isomers), butylnonylphenylphenol (including isomers), butylnonylphenoxyphenol (including isomers), butylnonylcumylphenol (including isomers), butyldecyldodecylphenol (including isomers), butyldecylphenylphenol (including isomers), butyldecylphenoxyphenol (including isomers), butyldecylcumylphenol (including isomers), butyldodecylphenylphenol (including isomers), butyldodecylphenoxyphenol (including isomers), butyldodecylcumylphenol (including isomers), butylphenylphenoxyphenol (including isomers), butylphenylcumylphenol (including isomers), pentylhexylheptylphenol (including isomers), pentylhexyloctylphenol (including isomers), pentylhexylnonylphenol (including isomers), pentylhexyldecylphenol (including isomers), pentylhexyldodecylphenol (including isomers), pentylhexylphenylphenol (including isomers), pentylhexylphenoxyphenol (including isomers), pentylhexylcumylphenol (including isomers), pentylhetpyloctylphenol (including isomers), pentylheptylnonylphenol (including isomers), pentylheptyldecylphenol (including isomers), pentylheptyldodecylphenol (including isomers), pentylheptylphenylphenol (including isomers), pentylheptylphenoxyphenol (including isomers), pentylheptylcumylphenol (including isomers), pentyloctylnonylphenol (including isomers), pentyloctyldecylphenol (including isomers), pentyloctyldodecylphenol (including isomers), pentyloctylphenylphenol (including isomers), pentyloctylphenoxyphenol (including isomers), pentyloctylcumylphenol (including isomers), pentylnonyldecylphenol (including isomers), pentylnonyldodecylphenol (including isomers), pentylnonylphenylphenol (including isomers), pentylnonylphenoxyphenol (including isomers), pentylnonylcumylphenol (including isomers), pentyldecyldodecylphenol (including isomers), pentyldecylphenylphenol (including isomers), pentyldecylphenoxyphenol (including isomers), pentyldecylcumylphenol (including isomers), pentyldodecylphenylphenol (including isomers), pentyldodecylphenoxyphenol (including isomers), pentyldodecylcumylphenol (including isomers), pentylphenylphenoxyphenol (including isomers), pentylphenylcumylphenol (including isomers), hexylheptyloctylphenol (including isomers), hexylheptylnonylphenol (including isomers), hexylheptyldecylphenol (including isomers), hexylheptyldodecylphenol (including isomers), hexylheptylphenylphenol (including isomers), hexylheptylphenoxyphenol (including isomers), hexylheptylcumylphenol (including isomers), hexyloctylnonylphenol (including isomers), hexyloctyldecylphenol (including isomers), hexyloctyldodecylphenol (including isomers), hexyloctylphenylphenol (including isomers), hexyloctylphenoxyphenol (including isomers), hexyloctylcumylphenol (including isomers), hexylnonyldecylphenol (including isomers), hexylnonyldodecylphenol (including isomers), hexylnonylphenylphenol (including isomers), hexylnonylphenoxyphenol (including isomers), hexyldecyldodecylphenol (including isomers), hexyldecylphenylphenol (including isomers), hexyldecylphenoxyphenol (including isomers), hexyldecylcumylphenol (including isomers), hexyldodecylphenylphenol (including isomers), hexyldodecylphenoxyphenol (including isomers), hexyldodecylcumylphenol (including isomers), hexylphenylphenoxyphenol (including isomers), hexylphenylcumylphenol (including isomers), heptyloctylnonylphenol (including isomers), heptyloctyldecylphenol (including isomers), heptyloctyldodecylphenol (including isomers), heptyloctylphenylphenol (including isomers), heptyloctylphenoxyphenol (including isomers), heptyloctylcumylphenol (including isomers), heptylnonyldecylphenol (including isomers), heptylnonyldodecylphenol (including isomers), heptylnonylphenylphenol (including isomers), heptylnonylphenoxyphenol (including isomers), heptylnonylcumylphenol (including isomers), heptyldecyldodecylphenol (including isomers), heptyldecylphenylphenol (including isomers), heptyldecylphenoxyphenol (including isomers), heptyldecylcumylphenol (including isomers), heptyldodecylphenylphenol (including isomers), heptyldodecylphenoxyphenol (including isomers), heptyldodecylcumylphenol (including isomers), heptylphenylphenoxyphenol (including isomers), heptylphenylcumylphenol (including isomers), octylnonyldecylphenol (including isomers), octylnonyldodecylphenol (including isomers), octylnonylphenylphenol (including isomers), octylnonylphenoxyphenol (including isomers), octylnonylcumylphenol (including isomers), octyldecyldodecylphenol (including isomers), octyldecylphenylphenol (including isomers), octyldecylphenoxyphenol (including isomers), octyldecylcumylphenol (including isomers), octyldodecylphenylphenol (including isomers), octyldodecylphenoxyphenol (including isomers), octyldodecylcumylphenol (including isomers), octylphenylphenoxyphenol (including isomers), octylphenylcumylphenol (including isomers), nonyldecyldodecylphenol (including isomers), nonyldecylphenylphenol (including isomers), nonyldecylphenoxyphenol (including isomers), nonyldecylcumylphenol (including isomers), nonyldodecylphenylphenol (including isomers), nonyldodecylphenoxyphenol (including isomers), nonyldodecylcumylphenol (including isomers), nonylphenylphenoxyphenol (including isomers), nonylphenylcumylphenol (including isomers), decyldodecylphenylphenol (including isomers), decyldodecylphenoxyphenol (including isomers), decyldodecylcumylphenol (including isomers), decylphenylphenoxyphenol (including isomers), decylphenylcumylphenol (including isomers), dodecylphenylphenoxyphenol (including isomers), dodecylphenylcumylphenol (including isomers) or phenylphenoxycumylphenol (including isomers). One type of these aromatic hydroxy compounds may be used or a plurality of types may be used in combination.

The inventors of the present invention surprisingly found that the carbamic acid ester does not undergo the thermal denaturation reaction as described above and is stable in the presence of the aromatic hydroxy compound. Although the mechanism by which denaturation of carbamic acid ester is inhibited is not clear, the inventors of the present invention presumed that, for example, ester groups of the carbamic acid ester and the aromatic hydroxy compound form hydrogen bonds, and corresponding ester groups are inhibited from approaching each other by the hydrogen bonds, thereby inhibiting a decarboxylation reaction by corresponding ester groups of the carbamic acid ester as shown in formula (2) above. In addition, even more unexpectedly, the temperature at which the composition of the present embodiment, comprising the carbamic acid ester and the aromatic hydroxy compound, is a liquid is lower than the melting point of the carbamic acid ester as well as the melting point of the aromatic hydroxy compound, and since the composition can be held at a comparatively low temperature during transfer or storage in liquid form, the effect is also demonstrated by which the thermal denaturation reaction of the carbamic acid ester as described above is inhibited.

Among these aromatic hydroxy compounds, aromatic hydroxy compounds represented by formula (22) above in which $R^4$ is a group other than a hydrogen atom are used preferably, while aromatic hydroxy compounds represented by formula (22) above in which the total number of carbon atoms constituting $R^2$ and $R^6$ is 2 to 20 are even more preferable. There are no particular limitations on the combination of $R^4$ and $R^8$ provided the total number of carbon atoms constituting $R^2$ and $R^6$ is 2 to 20.

Even more preferably, each of $R^2$ and $R^4$ in formula (22) above independently represents a group represented by the following formula (23), and aromatic hydroxy compounds in which $R^3$, $R^5$ and $R^6$ are hydrogen atoms, or aromatic hydroxy compounds in which $R^2$ in formula (22) above is a linear or branched alkyl group having 1 to 8 carbon atoms, and each of $R^4$ and $R^6$ independently represents a hydrogen atom or a linear or branched alkyl group having 1 to 8 carbon atoms, is used preferably:

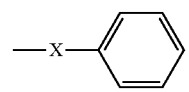

(23)

(wherein X represents a single branched structure selected from structures represented by the following formulas (24) and (25));

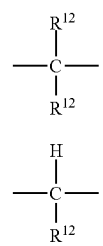

(24)

(25)

(wherein $R^{12}$ represents a linear or branched alkyl group having 1 to 3 carbon atoms).

Examples of such aromatic hydroxy compounds may include 2-ethylphenol, 2-propylphenol (including isomers), 2-butylphenol (including isomers), 2-pentylphenol (including isomers), 2-hexylphenol (including isomers), 2-heptylphenol (including isomers), 2,6-dimethylphenol, 2,4-diethylphenol, 2,6-diethylphenol, 2,4-dipropylphenol (including isomers), 2,6-dipropylphenol (including isomers), 2,4-dibutylphenol (including isomers), 2,4-dipentylphenol (including isomers), 2,4-dihexylphenol (including isomers), 2,4-diheptylphenol (including isomers), 2-methyl-6-ethylphenol, 2-methyl-6-propylphenol (including isomers), 2-methyl-6-butylphenol (including isomers), 2-methyl-6-pentylphenol (including isomers), 2-ethyl-6-propylphenol (including isomers), 2-ethyl-6-butylphenol (including isomers), 2-ethyl-6-pentylphenol (including isomers), 2-propyl-6-butylphenol (including isomers), 2-ethyl-4-methylphenol (including isomers), 2-ethyl-4-propylphenol (including isomers), 2-ethyl-4-butylphenol (including isomers), 2-ethyl-4-pentylphenol (including isomers), 2-ethyl-4-hexylphenol (including isomers), 2-ethyl-4-heptylphenol (including isomers), 2-ethyl-4-octylphenol (including isomers), 2-ethyl-4-phenylphenol (including isomers), 2-ethyl-4-cumylphenol (including isomers), 2-propyl-4-methylphenol (including isomers), 2-propyl-4-ethylphenol (including isomers), 2-propyl-4-butylphenol (including isomers), 2-propyl-4-pentylphenol (including isomers), 2-propyl-4-hexylphenol (including isomers), 2-propyl-4-hetpylphenol (including isomers), 2-propyl-4-octylphenol (including isomers), 2-propyl-4-phenylphenol (including isomers), 2-propyl-4-cumylphenol (including isomers), 2-butyl-4-methylphenol (including isomers), 2-butyl-4-ethylphenol (including isomers), 2-butyl-4-propylphenol (including isomers), 2-butyl-4-pentylphenol (including isomers), 2-butyl-4-hexylphenol (including isomers), 2-butyl-4-heptylphenol (including isomers), 2-butyl-4-octylphenol (including isomers), 2-butyl-4-phenylphenol (including isomers), 2-butyl-4-cumylphenol (including isomers), 2-pentyl-4-methylphenol (including isomers), 2-pentyl-4-ethylphenol (including isomers), 2-pentyl-4-propylphenol (including isomers), 2-pentyl-4-butylphenol (including isomers), 2-pentyl-4-hexylphenol (including isomers), 2-pentyl-4-heptylphenol (including isomers), 2-pentyl-4-octylphenol (including isomers), 2-pentyl-4-phenylphenol (including isomers), 2-pentyl-4-cumylphenol (including isomers), 2-hexyl-4-methylphenol (including isomers), 2-hexyl-4-ethylphenol (including isomers), 2-hexyl-4-propylphenol (including isomers), 2-hexyl-4-butylphenol (including isomers), 2-hexyl-4-pentylphenol (including isomers), 2-hexyl-4-heptylphenol (including isomers), 2-hexyl-4-octylphenol (including isomers), 2-hexyl-4-phenylphenol (including isomers), 2-hexyl-4-cumylphenol (including isomers), 2-heptyl-4-methylphenol (including isomers), 2-heptyl-4-ethylphenol (including isomers), 2-heptyl-4-propylphenol (including isomers), 2-heptyl-4-butylphenol (including isomers), 2-heptyl-4-pentylphenol (including isomers), 2-heptyl-4-hexylphenol (including isomers), 2-heptyl-4-octylphenol (including isomers), 2-heptyl-4-phenylphenol (including isomers), 2-heptyl-4-cumylphenol (including isomers), 2,4,6-trimethylphenol, 2,6-dimethyl-4-ethylphenol, 2,6-dimethyl-4-propylphenol (including isomers), 2,6-dimethyl-4-butylphenol (including isomers), 2,6-dimethyl-4-pentylphenol (including isomers), 2,6-dimethyl-4-hexylphenol (including isomers), 2,6-dimethyl-4-phenylphenol, 2,6-dimethyl-4-cumylphenol, 2,4,6-triethylphenol, 2,6-diethyl-4-methylphenol, 2,6-diethyl-4-propylphenol (including isomers), 2,6-diethyl-4-butylphenol (including isomers), 2,6-diethyl-4-pentylphenol (including isomers), 2,6-diethyl-4-hexylphenol (including isomers), 2,6-diethyl-4-phenylphenol (including isomers), 2,6-diethyl-4-cumylphenol, 2,4,6,-tripropylphenol (including isomers), 2,6-dipropyl-4-ethylphenol (including isomers), 2,6-dipropyl-4-methylphenol (including isomers), 2,6-dipropyl-4-butylphenol (including isomers), 2,6-dipropyl-4-pentylphenol (including isomers), 2,6-dipropyl-4-hexylphenol (including isomers), 2,6-dipropyl-4-phenylphenol (including isomers), 2,6-dipropyl-4-cumylphenol (including isomers), 2,4-dimethyl-6-ethylphenol, 2-methyl-4,6-diethylphenol, 2-methyl-4-propyl-6-ethylphenol (including isomers), 2-methyl-4-butyl-6-ethylphenol (including isomers), 2-methyl-4-pentyl-6-ethylphenol (including isomers), 2-methyl-4-hexyl-6-ethylphenol (including isomers), 2-methyl-4-phenyl-6-ethylphenol (including isomers), 2-methyl-4-cumyl-6-ethylphenol (including isomers), 2,4-dimethyl-6-propylphenol (including isomers), 2-methyl-4,6-dipropylphenol (including isomers), 2-methyl-4-ethyl-6-propylphenol (including isomers), 2-methyl-4-butyl-6-propylphenol (including isomers), 2-methyl-4-pentyl-6-propylphenol (including isomers), 2-methyl-4-hexyl-6-propylphenol (including isomers), 2-methyl-4-phenyl-6-propylphenol (including isomers), 2-methyl-4-cumyl-6-propylphenol (including isomers), 2,4-dimethyl-6-butylphenol, 2-methyl-4,6-dibutylphenol (including isomers), 2-methyl-4-propyl-6-butylphenol (including isomers), 2-methyl-4-ethyl-6-butylphenol (including isomers), 2-methyl-4-pentyl-6-butylphenol (including isomers), 2-methyl-4-hexyl-6-butylphenol (including isomers), 2-methyl-4-phenyl-6-butylphenol (including isomers), 2-methyl-4-cumyl-6-butylphenol (including isomers), 2,4-dimethyl-6-pentylphenol, 2-methyl-4,6-dipentylphenol, 2-methyl-4-propyl-6-pentylphenol (including isomers), 2-methyl-4-butyl-6-pentylphenol (including isomers), 2-methyl-4-ethyl-6-pentylphenol (including isomers), 2-methyl-4-hexyl-6-pentylphenol (including isomers), 2-methyl-4-phenyl-6-pentylphenol (including isomers), 2-methyl-4-cumyl-6-pentylphenol (including isomers), 2,4-dimethyl-6-hexylphenol, 2-methyl-4,6-dihexylphenol, 2-methyl-4-propyl-6-hexylphenol (including isomers), 2-methyl-4-butyl-6-hexylphenol (including isomers), 2-methyl-4-pentyl-6-hexylphenol (including isomers), 2-methyl-4-ethyl-6-hexylphenol (including isomers), 2-methyl-4-phenyl-6-hexylphenol (including isomers), 2-methyl-4-cumyl-6-hexylphenol (including isomers), 2-ethyl-4-methyl-6-propylphenol (including isomers), 2,4-diethyl-6-propylphenol (including isomers), 2-ethyl-4,6-propylphenol (including isomers), 2-ethyl-4-butyl-6-propylphenol (including isomers), 2-ethyl-4-pentyl-6-propylphenol (including isomers), 2-ethyl-4-hexyl-6-propylphenol (including isomers), 2-ethyl-4-heptyl-6-propylphenol (including isomers), 2-ethyl-4-octyl-6-propylphenol (including isomers), 2-ethyl-4-phenyl-6-propylphenol (including isomers), 2-ethyl-4-cumyl-6-propylphenol (including isomers), 2-ethyl-4-methyl-6-butylphenol (including isomers), 2,4-diethyl-6-butylphenol (including isomers), 2-ethyl-4,6-butylphenol (including isomers), 2-ethyl-4-propyl-6-butylphenol (including isomers), 2-ethyl-4-pentyl-6-butylphenol (including isomers), 2-ethyl-4-hexyl-6-butylphenol (including isomers), 2-ethyl-4-heptyl-6-butylphenol (including isomers), 2-ethyl-4-octyl-6-butylphenol (including isomers), 2-ethyl-4-phenyl-6-butylphenol (including isomers), 2-ethyl-4-cumyl-6-butylphenol (including isomers), 2-ethyl-4-methyl-6-pentylphenol (including isomers), 2,4-diethyl-6-pentylphenol (including isomers), 2-ethyl-4,6-pentylphenol (including isomers), 2-ethyl-4-butyl-6-pentylphenol (including isomers), 2-ethyl-4-propyl-6-pentylphenol (including isomers), 2-ethyl-4-hexyl-6-pentylphenol (including isomers), 2-ethyl-4-heptyl-6-pentylphenol (including isomers), 2-ethyl-4-octyl-6-pentylphenol (including isomers), 2-ethyl-4-phenyl-6-pentylphenol (including isomers), 2-ethyl-4-cumyl-6-pentylphenol (including isomers), 2-ethyl-4-methyl-6-hexylphenol (including isomers), 2,4-diethyl-6-hexylphenol (including isomers), 2-ethyl-4,6-hexylphenol (including isomers), 2-ethyl-4-propyl-6-hexylphenol (including isomers), 2-ethyl-4-pentyl-6-hexylphenol (including isomers), 2-ethyl-4-butyl-6-hexylphenol (including isomers), 2-ethyl-4-heptyl-6-hexylphenol (including isomers), 2-ethyl-4-octyl-6-hexylphenol (including isomers), 2-ethyl-4-phenyl-6-hexylphenol (including isomers), 2-ethyl-4-cumyl-6-hexylphenol (including isomers), 2-propyl-4-methyl-6-butylphenol (including isomers), 2,4-dipropyl-6-butylphenol (including isomers), 2-propyl-4,6-butylphenol (including isomers), 2-propyl-4-ethyl-6-butylphenol (including isomers), 2-propyl-4-pentyl-6-butylphenol (including isomers), 2-propyl-4-hexyl-6-butylphenol (including isomers), 2-propyl-4-heptyl-6-butylphenol (including isomers), 2-propyl-4-octyl-6-butylphenol (including isomers), 2-propyl-4-phenyl-6-butylphenol (including isomers) and 2-propyl-4-cumyl-6-butylphenol (including isomers). One type of these aromatic hydroxy compounds may be used or a plurality of types may be used in combination.

<Isocyanate Production Process>

In the present embodiment, isocyanates can be produced by using the composition containing the carbamic acid ester and the aromatic hydroxy compound as described above. The following provides an explanation of an isocyanate production process in the present embodiment.

In the isocyanate production process of the present embodiment, the isocyanates can be produced by transferring the composition containing the carbamic acid ester and the aromatic hydroxy compound as described above to a reaction vessel where a thermal decomposition reaction of the carbamic acid ester is carried out. This process is a process for producing isocyanates comprising the following steps (1), (3), (4) and (5) or a process comprising the following steps (2), (3), (4) and (5):

step (1): reacting an amine compound and a carbonic acid ester so as to obtain a mixture containing a carbamic acid ester, an alcohol and a carbonic acid ester;

step (2): reacting an amine compound, an urea and an alcohol so as to obtain a mixture containing a carbamic acid ester, an alcohol and a urea compound;

step (3): separating the alcohol and the carbonic acid ester or the urea contained in the mixture by using the mixture of step (1) or step (2) and the aromatic hydroxyl compound so as to obtain a composition containing the carbamic acid ester and an aromatic hydroxy compound;

step (4): transferring the composition obtained in step (3) in a liquid state to a step (5); and step (5): producing the isocyanate using the composition transferred in step (4).

<Step (1)>

The following provides an explanation of a process for producing carbamic acid ester by a reaction between the carbonic acid ester and the amine compound in step (1).

A carbonic acid ester represented by the following formula (26) can be used for the carbonic acid ester:

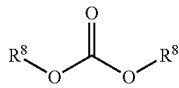
(26)

(wherein $R^8$ represents a linear or branched alkyl group having 1 to 8 carbon atoms).

More preferable examples of $R^8$ in formula (26) above may include linear or branched aliphatic hydrocarbon groups having 1 to 8 carbon atoms, while even more preferable examples may include linear or branched alkyl groups having 1 to 8 carbon atoms. Examples of such $R^8$ may include alkyl groups in the form of aliphatic hydrocarbon groups in which the number of carbon atoms constituting the group is a number selected from the group consisting of integers of 1 to 8, such as a methyl group, an ethyl group, a propyl group (including isomers), a butyl group (including isomers), a pentyl group (including isomers), a hexyl group (including isomers), a heptyl group (including isomers) or an octyl group (including isomers). Examples of such dialkyl carbonates may include dimethyl carbonate, diethyl carbonate, dipropyl carbonate (including isomers), dibutyl carbonate (including isomers), dipentyl carbonate (including isomers), dihexyl carbonate (including isomers), diheptyl carbonate (including isomers) and dioctyl carbonate (including isomers). In particular, dialkyl carbonates in which the number of carbon atoms constituting the alkyl group is a number selected from the group consisting of integers of 4 to 6 are used preferably.

Although the known process can be used to produce the carbonic acid ester, carbonic acid ester is preferably produced by reacting an organic tin compound having a tin-oxygen-carbon bond with carbon dioxide. Namely, the carbonic acid ester can be produced by the following steps:

step (A): (carbonic acid ester formation step) reacting an organic tin compound having a tin-oxygen-carbon bond with carbon dioxide so as to obtain a reaction mixture containing carbonic acid ester; and step (B): (carbonic acid ester separation step) separating the carbonic acid ester from the reaction mixture as well as obtaining a distillation residue.

In addition, the following steps (C) and (D) may be carried out in addition to these steps (A) and (B):

step (C): (organic tin compound regeneration step) reacting with the distillation residue obtained in step (B) with an alcohol so as to form an organic tin compound having a tin-oxygen-carbon bond and a water followed by removing the water from a reaction system; and step (D): (recycling step) reusing the organic tin compound having the tin-oxygen-carbon bond obtained in step (C) as the organic tin compound having the tin-oxygen-carbon bond in step (A).

Dialkyl tin compounds are preferably used for the organic tin compound used in step (A). The term "dialkyl tin compound" refers to an organic tin compound in which two alkyl groups are bonded to a single tin atom.

Examples of these dialkyl tin compounds may include compounds selected from at least one type of compound selected from the group consisting of dialkyl tin compounds represented by the following formula (27) and tetraalkyl distannoxane compounds represented by the following formula (28):

(27)

(wherein each of $R^{13}$ and $R^{14}$ independently represents a linear or branched alkyl group having 1 to 12 carbon atoms, Each of $X^1$ and $X^2$ independently represents at least one type of substituent selected from the group consisting of an alkoxy group, an acyloxyl group and a halogen atom, each of a and b independently represents an integer of 0 to 2, and a+b=2, and each of c and d independently represents an integer of 0 to 2, and c+d=2);

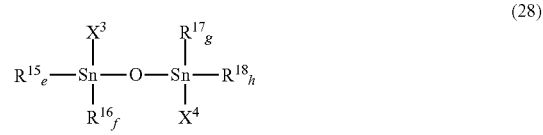
(28)

(wherein each of $R^{15}$, $R^{16}$, $R^{17}$ and $R^{18}$ independently represents a linear or branched alkyl group having 1 to 12 carbon atoms, $X^3$ and $X^4$ represent at least one type of substituent selected from the group consisting of an alkoxy group, an acyloxyl group and a halogen atom, and each of e, f, g and h independently represents an integer of 0 to 2, e+f=2 and g+h=2).

Examples of $R^{13}$ and $R^{14}$ in the dialkyl tin catalyst represented by formula (27) above as well as examples of $R^{15}$, $R^{16}$, $R^{17}$ and $R^{18}$ in the tetraalkyl distannoxane compound represented by formula (28) above may include alkyl groups in the form of aliphatic hydrocarbon groups in which the number of carbon atoms constituting the group is a number selected from the group consisting of integers of 1 to 12, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers) or a dodecyl group (including isomers). More preferable examples may include linear or branched alkyl groups in which the number of carbon atoms constituting the group is a number selected from the group consisting of integers of 1 to 8, and although dialkyl tin compounds can be used in which the alkyl group is an alkyl group in which the number of carbon atoms constituting the group is outside the range indicated above, there are cases in which fluidity may be poor or productivity may be impaired. Moreover, an n-butyl group or n-octyl group is more preferable in consideration of ease of acquisition during industrial production.

$X^1$ and $X^2$ of the dialkyl tin compound represented by formula (27) above and $X^3$ and $X^4$ of the tetraalkyl distannoxane compound represented by formula (28) above represent at least one type of substituent selected from the group consisting of an alkoxy group, an acyloxyl group and a halogen atom, and in the case the group is an alkoxy group and/or an acyloxy group, the number of carbon atoms constituting the group is preferably a number selected from the group consisting of integers of 0 to 12. Examples of such groups may include alkoxy groups composed of a linear or branched saturated alkyl group and an oxygen atom, such as a methoxy group, an ethoxy group, a propoxy group (including isomers), a butoxy group (including isomers), a pentyloxy group (including isomers), a hexyloxy group (including isomers), a heptyloxy group (including isomers), an octyloxy group (including isomers), a nonyloxy group (including isomers) or a decyloxy group (including isomers); an acyloxy groups composed of a linear or branched saturated alkyl group, a carbonyl group and an oxygen atom, such as an acetoxy group, a propionyloxy group, a butyryloxy group, a valeryloxy group or a lauryloxy group; and halogen atoms such as a chloro group or bromo group. More preferable examples may include alkoxy groups having 4 to 6 carbon atoms in consideration of fluidity and solubility as well as use of the carbonic acid ester as a production catalyst.

Examples of dialkyl tin compounds represented by formula (27) may include dialkyl-dialkoxy tins such as dimethyl-dimethoxy tin, dimethyl-diethoxy tin, dimethyl-dipropoxy tin (including isomers), dimethyl-dibutoxy tin (including isomers), dimethyl-dipentyloxy tin (including isomers), dimethyl-dihexyloxy tin (including isomers), dimethyl-diheptyloxy tin (including isomers), dimethyl-dioctyloxy tin (including isomers), dimethyl-dinonyloxy tin (including isomers), dimethyl-didecyloxy tin (including isomers), dibutyl-dimethoxy tin (including isomers), dibutyl-diethoxy tin (including isomers), dibutyl-dipropoxy tin (including isomers), dibutyl-dibutyloxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dibutyl-dinonyloxy tin (including isomers), dibutyl-didecyloxy tin (including isomers), dioctyl-dimethoxy tin (including isomers), dioctyl-diethoxy tin (including isomers), dioctyl-dipropoxy tin (including isomers), dioctyl-dibutyloxy tin (including isomers), dioctyl-dipentyloxy tin (including isomers), dioctyl-dihexyloxy tin (including isomers), dioctyl-diheptyloxy tin (including isomers), dioctyl-dioctyloxy tin (including isomers), dioctyl-dinonyloxy tin (including isomers) or dioctyl-didecyloxy tin (including isomers); dialkyl-diacyloxy tins such as dimethyl-diacetoxy tin, dimethyl-dipropionyloxy tin (including isomers), dimethyl-dibutyryloxy tin (including isomers), dimethyl-divaleryloxy tin (including isomers), dimethyl-dilauroyloxy tin (including isomers), dibutyl-diacetoxy tin (including isomers), dibutyl-dipropionyloxy tin (including isomers), dibutyl-dibutyryloxy tin (including isomers), dibutyl-divaleryloxy tin (including isomers), dibutyl-dilauroyloxy tin (including isomers), dioctyl-diacetoxy tin (including isomers), dioctyl-dipropionyloxy tin (including isomers), dioctyl-dibutyryloxy tin (including isomers), dioctyl-divaleryloxy tin (including isomers) or dioctyl-dilauroyloxy tin (including isomers); and, dialkyl-dihalide tins such as dimethyl-dichloro tin, dimethyl-dibromo tin, dibutyl-dichloro tin (including isomers), dibutyl-dibromo tin (including isomers), dioctyl-dichloro tin (including isomers) or dioctyl-dibromo tin (including isomers).

Among these, dialkyl tin dialkoxides such as dimethyl-dimethoxy tin, dimethyl-diethoxy tin, dimethyl-dipropoxy tin (including isomers), dimethyl-dibutoxy tin (including isomers), dimethyl-dipentyloxy tin (including isomers), dimethyl-dihexyloxy tin (including isomers), dimethyl-diheptyloxy tin (including isomers), dimethyl-dioctyloxy tin (including isomers), dimethyl-dinonyloxy tin (including isomers), dimethyl-didecyloxy tin (including isomers), dibutyl-dimethoxy tin (including isomers), dibutyl-diethoxy tin (including isomers), dibutyl-dipropoxy tin (including isomers), dibutyl-dibutyloxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dibutyl-dinonyloxy tin (including isomers), dibutyl-didecyloxy tin (including isomers), dioctyl-dimethoxy tin (including isomers), dioctyl-diethoxy tin (including isomers), dioctyl-dipropoxy tin (including isomers), dioctyl-dibutyloxy tin (including isomers), dioctyl-dipentyloxy tin (including isomers), dioctyl-dihexyloxy tin (including isomers), dioctyl-diheptyloxy tin (including isomers), dioctyl-dioctyloxy tin (including isomers), dioctyl-dinonyloxy tin (including isomers) or dioctyl-didecyloxy tin (including isomers) are preferable, dialkyl-dialkoxy tins such as dibutyl-dipropoxy tin (including isomers), dibutyl-dibutyryloxy tin (including isomers), dibutyl-dipentyloxy tin (including isomers), dibutyl-dihexyloxy tin (including isomers), dibutyl-diheptyloxy tin (including isomers), dioctyl-dipropoxy tin (including isomers), dioctyl-dibutoxy tin (including isomers), dioctyl-dipentyloxy tin (including isomers), dioctyl-dihexyloxy tin (including isomers) or dioctyl-diheptyloxy tin (including isomers) are more preferable, and dibutyl-dibutyloxy tin (including isomers), dibutyl-dipentyloxy tin (including isomers), dibutyl-dihexyloxy tin (including isomers), dibutyl-diheptyloxy tin (including isomers), dibutyl-dioctyloxy tin (including isomers), dioctyl-dibutyloxy tin (including isomers), dioctyl-dipentyloxy tin (including isomers), dioctyl-dihexyloxy tin (including isomers), dioctyl-diheptyloxy tin (including isomers) or dioctyl-dioctyloxy tin (including isomers) is even more preferable.

Although the dialkyl tin compound represented by the formula (27) has a monomer structure, this may be a polymer structure or associate.

Examples of the tetraalkyl dialkoxy distannoxane represented by the formula (28) may include 1,1,3,3-tetraalkyl-1,3-dialkoxy distannoxanes such as 1,1,3,3-tetramethyl-1,3-dimethoxy distannoxane, 1,1,3,3-tetramethyl-1,3-diethoxy distannoxane, 1,1,3,3-tetramethyl-1,3-dipropoxy distannoxane (including isomers), 1,1,3,3-tetramethyl-1,3-dibutoxy distannoxane (including isomers), 1,1,3,3-tetramethyl-1,3-dipentyloxy distannoxane (including isomers), 1,1,3,3-tetramethyl-1,3-dihexyloxy distannoxane (including isomers), 1,1,3,3-tetramethyl-1,3-diheptyloxy distannoxane (including isomers), 1,1,3,3-tetramethyl-1,3-dioctyloxy distannoxane (including isomers), 1,1,3,3-tetramethyl-1,3-dinonyloxy distannoxane (including isomers), 1,1,3,3-tetramethyl-1,3-didecyloxy distannoxane (including isomers), 1,1,3,3-tetrabutyl-1,3-dimethoxy distannoxane (including isomers), 1,1,3,3-tetrabutyl-1,3-diethoxy distannoxane (including isomers), 1,1,3,3-tetrabutyl-1,3-dipropoxy distannoxane (including isomers), 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetrabutyl-1,3-dinonyloxy distannoxane (including isomers), 1,1,3,3-tetrabutyl-1,3-didecyloxy distannoxane (including isomers), 1,1,3,3-tetraoctyl-1,3-dimethoxy distannoxane (including isomers), 1,1,3,3-tetraocyl-1,3-diethoxy distannoxane (including isomers), 1,1,3,3-tetraoctyl-1,3-dipropoxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers), 1,1,3,3-tetraoctyl-1,3-dioctyloxy distannoxane (including isomers), 1,1,3,3-tetraoctyl-1,3-dinonyloxy distannoxane (including isomers) or 1,1,3,3-tetraoctyl-1,3-didecyloxy distannoxane (including isomers); 1,1,3,3-tetraalkyl-1,3-diacyloxy distannoxanes such as 1,1,3,3-tetramethyl-1,3-diacetoxy distannoxane, 1,1,3,3-tetramethyl-1,3-dipropionyloxy distannoxane (including isomers), 1,1,3,3-tetramethyl-1,3-dibutyryloxy distannoxane (including isomers), 1,1,3,3-tetramethyl-1,3-divaleryloxy distannoxane (including isomers), 1,1,3,3-tetramethyl-1,3-dilauroyloxy distannoxane (including isomers), 1,1,3,3-tetrabutyl-1,3-diacetoxy distannoxane (including isomers), 1,1,3,3-tetrabutyl-1,3-dipropionyloxy distannoxane (including isomers), 1,1,3,3-tetrabutyl-1,3-dibutyryloxy distannoxane (including isomers), 1,1,3,3-tetrabutyl-1,3-divaleryloxy distannoxane (including isomers), 1,1,3,3-tetrabutyl-1,3-dilauroyloxy distannoxane (including isomers), 1,1,3,3-tetraoctyl-1,3-diacetoxy distannoxane (including isomers), 1,1,3,3-tetraoctyl-1,3-dipropionyloxy distannoxane (including isomers), 1,1,3,3-tetraoctyl-1,3-dibutyryloxy distannoxane (including isomers), 1,1,3,3-tetraoctyl-1,3-divaleryloxy distannoxane (including isomers) or 1,1,3,3-tetraoctyl-1,3-dilauroyloxy distannoxane (including isomers); and, 1,1,3,3-tetraalkyl-1,3-dihalide distannoxanes such as 1,1,3,3-tetramethyl-1,3-dichloro distannoxane, 1,1,3,3-tetramethyl-1,3-dibromo distannoxane, 1,1,3,3-tetrabutyl-1,3-dichloro distannoxane (including isomers), 1,1,3,3-tetrabutyl-1,3-dibromo distannoxane (including isomers), 1,1,3,3-tetraocyl-1,3-dichloro distannoxane (including isomers) or 1,1,3,3-tetraocyl-1,3-dibromo distannoxane (including isomers).

Among these, 1,1,3,3-tetraalkyl-1,3-dialkoxy distannoxanes such as 1,1,3,3-tetramethyl-1,3-dimethoxy distannoxane, 1,1,3,3-tetramethyl-1,3-diethoxy distannoxane, 1,1,3,3-tetramethyl-1,3-dipropoxy distannoxane (including isomers), 1,1,3,3-tetramethyl-1,3-dibutoxy distannoxane (including isomers), 1,1,3,3-tetramethyl-1,3-dipentyloxy distannoxane (including isomers), 1,1,3,3-tetramethyl-1,3-dihexyloxy distannoxane (including isomers), 1,1,3,3-tetramethyl-1,3-diheptyloxy distannoxane (including isomers), 1,1,3,3-tetramethyl-1,3-dioctyloxy distannoxane (including isomers), 1,1,3,3-tetramethyl-1,3-dinonyloxy distannoxane (including isomers), 1,1,3,3-tetramethyl-1,3-didecyloxy distannoxane (including isomers), 1,1,3,3-tetrabutyl-1,3-dimethoxy distannoxane (including isomers), 1,1,3,3-tetrabutyl-1,3-diethoxydistannoxane (including isomers), 1,1,3,3-tetrabutyl-1,3-dipropoxy distannoxane (including isomers), 1,1,3,3-tetrabutyl-1,3-dibutoxy distannoxane (including isomers), 1,1,3,3-tetrabutyl-1,3-dipentyloxy-distannoxane (including isomers), 1,1,3,3-tetrabutyl-1,3-dihexyloxy distannoxane (including isomers), 1,1,3,3-tetrabutyl-1,3-diheptyloxy distannoxane (including isomers), 1,1,3,3-tetrabutyl-1,3-dioctyloxy distannoxane (including isomers), 1,1,3,3-tetrabutyl-1,3-dinonyloxy distannoxane (including isomers), 1,1,3,3-tetrabutyl-1,3-didecyloxy distannoxane (including isomers), 1,1,3,3-tetraoctyl-1,3-dimethoxy distannoxane (including isomers), 1,1,3,3-tetraoctyl-1,3-diethoxy distannoxane (including isomers), 1,1,3,3-tetraoctyl-1,3-dipropoxy distannoxane (including isomers), 1,1,3,3-tetraoctyl-1,3-dibutoxy distannoxane (including isomers), 1,1,3,3-tetraoctyl-1,3-dipentyloxy distannoxane (including isomers), 1,1,3,3-tetraoctyl-1,3-dihexyloxy distannoxane (including isomers), 1,1,3,3-tetraoctyl-1,3-diheptyloxy distannoxane (including isomers), 1,1,3,3-tetraoctyl-1,3-dioctyloxy distannoxane (including isomers), 1,1,3,3-tetraoctyl-1,3-dinonyloxy distannoxane (including isomers) or 1,1,3,3-tetraoctyl-1,3-didecyloxy distannoxane (including isomers) are preferable, and 1,1,3,3-tetrabutyl-1,3-dibutoxy distannoxane (including isomers), 1,1,3,3-tetrabutyl-1,3-dipentyloxy distannoxane (including isomers), 1,1,3,3-tetrabutyl-1,3-dihexyloxy distannoxane (including isomers), 1,1,3,3-tetrabutyl-1,3-diheptyloxydistannoxane (including isomers), 1,1,3,3-tetrabutyl-1,3-dioctyloxy distannoxane (including isomers), 1,1,3,3-tetraoctyl-1,3-dibutoxy distannoxane (including isomers), 1,1,3,3-tetraoctyl-1,3-dipentyloxydistannoxane (including isomers), 1,1,3,3-tetraoctyl-1,3-dihexyloxydistannoxane (including isomers), 1,1,3,3-tetraoctyl-1,3-diheptyloxy distannoxane (including isomers) or 1,1,3,3-tetraoctyl-1,3-dioctyloxy distannoxane (including isomers) is more preferable.

Although the tetraalkyl dialkoxy distannoxane represented by formula (28) has a monomer structure, this may be a polymer structure or associate.

In general, organic tin compounds easily take an associated structure, and although, for example, dialkyl tin dialkoxy tin is known to form a dimer structure, and tetraalkyl dialkoxy distannoxanes are known to be present by forming a ladder structure in which two or three molecules are associated, even in cases in which there are changes in this associated state, the representation of a compound in the form of a monomer structure is common for a person with ordinary skill in the art.

In addition, the previously indicated dialkyl tin alkoxide compound may be used alone or two or more types may be used as a mixture.

A previously disclosed production process (such as that disclosed in WO 2005/111049) can preferably be used as the process for producing the dialkyl tin compound. This process is a process for producing a dialkyl tin compound from a dialkyl tin oxide and an alcohol.

Examples of alcohols used in the present embodiment may include alcohols such as methanol, ethanol, propanol (including isomers), butanol (including isomers), pentanol (including isomers), hexanol (including isomers), heptanol (including isomers), octanol (including isomers), nonanol (including isomers) or decanol (including isomers), and an alcohol is preferably used in which the number of carbon atoms constituting the alcohol is a number selected from the group consisting of integers of 1 to 12.

Dialkyl tin oxides represented by the following formula (29) are used for the dialkyl tin oxide used in the alkyl tin alkoxide synthesis process:

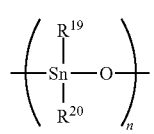

(29)

(wherein each of $R^{19}$ and $R^{20}$ independently represents a linear or branched alkyl group having 1 to 12 carbon atoms).

Examples of $R^{19}$ and $R^{20}$ may include alkyl groups in the form of aliphatic hydrocarbon groups having 1 to 12 carbon atoms, such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), an undecyl group (including isomers) or a dodecyl group (including isomers). More preferable examples may include linear or branched saturated alkyl groups having 1 to 8 carbon atoms. Even more preferable examples may include a n-butyl group and a n-octyl group.

A tetraalkyl dialkoxy distannoxane and/or dialkyl tin dialkoxide is obtained by a dehydration reaction of the alcohol and the dialkyl tin oxide while removing the water formed from the system. The temperature at which the reaction is carried out is, for example, within the range of from 80 to 180° C., and in order to distill off the water formed from the system, although varying according to the reaction pressure, a temperature of from 100 to 180° C. is preferable. Although a high temperature is preferable for the reaction temperature to accelerate the reaction rate, since undesirable reactions such as decomposition also occur at high temperatures thereby decreasing yield, the reaction temperature is more preferably within the range of from 100 to 160° C. The reaction pressure is a pressure that allows water formed to be removed from the system, and the reaction is carried out at a pressure of from 20 to $1 \times 10^6$ Pa, although varying according to the reaction temperature. There are no particular limitations on the reaction time of the dehydration reaction, and is generally from 0.001 to 50 hours, preferably from 0.01 to 10 hours and more preferably from 0.1 to 2 hours. The reaction may be terminated once the desired alkyl tin alkoxide composition has been obtained.

Progression of the reaction is also determined by measuring the amount of water extracted outside the system, and can also be determined by a method using $^{119}$Sn-NMR by sampling the reaction liquid. In order to produce the mixture of the present embodiment in step 1, the reaction is terminated after confirming the obtaining of a composition in which the molar ratio of tetraalkyl dialkoxy distannoxane and dialkyl tin dialkoxide contained in the alkyl tin alkoxide composition obtained in the above reaction, when expressed as the combined molar ratio of both, is within the range of from 0:100 to 80:20 and more preferably within the range of from 10:90 to 70:30. The alcohol used may be used while still present in the reaction system, and the alcohol may also be used by distilling off the alcohol depending on the case. Since there is the advantage of being able to reduce the size of the reaction vessels of the other steps, it is preferable to remove as much of the alcohol as possible. Removal by known distillation is preferable for the removal method, and known distillation equipment can be used for the distiller used for distillation. A thin film distillation apparatus is preferably used for the distillation apparatus since the alcohol can be removed in a short period of time. There are no particular limitations on the type of reaction vessel of the dehydration reaction, and the known tank type or the column type reaction vessel can be used. A low boiling point reaction mixture containing water is extracted in gaseous form from the reaction vessel by distillation, while a high boiling point reaction mixture containing a produced alkyl tin alkoxide or alkyl tin alkoxide mixture is extracted in the form of a liquid from the lower portion of the reaction vessel. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film distillation apparatus, a reactor provided with a support inside, a forced circulation reactor, a falling film evaporator, a falling drop evaporator, a trickle flow reactor or a bubble column, and types using combinations thereof. Methods using a columnar reactor are preferable from the viewpoint of efficiently shifting the equilibrium to the products side, while a structure having a large gas-liquid contact area is preferable for being able to rapidly transfer the water formed to the gaseous phase. Although continuous methods using a multitubular reactor, a multistage distillation column or a packed column packed with a packing can also be used, since the dialkyl tin oxide used in this step is generally a solid, it is preferable to employ a method in which the reaction is first carried out in a tank-type reaction vessel followed by increasing the content of dialkyl tin dialkoxide in a column-type reaction vessel. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, the known method such as steam or a heater may be used for heating, and the known method such as air cooling, cooling water or brine can be used for cooling.

Step (A) is a step for producing the carbonic acid esters by reacting the dialkyl tin compounds produced according to the process described above with gaseous carbon dioxide. A previously disclosed carbonic acid ester production process (such as that disclosed in WO 03/055840 or WO 04/014840) is preferably used in this step.

The alkyl tin compound supplied to this step may be supplied from an alkyl tin alkoxide synthesis step at the start of production, or from a dialkyl tin compound production step of step (C) to be described later during continuous production.

In this step, the above-mentioned dialkyl tin alkoxide and gaseous carbon dioxide are absorbed and undergo a chemical reaction to obtain a mixture containing a carbon dioxide-bonded form of the dialkyl tin alkoxide.

During this chemical reaction, the dialkyl tin alkoxide is reacted in liquid form. The dialkyl tin alkoxide is preferably put into liquid form by heating. In addition, it may also be put into liquid form by a solvent and the like. Although varying according to the reaction temperature, the reaction pressure is preferably within the range of from a normal pressure to 1 MPa, more preferably within the range of from the normal pressure to 0.6 MPa. Although varying according to the reaction pressure, the reaction temperature is preferably within the range of from −40 to 80° C., and in consideration of fluidity during transfer, more preferably from 0 to 80° C. and even more preferably within the range of from a normal temperature (e.g., 20° C.) to 80° C. The reaction time may be within the range of from several seconds to 100 hours, and in consideration of productivity and the like, is preferably from several minutes to 10 hours. A known tank type reaction vessel or a column type reaction vessel can be used for the reaction vessel. In addition, a plurality of reaction vessels may be used in combination. Since the reaction is a reaction between carbon dioxide gas (gas) and an alkyl tin alkoxide composition (liquid), in order to carry out the reaction efficiently, it is preferable to increase the contact surface area between the gas and liquid by increasing the gas-liquid interface. Known findings can be used for the method for reacting while increasing the gas-liquid interface in this manner, and examples of preferable methods thereof may include increasing the stirring speed or generating bubbles in the liquid in the case of a tank type reaction vessel, and using a packed column or using a plate column in the case of a column type reaction vessel. Examples of such column type reaction vessels may include plate column types using a tray such as a bubble tray, a porous plate tray, a valve tray or a counter-current tray, and packed column types packed with various types of packing materials such as a raschig ring, a lessing ring, a pole ring, a Berl saddle, an Interlock saddle, a Dixon packing, a McMahon packing, Helipack, a Sulzer packing or Mellapak. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, pump or a condenser and the like may be added as necessary, the known method such as steam or a heater may be used for heating, and the known method such as air cooling, cooling water or brine can be used for cooling. Since the reaction is generally an exothermic reaction, the reaction vessel may be cooled or it may be cooled by dissipation of heat there from. Alternatively, the reaction vessel may also be heated if the purpose is combining with a carbonic acid esterification reaction. A known method such as a method using a heat jacket or a method using an internal coil can be used to heat and cool the reaction vessel. The carbon dioxide gas and alkyl tin alkoxide composition supplied to the reaction vessel may be supplied separately to the reaction vessel or they may be mixed prior to supplying to the reaction vessel. These components may also be supplied from a plurality of locations in the reaction vessel. Completion of the reaction can be determined by, for example, $^{119}$Sn-NMR analysis.

Next, the reaction liquid containing carbonic acid ester is obtained from the carbon dioxide associate of dialkyl tin alkoxide obtained in the above manner according to the method described below.

Although the reaction temperature is within the range of from 110 to 200° C., and a high temperature is preferable for the reaction temperature in order to accelerate the reaction rate, since undesirable reactions such as decomposition also occur at high temperatures thereby decreasing yield, the reaction temperature is more preferably within the range of from 120 to 180° C., the reaction time is preferably within the range of from 0.1 to 10 hours, and the reaction pressure is from 1.5 to 20 MPa and preferably from 2.0 to 10 MPa. The reaction is terminated after the desired carbonic acid ester has formed in the reaction vessel. Progression of the reaction can be confirmed by, for example, sampling the reaction liquid in the reaction vessel, and analyzing the carbonic acid ester formed by a method such as $^{1}$H-NMR or gas chromatography. For example, the reaction may be terminated after the carbonic acid ester has been formed at a molar ratio of 10% or more of the dialkyl tin alkoxide and/or carbon dioxide associate of the dialkyl tin alkoxide contained in the dialkyl tin alkoxide and/or carbon dioxide associate of the dialkyl tin alkoxide, and in the case of desiring to increase the yield of the carbonic acid ester, the reaction may be terminated after allowing to continue until the value reaches 90% or more. A known reaction vessel can be used for the reaction vessel, and a column type reaction vessel or a tank type reaction vessel can be used preferably. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Step (B) in the present embodiment is a step for obtaining a distillation residue from the reaction liquid containing carbonic acid ester obtained in step (A) above by separating the carbonic acid ester. A known method or apparatus can be preferably used for the separation method, and a preferable method is distillation.

Carbonic acid ester and distillation residue are obtained by batch, semi-batch or continuous distillation of the reaction liquid transferred from step (A) above. A preferable example of the distillation method may include supplying the reaction liquid to a distiller, separating the carbonic acid ester in the form of a gaseous phase component from a top of the distiller outside the system, and extracting the distillation residue in the form of a liquid component from the bottom of the distiller. Although varying according to the boiling point and pressure of the carbonic acid ester, the temperature in this step is within the range of from a normal temperature (e.g., 20° C.) to 200° C., and since there are cases in which denaturation of tin compounds in the distillation residue may occur or the amount of carbonic acid ester may decrease due to a reverse reaction at high temperatures, the reaction temperature is preferably within the range of from the normal temperature (e.g. 20° C.) to 150° C. Although varying according to the type of carbonic acid ester and temperature at which the reaction is carried out, the reaction is generally carried out at normal pressure to reduced pressure conditions, and in consideration of productivity, the pressure is more preferably within the range of from 100 Pa to 80 KPa and most preferably within the range of from 100 Pa to 50 KPa. The reaction can be carried out a reaction time within the range of from 0.01 to 10 hours, and since there are cases in which tin compounds contained in the reaction liquid are denatured and cases in which the amount of carbonic acid ester decreases due to a reverse reaction when the reaction is carried out for a long period of time at high temperatures, the reaction time is preferably within the range of from 0.01 to 0.5 hours and most preferably within the range of from 0.01 to 0.3 hours. A known distiller can be used for the distiller, a column type distiller or a tank type distiller can be used preferably, or a plurality of types can be used in combination. More preferable examples of the distillers may include a thin film distillation apparatus and a thin film distiller, and a thin film distillation apparatus provided with a distillation column or a thin film distiller is most preferable. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

Although the above has indicated a production example of the carbonic acid ester using the dialkyl tin compound, the following steps (C) and (D) can be carried out in addition to the above-mentioned steps (A) and (B).

Step (C) is a step for regenerating a dialkyl tin compound by reacting the distillation residue obtained in step (B) with an alcohol.

Examples of alcohols used in this step may include alcohols such as methanol, ethanol, propanol (including isomers), butanol (including isomers), pentanol (including isomers), hexanol (including isomers), heptanol (including isomers), octanol (including isomers), nonanol (including isomers) or decanol (including isomers), and although an alcohol is preferably used in which the number of carbon atoms constituting the alcohol is a number selected from the group consisting of integers of 1 to 12, more preferably an alcohol is used that is the same alcohol as the alcohol used in the alkyl tin alkoxide synthesis step above.

The conditions of the dehydration reaction are preferably the same as the conditions of the above-mentioned alkyl tin alkoxide synthesis step. The reaction may be terminated once the desired alkyl tin alkoxide composition has been obtained. Progression of the reaction is also determined by measuring the amount of water extracted outside the system, and can also be determined by a method using $^{119}$Sn-NMR by sampling the reaction liquid. In order to produce the mixture of the present embodiment in step 1, the reaction is terminated after confirming the obtaining of a composition in which the molar ratio of tetraalkyl dialkoxy distannoxane and dialkyl tin dialkoxide contained in the alkyl tin alkoxide composition obtained in the above reaction, when expressed as the combined molar ratio of both, is within the range of from 0:100 to 80:20 and more preferably within the range of from 10:90 to 70:30. The alcohol used may be used while still present in the reaction system, and the alcohol may also be used by distilling off the alcohol depending on the case.

Since there is the advantage of being able to reduce the size of the reaction vessels of the other steps, it is preferable to remove as much of the alcohol as possible. Removal by known distillation is preferable for the removal method, and known distillation equipment can be used for the distiller used for distillation. A thin film distillation apparatus is preferably used for the distillation apparatus since the alcohol can be removed in a short period of time. Differing from the alkyl tin alkoxide synthesis step, since dialkyl tin oxide normally in a solid state is not used in this step, there are few restrictions on the reaction vessel. Namely, there are no particular limitations on the type of reaction vessel of the dehydration reaction, and a known tank type or a column type reaction vessel can be used. A low boiling point reaction mixture containing water is extracted in gaseous form from the reaction vessel by distillation, while a high boiling point reaction mixture containing a produced alkyl tin alkoxide or alkyl tin alkoxide mixture is extracted in the form of a liquid from the lower portion of the reaction vessel. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a columnar reactor are preferable from the viewpoint of efficiently shifting the equilibrium to the products side, while a structure having a large gas-liquid contact area is preferable for being able to rapidly transfer the water formed to the gaseous phase. Continuous methods using a multitubular reactor, a multistage distillation column or a packed column packed with a packing are particularly preferable. Although known materials may be used for the materials of the reaction vessel and lines provided they do not have a detrimental effect, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling.

A dialkyl tin compound produced in step (C) above is reused as the dialkyl tin compound used in step (A) as a result of carrying out the following step (D).

On the other hand, the amine compounds represented by the following formula (30) are preferably used for the amine compounds used in step (1).

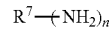

(30)

(wherein $R^7$ represents a group selected from the group consisting of an aliphatic group having 1 to 20 carbon atoms and an aromatic group having 6 to 20 carbon atoms, the above groups containing an atom selected from carbon and oxygen atoms, and having a valence equal to n, and n represents an integer of 2 to 10).

In formula (30) above, a polyamine in which n is 2 or more is used preferably, and a diamine compound in which n is 2 is used more preferably.

In formula (30) above, $R^7$ preferably represents a group previously explained.

Examples of such polyamine compounds may include aliphatic diamines such as hexamethylene diamine, 4,4'-methylenebis(cyclohexylamine) (including isomers), cyclohexane diamine (including isomers) or 3-aminomethyl-3,5,5-trimethylcyclohexyl amine (including isomers); and aromatic diamines such as phenylene diamine (including isomers), toluene diamine (including isomers) or 4,4'-methylene dianiline. Among these, aliphatic diamines such as hexamethylene diamine, 4,4'-methylenebis(cyclohexylamine) (including isomers), cyclohexane diamine (including isomers) or 3-aminomethyl-3,5,5-trimethylcyclohexyl amine (including isomers) are used preferably, hexamethylene diamine, 4,4'-methylenebis(cyclohexylamine) and 3-aminomethyl-3,5,5-trimethylcyclohexyl amine are used more preferably.

Reaction conditions under which the reaction of step (1) is carried out vary according to the reacted compounds, and although dialkyl carbonate is preferably in excess with respect to the amino groups of the amine compound to accelerate the reaction rate and complete the reaction quickly at a stoichiometric ratio of the dialkyl carbonate to amino groups of the amine compound within a range of from 2 to 1000 times, the range is preferably from 2 to 100 times, and more preferably from 2.5 to 30 times in consideration of the size of the reaction vessel. The reaction temperature is generally within the range of from a normal temperature (20° C.) to 300° C., and although higher temperatures are preferable in order to accelerate the reaction rate, since undesirable reactions may conversely occur at high temperatures, the reaction temperature is preferably within the range of from 50 to 150° C. A known cooling apparatus or heating apparatus may be installed in the reaction vessel to maintain a constant reaction temperature. In addition, although varying according to the types of compounds used and reaction temperature, the reaction pressure may be a decreased pressure, a normal pressure or an increased pressure, and the reaction is generally carried out at a pressure within the range of from 20 to $1\times10^6$ Pa. There are no particular limitations on the reaction time (residence time in the case of a continuous method), and is generally from 0.001 to 50 hours, preferably from 0.01 to 10 hours and more preferably from 0.1 to 5 hours. In addition, the reaction can also be terminated by confirming that a desired amount of alkyl carbamate has been formed by, for example, liquid chromatography after sampling the reaction liquid. In the present embodiment, a catalyst can be used as necessary, and examples of catalysts that can be used may include organic metal compounds and inorganic metal compounds of tin, lead, copper or titanium, and basic catalysts such as alkylates of alkaline metals or alkaline earth metals in the form of methylates, ethylates and butyrates (including isomers) of lithium, sodium, potassium, calcium or barium.

Although the use of a reaction solvent is not necessarily required in the present embodiment, a suitable inert solvent is preferably used as a reaction solvent for the purpose of facilitating the reaction procedure, examples of which may include alkanes such as hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as diphenyl ether or diphenyl sulfide; and sulfoxides such as dimethylsulfoxide or diphenylsulfoxide. These solvents can be used alone or two or more types can be used as a mixture. In addition, the dialkyl carbonate used in excess with respect to amino groups of the amine compound is also preferably used as a solvent in the reaction.

A known tank type reaction vessel, a column type reaction vessel or a distillation column can be used for the reaction vessel, and although known materials may be used for the reaction vessel and lines provided they do not have a detrimental effect on the starting substances or reactants, SUS304, SUS316 or SUS316L and the like can be used preferably since they are inexpensive.

According to step (1), the reaction mixture is obtained containing carbamic acid ester, an excess of carbonic acid ester, and alcohol formed as a by-product of the reaction. The alcohol in the mixture is an alcohol having an alkyl group derived from the carbonic acid ester used in step (1).

<Step (2)>

The following provides an explanation of a process for producing a carbamic acid ester by a reaction between urea, an alcohol and an amine compound of step (2).

Alcohols represented by the following formula (31) can be used for the alcohol.

$$R^9\text{—OH} \qquad (31)$$

(wherein $R^9$ represents a linear or branched alkyl group having 1 to 10 carbon atoms).

Examples of $R^9$ in formula (31) above may include a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers) and a decyl group (including isomers).

A previously described amine compound can be used for the amine compound.

Although reaction conditions vary according to the reacted compounds, the stoichiometric ratio of the amount of alcohol to the amino groups of the amine compound used is within the range of from 1 to 500 times. Although it is preferable to use an excess amount of alcohol since complex substituted urea compounds are formed easily if the amount of alcohol used is less than 1 times the amino groups of the amine compound, in consideration of the size of the reaction vessel, the amount of alcohol used is preferably within the range of from 1 to 100 times and more preferably within the range of from 5 to 50 times. The stoichiometric ratio of the amount of urea to the amino groups of the polyamine compound is within the range of from 0.5 to 3 times. Although it is preferable to use an excess amount of urea since complex substituted urea compounds are formed easily if the amount of alcohol used is less than 0.5 times the amino groups of the amine compound, since complex substituted urea compounds form easily or unreacted urea remains even in cases of using an excess amount of urea, the amount of urea used is preferably within the range of from 0.8 to 2 times. The reaction temperature is preferably within the range of from 150 to 280° C. Since the alcohol and the amine compound, urea and by-product ammonia bond strongly at temperatures lower than 150° C., the reaction slows or hardly occurs at all, or complex substituted urea compounds increase, thereby making this undesirable. On the other hand, the urea decomposes, the alcohol is dehydrogenated and denatured, or decomposition, denaturation and so forth of the product in the form of polycarbamic acid ester occurs easily at temperatures higher than 280° C., thereby making this undesirable. In this sense, the reaction temperature is more preferably within the range of from 180 to 260° C. and even more preferably within the range of from 200 to 250° C.

Since the reaction is an equilibrium reaction and the reaction is biased towards the reactants side, it is preferable to carry out the reaction while removing the by-product ammonia outside the system. Examples of methods thereof may include reactive distillation, use of an inert gas, membrane separation and adsorptive separation. For example, reactive distillation refers to a method for separating ammonia continuously formed as a by-product during the reaction by distillation in the form of a gas. This can be carried out in the presence of a solvent or while boiling a hydroxy compound in order to increase the distillation efficiency of the ammonia. In addition, a method using an inert gas refers to a method for separating ammonia continuously formed as a by-product during the reaction from the reaction system in the form of a gas along with the inert gas. Examples of inert gases used may include nitrogen, helium, argon, carbon dioxide, methane, ethane and propane, these may be used alone or as a mixture, and a method in which the inert gas is introduced into the reaction system is preferable. Examples of adsorbents used in methods using adsorptive separation may include adsorbents able to be used under the temperature conditions at which the reaction is carried out, such as silica, alumina, various types of zeolite or diatomaceous earth. These methods for removing ammonia outside the system may be carried out alone or a plurality of types may be carried out in combination.

A catalyst can be used in the reaction for the purpose of increasing the reaction rate. Examples of catalysts that are used preferably may include basic catalysts such as methylates, ethylates or butyrates (including isomers) of lithium, sodium, potassium, calcium or barium, rare earth elements, antimony or bismuth alone or oxides, sulfides and salts thereof, boron alone or boron compounds, metals of the copper family, zinc family, aluminum family, carbon family and titanium family in the periodic table as well as metal oxides and sulfides thereof, and carbides and nitrides of elements of the carbon family excluding carbon, titanium family, vanadium family and chromium family in the periodic table. Although there are no particular limitations on the amount of catalyst used in the case of using a catalyst, a catalyst can be used within the range of a stoichiometric ratio of from 0.0001 to 100 times the amino groups of the amine compound.

Although the reaction pressure varies according to the composition of the reaction system, reaction temperature, ammonia removal method, reaction apparatus and the like, generally the reaction is preferably carried out within the range of from 0.01 to 10 MPa, and preferably within the range of from 0.1 to 5 MPa in consideration of ease of industrial application. Although varying according to the composition of the reaction system, reaction temperature, ammonia removal method, reaction apparatus and reaction pressure and the like, the reaction time is generally from 0.01 to 100 hours.

Although the use of a reaction solvent is not necessarily required in the present embodiment, a suitable inert solvent is preferably used as a reaction solvent for the purpose of facilitating the reaction procedure, examples of which may include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; nitrile compounds such as acetonitrile or benzonitrile; alcohols such as methanol, ethanol, propanol (including isomers), butanol (including isomers), pentanol (including isomers), hexanol (including isomers), heptanol (including isomers), octanol (including isomers) or nonanol (including isomers); aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aromatic hydroxy compounds such as phenol, methyl phenol (including isomers), ethyl phenol (including isomers), butyl phenol (including isomers), pentyl phenol (including isomers), dimethyl phenol (including isomers), diethyl phenol (including isomers), dibutyl phenol (including isomers) or dipentyl phenol (including isomers); aliphatic hydrocarbons such as cyclohexane, cyclopentane, cyclooctane or ethylcyclohexane; alicyclic alcohols such as cyclohexanol, cyclopentanol or cyclooctanol; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; and sulfoxides such as dimethylsulfoxide or diphenylsulfoxide. Moreover, additional examples may include halogenated aromatic hydrocarbon compounds such as chlorobenzene, dichlorobenzene, trichlorobenzene, fluorobenzene, chlorotoluene, chloronaphthalene or bromonaphthalene, and halogenated aliphatic hydrocarbon compounds or halogenated alicyclic hydrocarbon compounds such as chlorohexane, chlorocyclohexane, trichlorofluoroethane, methylene chloride or carbon tetrachloride.

There are no particular limitations on the reaction apparatus used when carrying out this reaction, and the known reaction vessel can be used. For example, conventionally known reaction vessels can be suitably combined, such as a stirring tank, a pressurized stirring tank, a depressurized stirring tank, a column type reaction vessel, a distillation column, a packed column or a thin film distiller. There are no particular limitations on the material of the reaction vessel, and known materials can be used, examples of which may include glass, stainless steel, carbon steel, Hastelloy, glass-lined base materials and Teflon (registered trademark) coated materials.

According to step (2), the mixture is obtained containing carbamic acid ester, urea and alcohol.

<Step (3)>

Step (3) is a step that uses the mixture of step (1) or step (2) and an aromatic hydroxy compound to produce a composition containing carbamic acid ester and an aromatic hydroxy compound by separating the alcohol and carbonic acid ester or urea contained in the mixture.

The following provides an explanation of step (3).

Step (3) is preferably a step for obtaining a composition containing a carbamic acid ester and an aromatic hydroxy compound by separating an alcohol and a carbonic acid ester or urea from a mixture of the mixture of step (1) or step (2) and an aromatic hydroxy compound. Although several methods can be considered as methods for carrying out this step (3), in one aspect thereof, this step is carried out in a distillation apparatus, the mixture of step (1) or step (2) is supplied to a distillation apparatus as a mixture with an aromatic hydroxy compound, alcohol and carbonic acid ester or urea is recovered from a top of the column, and the composition containing carbamic acid ester and aromatic hydroxy compound is obtained from a bottom of the column.

In addition, in another aspect thereof, a mixture obtained by separating all or a portion of the alcohol and/or a portion of the carbonic acid ester or urea from the mixture of step (1) or step (2) is mixed with an aromatic hydroxy compound, and the carbonic acid ester or urea is separated from the mixture. Namely, step (3) is carried out in a distillation apparatus, and is carried out with a process comprising the following steps (3-1) and (3-2):

step (3-1): supplying the mixture of step (1) or step (2) to a distillation apparatus, an alcohol and/or a carbonic acid ester or an urea being recovered from a top of the column, and a mixture containing the carbamic acid ester, the alcohol and/or the carbonic acid ester or the urea being recovered from a bottom of the column;

step (3-2): supplying the mixture of step (3-1) to the distillation apparatus as a mixture with an aromatic hydroxy compound, the alcohol and/or the carbonic acid ester or the urea being recovered from a top of the column, and the composition containing the carbamic acid ester and the aromatic hydroxy compound being recovered from the bottom of the column.

The composition containing the mixture of carbamic acid ester and aromatic hydroxy compound can also be obtained by a method in which carbamic acid ester is obtained by distillative separation of carbonic acid ester and alcohol or the urea and alcohol are separated from a reaction liquid obtained by producing a carbamic acid ester, followed by mixing with the mixture of the carbamic acid ester and aromatic hydroxy compound. However, in this method, during distillative separation, for example, thermal denaturation of carbamic acid ester occurs easily as a result of dimerization, oligomerization and the like due to the occurrence of decarboxylation reactions between ester groups of the carbamic acid ester as indicated in formula (2) above, which not only causes a decrease in the yield of carbamic acid ester, but also results in the problem of polymeric deposits accumulating in the reaction vessel where the distillative separation is carried out, thereby impairing long-term operation. As a result of conducting extensive studies to resolve this problem, the inventors of the present invention found that the carbamic acid ester thermal denaturation reaction as described above can be inhibited by carrying out distillative separation of the carbonic acid ester and the alcohol or the urea and the alcohol from a reaction liquid obtained by producing carbamic acid ester in the presence of the previously described aromatic hydroxy compound, and recovering as a mixture of carbamic acid ester and aromatic hydroxy compound, thereby solving the above problem. Although the mechanism by which thermal denaturation of carbamic acid ester is inhibited is not clear, the inventors of the present invention presumed that, for example, the ester groups of the carbamic acid ester form hydrogen bonds with the aromatic hydroxy compound, thereby inhibiting ester groups of the carbamic acid ester from approaching each other due to the presence of the hydrogen bonds, which in turn inhibits the decarboxylation reaction between ester groups of the carbamic acid ester.

Although the amount of aromatic hydroxy compound used when carrying out the distillative separation is such that the molar ratio of the number of mole of ester groups of the carbamic acid ester contained in the reaction liquid and the number of mole of aromatic hydroxy compound is within the range of from 1:0.1 to 1:500, as previously stated, it is preferable to use a large amount of the aromatic hydroxy compound in order to inhibit thermal denaturation of the carbamic acid ester contained in the reaction liquid. However, in consideration of the size of the apparatus in which the distillative separation is carried out and the amount of heat required by the distillative separation, the molar ratio is more preferably within the range of from 1:0.2 to 1:300 and even more preferably within the range of from 1:0.3 to 1:30, and can be determined while taking into consideration the ratio of the number of moles of the ester groups of carbamic acid ester in the finally obtained composition of the present embodiment and the number of mole of aromatic hydroxy compound, as well as the amount of aromatic hydroxy compound distilled during distillative separation.

Although varying according to the composition of the liquid supplied to the distillation apparatus where the distillative separation is carried out, temperature, distillation apparatus and the like, the pressure at which the distillative separation is carried out may be a decreased pressure, an atmospheric pressure or an increased pressure, and generally the distillative separation is preferably carried out within the range of from 0.01 kPa to 10 MPa, and in consideration of the ease of industrial application, is more preferably carried out at from 0.1 kPa to 1 MPa and even more preferably carried out within the range of from 0.5 kPa to 50 kPa.

Although known materials may be used for the apparatus and lines used to carry out the distillative separation provided they do not have a detrimental effect on the starting substances or reactants, SUS304, SUS316 or SUS316L and the like can be used preferably since they are inexpensive. There are no particular limitations on the type of distillation apparatus, and a known distillation apparatus can be used. A distillation apparatus is preferably used that is provided with lines for extracting alcohol, carbonic acid ester or urea from the distillation apparatus in the form of a gaseous component during the distillative separation, and for extracting a mixture containing carbamic acid ester and aromatic hydroxy compound in liquid form from the bottom of the distillation apparatus. Various types of methods are used for the distillation apparatus, examples of which may include a distillation column, a multistage distillation column, a continuous multistage distillation column, a packed column, a thin film evaporator, a falling film evaporator, a falling drop evaporator and combinations thereof.

A multistage distillation column refers to a distillation column having multiple stages in which the number of theoretical plates of distillation is 2 or more, and any multistage distillation column may be used provided it allows continuous distillation. Any multistage distillation column can be used for the multistage distillation column provided it is ordinarily used as a multistage distillation column, examples of which may include tray column types using a bubble tray, a porous plate tray, a valve tray or a counter-current tray, and a packed column types packed with various types of packing materials such as a raschig ring, a lessing ring, a pole ring, a Berl saddle, an Interlock saddle, a Dixon packing, a McMahon packing, Helipack, a Sulzer packing or Mellapak. Any packed column can be used provided the column is packed with a known packing material as described above. Moreover, a combination tray-packed column type is also used preferably that combines a tray portion with a portion packed with a packing material. The distillation column is preferably provided with a line for supplying a reaction liquid obtained by producing carbamic acid ester and an aromatic hydroxy compound or a mixture thereof, a line for extracting the alcohol and the carbonic acid ester or the urea in the form of a gaseous phase component, and a line for extracting a mixed liquid containing the carbamic acid ester and the aromatic hydroxy compound, and the line for extracting the gaseous phase component is preferably at a location that allows the gaseous phase component of the apparatus where distillative separation is carried out to be extracted, and the line for extracting the mixed liquid containing the aryl carbamate and the aromatic hydroxy compound is particularly preferably located there below. The alcohol and the carbonic acid ester or the urea may be respectively distilled and extracted in the apparatus where the distillative separation is carried out, or may be extracted in the form of a mixture.

A line for supplying inert gas and/or liquid inert solvent from the lower portion of the reaction vessel may be separately attached, and in the case the composition obtained by the distillation procedure contains undesired amounts of alcohol, carbonic acid ester or urea, a line may be attached for circulating all or a portion of the composition to the apparatus where distillation is carried out. Furthermore, in the case of using the above-mentioned inert solvent, the inert solvent may be in the form of a gas and/or a liquid.

Alcohol, carbonic acid ester, urea and azeotropic and/or accompanying aromatic hydroxy compounds and the like extracted from the apparatus may be recycled after purifying using the known method such as a distillation column. Equipment for warming, cooling or heating may be added to each line in consideration of clogging and the like.

The ratio of the number of mole of ester groups of the carbamic acid ester in the mixture of carbamic acid ester and aromatic hydroxy compound obtained by distillative separation and the number of mole of the aromatic hydroxy compound may be made to be a desired ratio by adding aromatic hydroxy compound to the mixture in the case the amount of aromatic hydroxy compound is low with respect to the desired molar ratio. Conversely, the ratio of the number of mole of ester groups of the carbamic acid ester in the mixture of carbamic acid ester and aromatic hydroxy compound obtained by distillative separation and the number of mole of aromatic hydroxy compound may also be made to be a desired ratio by further separating the aromatic hydroxy compound by distillation in the case the amount of the aromatic hydroxy compound is high with respect to the desired molar ratio.

In addition, the alcohol and/or carbonic acid ester or urea recovered in step (3) explained above can be reused in step (1) or step (2).

<Step (4)>

Step (4) is a step for transferring the composition obtained in step (3) to a reaction vessel where step (5) is carried out in a liquid state. In this step (4), the temperature during transfer of the composition is preferably 180° C. or lower. When transferring the composition in a liquid form, although the composition is put into liquid form by heating to a temperature equal to or higher than the temperature at which the composition becomes a homogeneous liquid, in the case the temperature at which the composition becomes a homogeneous liquid is higher than 180° C., thermal decomposition of the carbamic acid ester constituting the composition occurs when transforming the composition into the liquid form, thereby resulting in the case of isocyanate being formed at undesirable locations and making this undesirable. From such a viewpoint, the temperature at which the composition becomes a homogeneous liquid is preferably 180° C. or lower, and in consideration of the ease of maintaining the temperature of the transfer line and the like, the temperature is more preferably 150° C. or lower and even more preferably 100° C. or lower.

<Step (5)>

Step (5) is a step for producing isocyanate using the composition transferred in step (4). Step (5) can be carried out by a method in which isocyanate is produced by subjecting the carbamic acid ester contained in the composition to a thermal decomposition reaction in the presence of the aromatic hydroxy compound contained in the composition, a method in which isocyanate is produced by obtaining the aryl carbamate having a group derived from an aromatic hydroxy compound by reacting carbamic acid ester contained in the composition with the aromatic hydroxy compound contained in the composition, followed by subjecting the aryl carbamate to a thermal decomposition reaction, or a method that combines these methods. The following provides an explanation of step (5). Step (5) can be carried out by the two methods indicated below.

<Direct Method>

As a first method for carrying out step (5), a method is explained in which isocyanate is produced by subjecting the carbamic acid ester contained in the composition to a thermal decomposition reaction in the presence of the aromatic hydroxy compound contained in the composition.

The thermal decomposition reaction mainly contains a reaction that forms a corresponding isocyanate and hydroxy compound (alcohol or aromatic hydroxy compound derived from a carbamic acid ester) from a carbamic acid ester, and is carried out in the presence of an aromatic hydroxy compound as described above.

Although reaction conditions vary according to the compounds used, the stoichiometric ratio of the amount of aromatic hydroxy compound used to the carbamic acid ester used is preferably from 1 to 100 times. Although it is preferable to use a large amount of aromatic hydroxy compound to inhibit side reactions as previously described, in consideration of the size of the reaction vessel and the like, the stoichiometric ratio is more preferably from 2 to 80 times and even more preferably from 2 to 50 times. An aromatic hydroxy compound of the same type as the aromatic hydroxy compound contained in the composition may be further added during the thermal decomposition reaction, and the thermal decomposition reaction may also be carried out by adding the aromatic hydroxy compound of a different type from the aromatic hydroxy compound contained in the composition in consideration of separation of the isocyanate formed, the hydroxy compound and the like.

The reaction temperature is generally within the range of from 100 to 400° C., and although a high temperature is preferable for increasing the reaction rate, since side reactions as described above may be conversely caused by the carbamic acid ester and/or the product in the form of the isocyanate, the reaction temperature is preferably within the range of from 130 to 300° C. and more preferably within the range of from 150 to 250° C. A known cooling apparatus or heating apparatus may be installed in the reaction vessel to maintain a constant reaction temperature. In addition, although varying according to the types of compounds used and reaction temperature, the reaction pressure may be a decreased pressure, a normal pressure or an increased pressure, and the reaction is generally carried out at a pressure within the range of from 20 to $1\times10^6$ Pa. There are no particular limitations on the reaction time (residence time in the case of a continuous method) and is generally from 0.001 to 100 hours, preferably from 0.01 to 50 hours and more preferably from 0.1 to 30 hours. A catalyst can be used in the present embodiment, and the catalyst is used at 0.01 to 30% by weight and preferably at 0.5 to 20% by weight based on the weight of the aryl carbamate. For example, organic metal catalysts such as dibutyl tin dilaurate, lead octoate or stannous octoate, or amines such as 1,4-diazabicyclo[2,2,2]octane, triethylenediamine or triethylamine are suitable for use as catalysts, while organic metal catalysts such as dibutyl tin dilaurate, lead octoate or stannous octoate are particularly preferable. These compounds may be used alone or two or more types may be used as a mixture.

A solvent can also be used in the present embodiment, and although examples of solvents that can be used may include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; nitrile compounds such as acetonitrile or benzonitrile; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; alicyclic alcohols such as cyclohexanol, cyclopentanol or cyclooctanol; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; and, sulfoxides such as dimethylsulfoxide or diphenylsulfoxide, based on the complexity of the procedure during separation and recovery of the hydroxy compound, the carbamic acid ester thermal decomposition reaction is preferably carried out without using a solvent.

As was previously described, although the thermal decomposition reaction of the present embodiment is a reaction by which a corresponding isocyanate and a hydroxy compound are formed from the carbamic acid ester, the thermal decomposition reaction is an equilibrium reaction. Thus, in order to efficiently obtain isocyanate in this thermal decomposition reaction, it is preferable to remove at least one of the products of this thermal decomposition reaction in the form of the isocyanate and the hydroxy compound from the thermal decomposition reaction system in the form of a gaseous component by a method such as distillation. Whether the isocyanate or hydroxy compound is removed as a gaseous component can be arbitrarily determined according to the compounds used, and for example, the respective normal boiling points of the isocyanate and the hydroxy compound are compared followed by removing the compound having the lower normal boiling point in the form of a gaseous component.

The thermal decomposition reaction is preferably carried out by a continuous method. A continuous method refers to a method in which the carbamic acid ester is continuously supplied to a reaction vessel where it is subjected to a thermal decomposition reaction, and at least either the formed isocyanate or hydroxy compound is removed from the reaction vessel in the form of a gaseous component, while a portion or all of the liquid containing the carbamic acid ester and/or aromatic hydroxy compound is removed from the bottom of the reaction vessel.

In the case of carrying out the carbamic acid ester thermal decomposition reaction using a continuous method, the carbamic acid ester is supplied to the reaction vessel where the thermal decomposition reaction is carried out in the form of a composition with an aromatic hydroxy compound of the present embodiment. Although there are many cases in which the carbamic acid ester is a solid at normal temperatures (e.g., 25° C.), since there many cases in which the composition of the present embodiment is a liquid, there are many cases in which it is advantageous in terms of continuously supplying to the reaction vessel. In addition, since there are many case in which it is advantageous for the composition of the present embodiment to have a low viscosity when transferring the composition to the reaction vessel, there are many cases in which the composition is supplied to the reaction vessel while maintaining at a certain temperature (for example, 130° C.). Although side reactions occur as described above ultimately leading to a decrease in the yield of isocyanate if the carbamic acid ester is held at these temperature conditions for a long period of time, the inventors of the present invention surprisingly found that the composition of the present embodiment is resistant to the occurrence of such side reactions even if held under such temperature conditions for a long period of time. Although the mechanism by which these aromatic hydroxy compounds inhibit side reactions is not clear, as previously described, the inventors of the present invention presumed that, as a result of an aromatic hydroxy compound forming hydrogen bonds between urethane bonds (—NHCOO—) of the carbamic acid ester and the aromatic hydroxy compound, a state is formed in which the urethane bonds have difficulty in approaching each other, thereby making it difficult for a reaction that forms urea bonds to occur as in, for example, a reaction that forms urea bonds represented by the above-mentioned formula (2).

Although known materials may be used for the reaction vessel and lines used to carry out the thermal decomposition reaction provided they do not have a detrimental effect on the carbamic acid ester or the products in the form of the hydroxy compound and isocyanate, SUS304, SUS316 or SUS316L and the like can be used preferably since they are inexpensive. There are no particular limitations on the type of reaction vessel, and a known tank type reaction vessel or a column type reaction vessel can be used. A reaction vessel is preferably used that is provided with lines for extracting a low boiling point mixture containing at least either the isocyanate or the hydroxy compound formed in the thermal decomposition reaction from the reaction vessel in the form of a gaseous component, and for removing all or a portion of a mixed liquid containing unreacted carbamic acid ester and compounds not extracted in the form of a gaseous component from the lower portion of the reaction vessel. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a thin film evaporator or a columnar reaction vessel are preferable from the viewpoint of rapidly removing the low boiling point component from the reaction system, while a structure having a large gas-liquid contact area is preferable for rapidly transferring the low boiling point component formed to the gaseous phase.

The reaction vessel is preferably provided with a line for supplying the carbamic acid ester, a line for extracting a gaseous component containing at least either the isocyanate or the hydroxy compound formed by the thermal decomposition reaction, and a line for extracting a mixed liquid containing compounds not removed as a gaseous component and unreacted carbamic acid ester, and the line for extracting the gaseous component containing at least either the isocyanate or hydroxy compound is preferably located at a location that allows the gaseous component in the reaction vessel to be extracted, and the line for extracting the mixed liquid containing compounds not removed as a gaseous component, unreacted carbamic acid ester and the aromatic hydroxy compound is particularly preferably located there below.

In addition, a line for supplying inert gas and/or liquid inert solvent from the lower portion of the reaction vessel may be separately attached, and a line may also be attached for recirculating all or a portion of the mixed liquid containing unreacted carbamic acid ester and/or active hydrogen extracted from the bottom of the reaction vessel. Equipment for warming, cooling or heating may be added to each line in consideration of clogging and the like.

Although there are many cases in which the gaseous component removed from the thermal decomposition reaction, and/or the mixed liquid containing compounds not removed as a gaseous component, unreacted carbamic acid ester and aromatic hydroxy compound containing aromatic hydroxy compounds and/or alcohols in the form of compounds other than isocyanates, among these compounds, the aromatic hydroxy compound can be reused as the aromatic hydroxy compound of step (3). On the other hand, the alcohol can be reused as the alcohol used in production of the dialkyl tin compound of step (A) in the process for producing carbonic acid ester, and the alcohol can also be reused during production of carbamic acid ester from an amine compound, alcohol and urea.

<Transesterification Reaction and Decomposition Method>

A method is explained for the second method of step (5) for producing isocyanate by reacting the carbamic acid ester contained in the composition of step (4) with the aromatic hydroxy compound contained in the composition to obtain the aryl carbamate having a group derived from the aromatic hydroxy compound followed by subjecting the aryl carbamate to a thermal decomposition reaction.

This process comprises the following steps (5-1) and (5-2):

step (5-1): reacting the carbamic acid ester and aromatic hydroxy compound which are contained in the composition of step (4), a low boiling point component formed being recovered in a form of a gaseous component, and a reaction liquid containing the aryl carbamate and the aromatic hydroxy compound being removed from a bottom of the reaction vessel in which the reaction occurs, and step (5-2): supplying the reaction liquid of step (5-1) to a reaction vessel in which a thermal decomposition reaction occurs, the aryl carbamate being subjected to a thermal decomposition reaction, at least one of either an isocyanate or an aromatic hydroxy compound which are formed being recovered in a form of a gaseous component, and all or a portion of a mixture containing the isocyanate and/or the aromatic hydroxy compound and/or the aryl carbamate not recovered in a form of a gaseous component being recovered from the bottom of the reaction vessel.

<Step (5-1)>

In step (5-1), the carbamic acid ester and the aromatic hydroxy compound are reacted to obtain the aryl carbamate having a group derived from the aromatic hydroxy compound. In this reaction, an ester group of the carbamic acid ester is replaced with an aryloxy group derived from the aromatic hydroxy compound resulting in the formation of the corresponding aryl carbamate and a hydroxy compound derived from the carbamic acid ester (also referred to as a "transesterification reaction" in the present description).

Although varying according to the reacted compounds, the reaction conditions of this transesterification reaction are such that the aromatic hydroxy compound is used within the range of from 2 to 1000 times the ester group of the carbamic acid ester when expressed as the stoichiometric ratio. As a result of conducting extensive studies, the inventors of the present invention surprisingly found that by using an aromatic hydroxy compound having a substituent at at least one ortho position with respect to the hydroxyl group in this transesterification reaction as previously described, side reactions as previously described attributable to the carbamic acid ester and/or product in the form of the aryl carbamate can be inhibited in the transesterification reaction. In the transesterification reaction, although the aromatic hydroxy compound is preferably used in excess with respect to the ester group of the carbamic acid ester in order to inhibit side reactions attributable to the carbamic acid ester and/or product in the form of the aryl carbamate as well as allow the reaction to be completed quickly, the aromatic hydroxy compound is preferably used within the range of from 2 to 100 times and preferably within the range of from 5 to 50 times in consideration of the size of the reaction vessel.

During the transesterification reaction, an aromatic hydroxy compound of the same type as the aromatic hydroxy compound contained in the composition may be further added, or the thermal decomposition reaction may be carried out by adding a different type of aromatic hydroxy compound from the aromatic hydroxy compound contained in the composition in consideration of separation of the resulting isocyanate, hydroxy compound and the like.

The reaction temperature is generally within the range of from 100 to 300° C., and although high temperatures are preferable in order to increase the reaction rate, since there conversely may be greater susceptibility to the occurrence of side reactions at high temperatures, the reaction temperature is preferably within the range of from 150 to 250° C. A known cooling apparatus or heating apparatus may be installed in the reaction vessel to maintain a constant reaction temperature. In addition, although varying according to the types of compounds used and reaction temperature, the reaction pressure may be a decreased pressure, a normal pressure or an increased pressure, and the reaction is generally carried out at a pressure within the range of from 20 to $1 \times 10^6$ Pa. There are no particular limitations on the reaction time (residence time in the case of a continuous method) and is generally from 0.001 to 100 hours, preferably from 0.01 to 50 hours and more preferably from 0.1 to 30 hours. In addition, the reaction can also be completed by confirming that a desired amount of aryl carbamate has been formed by, for example, liquid chromatography after sampling the reaction liquid. In the present embodiment, the catalyst is used at 0.01 to 30% by weight and preferably at 0.5 to 20% by weight based on the weight of the carbamic acid ester. For example, organic metal catalysts such as dibutyl tin dilaurate, lead octoate or stannous octoate, or amines such as 1,4-diazabicyclo[2,2,2]octane, triethylenediamine or triethylamine are suitable for use, while organic metal catalysts such as dibutyl tin dilaurate, lead octoate or stannous octoate are particularly preferable. These compounds may be used alone or two or more types may be used as a mixture.

Although the use of a reaction solvent is not necessarily required in the present embodiment, a suitable inert solvent is preferably used as a reaction solvent for the purpose of facilitating the reaction procedure, examples of which may include alkanes such as hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as diphenyl ether or diphenyl sulfide; and sulfoxides such as dimethylsulfoxide or diphenylsulfoxide; and, silicone oil. These solvents can be used alone or two or more types can be used as a mixture.

As has been previously described, although the transesterification reaction in the present embodiment involves an exchange between an ester group of the carbamic acid ester and an aryloxy group derived from the aromatic hydroxy compound resulting in the formation of the corresponding aryl carbamate and an alcohol, the transesterification reaction is an equilibrium reaction. Thus, in order to efficiently produce the aryl carbamate by this transesterification reaction, it is preferable to remove the products from the reaction system. Since the compound having the lowest normal boiling point in the reaction system is the alcohol formed by the transesterification reaction, the alcohol is preferably removed from the reaction system by a method such as distillative separation.

In addition, the transesterification reaction is preferably carried out by a continuous method to allow the transesterification reaction to proceed efficiently. Namely, a method is preferably used in which the carbamic acid ester and the aromatic hydroxy compound are supplied continuously to the reaction vessel to carry out the transesterification reaction, the alcohol formed is removed from the reaction vessel in the form of a gaseous component, and a reaction liquid containing the formed aryl carbamate and the aromatic hydroxy compound is continuously removed from the bottom of the reaction vessel. In the case of carrying out the transesterification reaction according to this method, in addition to promoting the transesterification reaction, there is also the unexpected effect of being able to improve the final yield of isocyanate by inhibiting side reactions as previously described.

Although known materials may be used for the reaction vessel and lines used to carry out the transesterification reaction provided they do not have a detrimental effect on the starting substances or reactants, SUS304, SUS316 or SUS316L and the like can be used preferably since they are inexpensive. There are no particular limitations on the type of reaction vessel, and a known tank-type or a column-type reaction vessel can be used. A reaction vessel is preferably used that is provided with lines for extracting a low boiling point reaction mixture containing alcohol formed in the transesterification reaction from the reaction vessel in the form of a gaseous component, and for extracting a mixed liquid containing the produced aryl carbamate and aromatic hydroxy compound from the lower portion of the reaction vessel in the form of a liquid. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a thin film evaporator or a columnar reactor are preferable from the viewpoint of efficiently shifting the equilibrium to the products side, while a structure having a large gas-liquid contact area is preferable for being able to rapidly transfer the alcohol formed to the gaseous phase.

A multistage distillation column refers to a distillation column having multiple stages in which the number of theoretical plates of distillation is 2 or more, and any multistage distillation column may be used provided it allows continuous distillation. Any multistage distillation column can be used for the multistage distillation column provided it is ordinarily used as a multistage distillation column, examples of which may include tray column types using a bubble tray, a porous plate tray, a valve tray or a counter-current tray, and packed column types packed with various types of packing materials such as a raschig ring, a lessing ring, a pole ring, a Berl saddle, an Interlock saddle, a Dixon packing, a McMahon packing, Helipack, a Sulzer packing or Mellapak. Any packed column can be used provided the column is packed with a known packing material as described above. Moreover, a combination tray-packed column type is also used preferably that combines a tray portion with a portion packed with a packing material. The reaction vessel is preferably provided with a line for supplying a mixture containing the carbamic acid ester and the aromatic hydroxy compound, a line for extracting a gaseous phase component containing alcohol formed by the transesterification reaction, and a line for extracting a mixed liquid containing the aryl carbamate and aromatic hydroxy compound, and the line for extracting the gaseous phase component containing the alcohol is preferably at a location that allows the gaseous phase component in the reaction vessel to be extracted, and the line for extracting the mixed liquid containing the aryl carbamate and the aromatic hydroxy compound is particularly preferably located there below.

A line for supplying inert gas and/or liquid inert solvent from the lower portion of the reaction vessel may be separately attached, and in the case the mixed liquid containing the formed aryl carbamate and the aromatic hydroxy compound contains unreacted carbamic acid ester, a line may be attached for recirculating all or a portion of the mixed liquid to the reaction vessel. Furthermore, in the case of using the above-mentioned inert solvent, the inert solvent may be in the form of a gas and/or a liquid.

The gaseous component containing alcohol extracted from the reaction vessel may be purified using a known method such as a distillation column, and the azeotropic and/or accompanying aromatic hydroxy compound and the like may be recycled. Equipment for warming, cooling or heating may be added to each line in consideration of clogging and the like.

The aryl carbamate preferably produced by the transesterification reaction is an aryl carbamate represented by any of the following formulas (32) to (34):

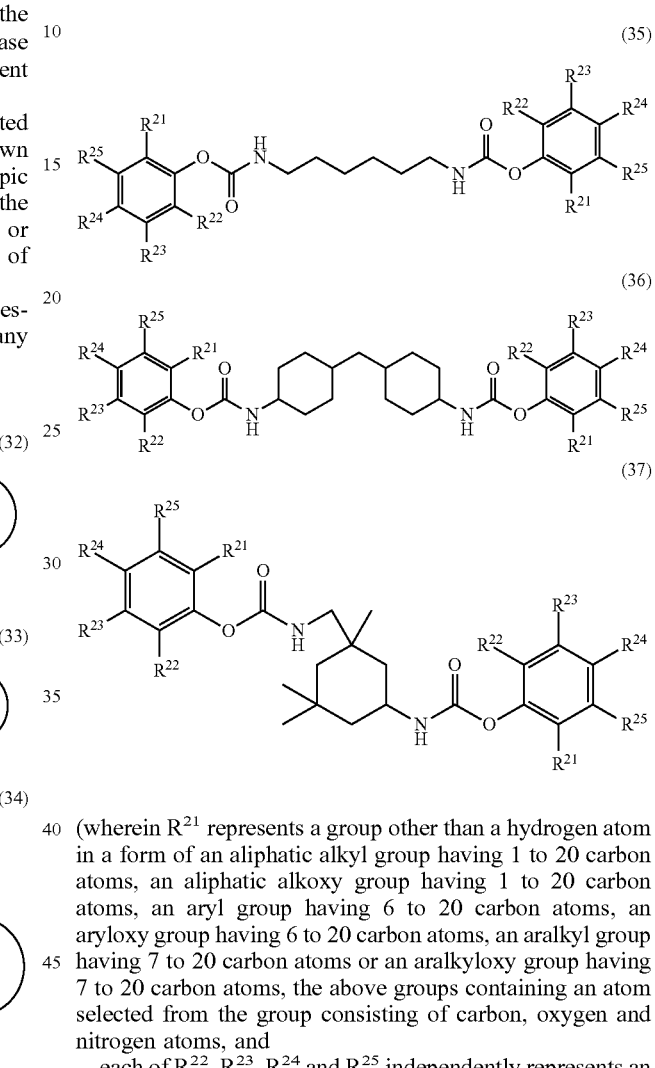

(wherein ring B represents a structure containing at least one structure selected from the group consisting of a benzene ring, naphthalene ring and anthracene ring, the structure may have a substituent, $R^{21}$ represents a group other than a hydrogen atom in a form of an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the above groups containing an atom selected from the group consisting of carbon, oxygen and nitrogen atoms, and $R^{22}$ represents an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the above groups containing an atom selected from the group consisting of carbon, oxygen and nitrogen atoms).

Among these, a more preferably produced aryl carbamate is an aryl carbamate represented by any of the following formulas (35) to (37):

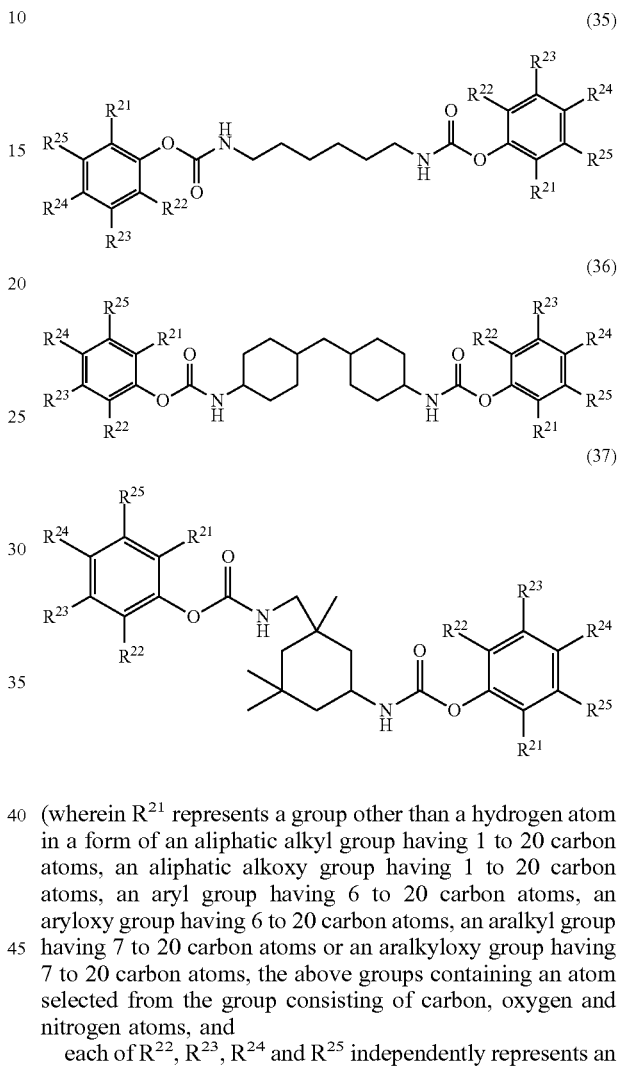

(wherein $R^{21}$ represents a group other than a hydrogen atom in a form of an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the above groups containing an atom selected from the group consisting of carbon, oxygen and nitrogen atoms, and each of $R^{22}$, $R^{23}$, $R^{24}$ and $R^{25}$ independently represents an aliphatic alkyl group having 1 to 20 carbon atoms, an aliphatic alkoxy group having 1 to 20 carbon atoms, an aryl group having 6 to 20 carbon atoms, an aryloxy group having 6 to 20 carbon atoms, an aralkyl group having 7 to 20 carbon atoms or an aralkyloxy group having 7 to 20 carbon atoms, the above groups containing an atom selected from the group consisting of carbon, oxygen and nitrogen atoms, or a hydrogen atom).

Examples of aryl carbamates represented by formula (35) may include N,N'-hexanediyl-bis-carbamic acid bis(2-ethylphenyl)ester, N,N'-hexanediyl-bis-carbamic acid bis(2-propylphenyl)ester (including isomers), N,N'-hexanediyl-bis-carbamic acid bis(2-butylphenyl)ester (including isomers), N,N'-hexanediyl-bis-carbamic acid bis(2-pentylphenyl)ester (including isomers), N,N'-hexanediyl-bis-carbamic acid bis(2-hexylphenyl)ester (including isomers), N,N'-hexanediyl-bis-carbamic acid bis(2-octylphenyl)ester (including isomers), N,N'-hexanediyl-bis-carbamic acid bis (2-cumylphenyl)ester, N,N'-hexanediyl-bis-carbamic acid bis(2,4-diethylphenyl)ester, N,N'-hexanediyl-bis-carbamic acid bis(2,4-dipropylphenyl)ester (including isomers), N,N'-hexanediyl-bis-carbamic acid bis(2,4-dibutylphenyl)ester (including isomers), N,N'-hexanediyl-bis-carbamic acid bis(2,4-dipentylphenyl)ester (including isomers), N,N'-hexanediyl-bis-carbamic acid bis(2,4-dihexylphenyl)ester (including isomers), N,N'-hexanediyl-bis-carbamic acid bis(2,4-dioctylphenyl)ester (including isomers), N,N'-hexanediyl-bis-carbamic acid bis(2,4-dicumylphenyl)ester (including isomers), N,N'-hexanediyl-bis-carbamic acid bis(2,6-dimethylphenyl)ester, N,N'-hexanediyl-bis-carbamic acid bis(2,6-diethylphenyl)ester (including isomers), N,N'-hexanediyl-bis-carbamic acid bis(2,6-dipropylphenyl)ester (including isomers), N,N'-hexanediyl-bis-carbamic acid bis(2,4,6-trimethylphenyl)ester, N,N'-hexanediyl-bis-carbamic acid bis(2,3,6-trimethylphenyl)ester, N,N'-hexanediyl-bis-carbamic acid bis(2,4,6-triethylphenyl)ester, and N,N'-hexanediyl-bis-carbamic acid bis(2,4,6-tripropylphenyl)ester (including isomers). In addition, examples of alkyl carbamates represented by formula (36) include bis(2-ethylphenyl)-4,4'-methylene-dicyclohexyl carbamate, bis(2-propylphenyl)-4,4'-methylene-dicyclohexyl carbamate (including isomers), bis(2-butylphenyl)-4,4'-methylene-dicyclohexyl carbamate (including isomers), bis(2-pentylphenyl)-4,4'-methylene-dicyclohexyl carbamate (including isomers), bis(2-hexylphenyl)-4,4'-methylene-dicyclohexyl carbamate (including isomers), bis(2-heptylphenyl)-4,4'-methylene-dicyclohexyl carbamate (including isomers), bis(2-octylphenyl)-4,4'-methylene-dicyclohexyl carbamate (including isomers), bis(2-cumylphenyl)-4,4'-methylene-dicyclohexyl carbamate, bis(2,4-diethylphenyl)-4,4'-methylene-dicyclohexyl carbamate (including isomers), bis(2,4-dipropylphenyl)-4,4'-methylene-dicyclohexyl carbamate (including isomers), bis(2,4-dibutylphenyl)-4,4'-methylene-dicyclohexyl carbamate (including isomers), bis(2,4-dipentylphenyl)-4,4'-methylene-dicyclohexyl carbamate (including isomers), bis(2,4-dihexylphenyl)-4,4'-methylene-dicyclohexyl carbamate (including isomers), bis(2,4-diheptylphenyl)-4,4'-methylene-dicyclohexyl carbamate (including isomers), bis(2,4-dioctylphenyl)-4,4'-methylene-dicyclohexyl carbamate (including isomers), bis(2,4-dicumylphenyl)-4,4'-methylene-dicyclohexyl carbamate, bis(2,6-dimethylphenyl)-4,4'-methylene-dicyclohexyl carbamate (including isomers), bis(2,6-diethylphenyl)-4,4'-methylene-dicyclohexyl carbamate (including isomers), bis(2,6-dipropylphenyl)-4,4'-methylene-dicyclohexyl carbamate (including isomers), bis(2,4,6-trimethylphenyl)-4,4'-methylene-dicyclohexyl carbamate (including isomers), bis(2,4,6-triethylphenyl)-4,4'-methylene-dicyclohexyl carbamate (including isomers) and bis(2,4,6-tripropylphenyl)-4,4'-methylene-dicyclohexyl carbamate (including isomers). Moreover, examples of alkyl carbamates represented by formula (37) may include 3-((2-ethylphenoxy)carbonylamino-methyl)-3,5,5-trimethylcyclohexyl carbamic acid (2-ethylphenyl)ester, 3-((2-propylphenoxy)carbonylamino-methyl)-3,5,5-trimethylcyclohexyl carbamic acid (2-propylphenyl)ester (including isomers), 3-((2-butylphenoxy)carbonylamino-methyl)-3,5,5-trimethylcyclohexyl carbamic acid (2-butylphenyl)ester (including isomers), 3-((2-pentylphenoxy)carbonylamino-methyl)-3,5,5-trimethylcyclohexyl carbamic acid (2-pentylphenyl)ester (including isomers), 3-((2-hexylphenoxy)carbonylamino-methyl)-3,5,5-trimethylcyclohexyl carbamic acid (2-hexylphenyl)ester (including isomers), 3-((2-heptylphenoxy)carbonylamino-methyl)-3,5,5-trimethylcyclohexyl carbamic acid (2-heptylphenyl)ester (including isomers), 3-((2-octylphenoxy)carbonylamino-methyl)-3,5,5-trimethylcyclohexyl carbamic acid (2-octylphenyl)ester (including isomers), 3-((2-cumylphenoxy)carbonylamino-methyl)-3,5,5-trimethylcyclohexyl carbamic acid (2-cumylphenyl)ester (including isomers), 3-((2,4-diethylphenoxy)carbonylamino-methyl)-3,5,5-trimethylcyclohexyl carbamic acid (2,4-diethylphenyl)ester, 3-((2,4-dipropylphenoxy)carbonylamino-methyl)-3,5,5-trimethylcyclohexyl carbamic acid (2,4-dipropylphenyl)ester (including isomers), 3-((2,4-dibutylphenoxy)carbonylamino-methyl)-3,5,5-trimethylcyclohexyl carbamic acid (2,4-dibutylphenyl)ester (including isomers), 3-((2,4-dipentylphenoxy)carbonylamino-methyl)-3,5,5-trimethylcyclohexyl carbamic acid (2,4-dipentylphenyl)ester (including isomers), 3-((2,4-dihexylphenoxy)carbonylamino-methyl)-3,5,5-trimethylcyclohexyl carbamic acid (2,4-dihexylphenyl)ester (including isomers), 3-((2,4-diheptylphenoxy)carbonylamino-methyl)-3,5,5-trimethylcyclohexyl carbamic acid (2,4-diheptylphenyl)ester (including isomers), 3-((2,4-dioctylphenoxy)carbonylamino-methyl)-3,5,5-trimethylcyclohexyl carbamic acid (2,4-dioctylphenyl)ester (including isomers), 3-((2,4-dicumylphenoxy)carbonylamino-methyl)-3,5,5-trimethylcyclohexyl carbamic acid (2,4-dicumylphenyl)ester, 3-((2,6-dimethylphenoxy)carbonylamino-methyl)-3,5,5-trimethylcyclohexyl carbamic acid (2,6-dimethylphenyl)ester, 3-((2,6-diethylphenoxy)carbonylamino-methyl)-3,5,5-trimethylcyclohexyl carbamic acid (2,6-diethylphenyl)ester, 3-((2,6-dipropylphenoxy)carbonylamino-methyl)-3,5,5-trimethylcyclohexyl carbamic acid (2,6-dipropylphenyl)ester (including isomers), 3-((2,4,6-trimethylphenoxy)carbonylamino-methyl)-3,5,5-trimethylcyclohexyl carbamic acid (2,4,6-trimethylphenyl)ester, 3-((2,4,6-triethylphenoxy)carbonylamino-methyl)-3,5,5-trimethylcyclohexyl carbamic acid (2,4,6-triethylphenyl)ester, and 3-((2,4,6-tripropylphenoxy)carbonylamino-methyl)-3,5,5-trimethylcyclohexyl carbamic acid (2,4,6-tripropylphenyl)ester (including isomers).

The aryl carbamate produced in the transesterification reaction may be subjected to the subsequent thermal decomposition reaction while still as a mixed liquid containing aryl carbamate and aromatic hydroxy compound removed from the reaction vessel, or the aryl carbamate may be subjected to the thermal decomposition reaction after purifying from the mixed liquid. A known method can be used to purify the aryl carbamate from the reaction liquid, examples of which may include removal of the aromatic hydroxy compound by distillation, washing with a solvent and purification of the aryl carbamate by crystallization.

Since the aryl carbamate of the present embodiment is a carbamic acid ester composed of an aromatic hydroxy compound and an isocyanate, the thermal decomposition temperature is low as is generally known. In addition, the aryl carbamate of the present embodiment is unexpectedly extremely resistant to the occurrence of side reactions (such as a reaction resulting in the formation of a urea bond as previously described) at high temperatures (such as 200° C.) at which the thermal decomposition reaction is carried out. Although the mechanism by which side reactions are inhibited is unclear, as was previously described, it is presumed that a substituent at the ortho position relative to the hydroxyl group sterically protects a urethane bond, thereby hindering the reaction between a different carbamic acid ester and the urethane bond.

Moreover, although the aromatic hydroxy compound formed by the thermal decomposition reaction of the aryl carbamate of the present embodiment is an aromatic hydroxy compound having a substituent at the ortho position relative to a hydroxyl group, since the reaction rate between the aromatic hydroxy compound and isocyanate is surprisingly slow, namely the reverse reaction rate in the thermal decomposition reaction is surprisingly low, when carrying out the thermal decomposition reaction on the aryl carbamate, there is the advantage of being able to easily separate the aromatic hydroxy compound and the isocyanate.

The alcohol derived from carbamic acid ester formed in the above-mentioned transesterificaion reaction step can be reused as the alcohol used to produce the dialkyl tin compound of step (A) in the process for producing carbonic acid ester, or it can be reused as the alcohol used when producing carbamic acid ester from an amine compound, alcohol and urea.

<Step (5-2)>

The following provides an explanation of the aryl carbamate decomposition reaction of step (5-2).

The decomposition reaction of the present embodiment is a thermal decomposition reaction by which the corresponding isocyanate and the aromatic hydroxy compound are formed from the aryl carbamate.

The reaction temperature is generally within the range of from 100 to 300° C., and although a high temperature is preferable for increasing the reaction rate, since side reactions as described above may be conversely caused by the aryl carbamate and/or the reaction product in the form of the isocyanate, the reaction temperature is preferably within the range of from 150 to 250° C. A known cooling apparatus or heating apparatus may be installed in the reaction vessel to maintain a constant reaction temperature. In addition, although varying according to the types of compounds used and reaction temperature, the reaction pressure may be a decreased pressure, a normal pressure or an increased pressure, and the reaction is generally carried out at a pressure within the range of from 20 to $1 \times 10^6$ Pa. There are no particular limitations on the reaction time (residence time in the case of a continuous method) and is generally from 0.001 to 100 hours, preferably from 0.01 to 50 hours and more preferably from 0.1 to 30 hours. A catalyst can be used in the present embodiment, and the catalyst is used at 0.01 to 30% by weight and preferably at 0.5 to 20% by weight based on the weight of the aryl carbamate. For example, organic metal catalysts such as dibutyl tin dilaurate, lead octoate or stannous octoate, or amines such as 1,4-diazabicyclo[2,2,2] octane, triethylenediamine or triethylamine are suitable for use as catalysts, while organic metal catalysts such as dibutyl tin dilaurate, lead octoate or stannous octoate are particularly preferable. These compounds may be used alone or two or more types may be used as a mixture. In the case of using a catalyst in the above-mentioned transesterification reaction, the catalyst contained in the mixed liquid following the transesterification reaction may be used as a catalyst in the thermal decomposition reaction or catalyst may be freshly added to the aryl carbamate when the thermal decomposition reaction is carried out.

Although the use of a reaction solvent is not necessarily required in the present embodiment, a suitable inert solvent can be used as a reaction solvent for the purpose of facilitating the reaction procedure, examples of which may include alkanes such as hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as diphenyl ether or diphenyl sulfide; and sulfoxides such as dimethylsulfoxide or diphenylsulfoxide; and, silicone oil. These solvents can be used alone or two or more types can be used as a mixture.

As was previously described, although the thermal decomposition reaction of the present embodiment is a reaction by which the corresponding isocyanate and the aromatic hydroxy compound are formed from the aryl carbamate, the thermal decomposition reaction is an equilibrium reaction. Thus, in order to efficiently obtain isocyanate in this thermal decomposition reaction, it is preferable to remove at least one of the products of this thermal decomposition reaction in the form of the isocyanate and the aromatic hydroxy compound from the thermal decomposition reaction system in the form of a gaseous component by a method such as distillation. Whether the isocyanate or the aromatic hydroxy compound is removed as a gaseous component can be arbitrarily determined according to the compounds used, and for example, the respective normal boiling points of the isocyanate and the aromatic hydroxy compound are compared followed by removing the compound having the lower normal boiling point in the form of a gaseous component.

The aryl carbamate is also susceptible to the occurrence of side reactions as described above in the case of being held at a high temperature for a long period of time, although to a much lower degree than carbamic acid ester. In addition, the above-mentioned side reactions may also be induced by the isocyanate formed by the thermal decomposition reaction. Thus, the time during which the aryl carbamate and the isocyanate are held at a high temperature is preferably as short as possible, and the thermal decomposition reaction is preferably carried out by a continuous method. A continuous method refers to a method in which the aryl carbamate is continuously supplied to the reaction vessel where it is subjected to a thermal decomposition reaction, and at least either the formed isocyanate or aromatic hydroxy compound is removed from the reaction vessel in the form of a gaseous component.

Although known materials may be used for the reaction vessel and lines used to carry out the thermal decomposition reaction provided they do not have a detrimental effect on the aryl carbamate or the products in the form of the aromatic hydroxy compound and isocyanate, SUS304, SUS316 or SUS316L and the like can be used preferably since they are inexpensive. There are no particular limitations on the type of reaction vessel, and a known tank-type reaction vessel or a column-type reaction vessel can be used. A reaction vessel is preferably used that is provided with lines for extracting a low boiling point mixture containing at least either the isocyanate or the aromatic hydroxy compound formed in the thermal decomposition reaction from the reaction vessel in the form of a gaseous component, and for removing a mixed liquid containing unreacted aryl carbamate and compounds not extracted in the form of a liquid from the lower portion of the reaction vessel. Various known methods are used for such a reaction vessel, examples of which may include types using reaction vessels containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a thin film evaporator or a columnar reactor are preferable from the viewpoint of rapidly removing a low boiling point component from the reaction system, while a structure having a large gas-liquid contact area is preferable for rapidly transferring the low boiling point component formed to the gaseous phase.

The reaction vessel is preferably provided with a line for supplying the aryl carbamate, a line for extracting a gaseous component containing at least either the isocyanate or the aromatic hydroxy compound formed by the thermal decomposition reaction, and a line for extracting a mixed liquid containing compounds not removed as a gaseous component and unreacted aryl carbamate, the line for extracting the gaseous component containing at least either the isocyanate or the aromatic hydroxy compound is preferably located at a location that allows the gaseous component in the reaction vessel to be extracted, and the line for extracting the mixed liquid containing compounds not removed as a gaseous component and unreacted aryl carbamate is particularly preferably located there below.

In addition, a line for supplying inert gas and/or liquid inert solvent from the lower portion of the reaction vessel may be separately attached, and a line may also be attached for recirculating all or a portion of the mixed liquid containing unreacted aryl carbamate and compounds not removed as a gaseous component to the reaction vessel. Equipment for warming, cooling or heating may be added to each line in consideration of clogging and the like. Furthermore, in the case of using the above-mentioned inert solvent, the inert solvent may be in the form of a gas and/or a liquid.

The aromatic hydroxy compound obtained in the thermal decomposition reaction can be reused as the aromatic hydroxy compound in step (3) in the process for producing the composition of the present embodiment. When reusing the aromatic hydroxy compound, the aromatic hydroxy compound may be reused after purifying by a known method such as distillative purification. In addition, the entire amount of the aromatic hydroxy compound obtained in the thermal decomposition reaction may be reused or only a portion thereof may be reused.

FIG. 8 shows the process flow of an example of a modified process for producing isocyanate combining the composition of the present embodiment, a step for producing carbonic acid ester and the composition using the carbonic acid ester, a step for producing isocyanate using the composition, and the reuse of alcohol and/or aromatic hydroxy compound obtained in each step.

A mixture is produced containing the carbonic acid ester produced by going through steps (A) and (B) and the carbamic ester in step (1) using amine compounds. The excess carbonic acid ester and by-product alcohol contained in this mixture are subjected to distillative separation in step (3) in the presence of aromatic hydroxy compound to obtain the composition of the present embodiment containing carbamic acid ester and the aromatic hydroxy compound. The alcohol is reused as the alcohol in the regeneration step of the dialkyl tin compound of step (C), while the carbonic acid ester is reused as the carbonic acid ester of step (1). Next, although isocyanate is produced using the composition of the present embodiment obtained in step (3), the production of isocyanate may be carried out by a method in which isocyanate is produced by subjecting the composition to a transesterification reaction as previously described, by a method in which isocyanate is produced by producing the aryl carbamate by subjecting the composition to a transesterification reaction and then subjecting the aryl carbamate to a thermal decomposition reaction, or by a method that combines both. In the isocyanate production step, the alcohol derived from the separated carbamic acid ester and the aromatic hydroxy compound are reused in the dialkyl tin compound regeneration step of step (C) and the step for producing the composition containing the carbamic acid ester and the aromatic hydroxy compound of step (3), respectively. They may also be subjected to a purification step and the like in addition to the steps described above.

The composition of the present embodiment as described above is a composition suitable for transfer and storage of carbamic acid ester, and this composition enables reductions in yield of carbamic acid ester caused by thermal denaturation and the like to be inhibited. In addition, the composition can also be used in the production of isocyanate, and isocyanate produced with this composition can be preferably used as a production raw material of polyurethane foam, paints, adhesives and the like, thereby making it extremely important industrially.

EXAMPLES

Although the following provides a detailed explanation of the present invention based on examples thereof, the scope of the present invention is not limited by these examples.
<Analytical Methods>
1) NMR Analysis
Apparatus: JNM-A400 FT-NMR system, JEOL Ltd., Japan
(1) Preparation of $^1$H-, $^{13}$C- and $^{119}$Sn-NMR Analysis Samples About 0.3 g of sample solution were weighed followed by the addition of about 0.7 g of heavy chloroform (99.8%, Aldrich Corp., USA) and about 0.05 g of internal standard in the form of tetramethyl tin (guaranteed reagent, Wako Pure Chemical Industries, Ltd., Japan) and mixing to uniformity to obtain solutions used as NMR analysis samples.
(2) Quantitative Analysis Analyses were performed for each standard and quantitative analyses were performed on the analysis sample solutions based on the resulting calibration curve.
2) Liquid Chromatography
Apparatus: LC-10AT system, Shimadzu Corp., Japan
Column: Silica-60 column, Tosoh Corp., Japan, two columns connected in series
Developing solvent: Mixed liquid of hexane/tetrahydrofuran (80/20) (v/v)
Solvent flow rate: 2 mL/min
Column temperature: 35° C.
Detector: R.I. (refractometer)
(1) Liquid Chromatography Analysis Samples About 0.1 g of sample were weighed followed by the addition of about 1 g of tetrahydrofuran (dehydrated, Wako Pure Chemical Industries, Ltd., Japan) and about 0.02 g of internal standard in the form of bisphenol A (guaranteed reagent, Wako Pure Chemical Industries, Ltd., Japan) and mixing to uniformity to obtain solutions used as liquid chromatography analysis samples.

(2) Quantitative Analysis

Analyses were performed for each standard and quantitative analyses were performed on the analysis sample solutions based on the resulting calibration curve.

3) Gas Chromatography

Apparatus: GC-2010, Shimadzu Corp., Japan

Column: DB-1 column, Agilent Technologies Corp., USA, length: 30 m, inner diameter: 0.250 mm, film thickness: 1.00 μm Column temperature: Held at 50° C. for 5 minutes followed by increasing at the rate of 10° C./min to 200° C.; held at 200° C. for 5 minutes followed by increasing at the rate of 10° C./min to 300° C.

Detector: FID (1) Gas Chromatography Analysis Samples

About 0.05 g of sample were weighed followed by the addition of about 1 g of acetone (dehydrated, Wako Pure Chemical Industries, Ltd., Japan) and about 0.02 g of internal standard in the form of toluene (dehydrated, Wako Pure Chemical Industries, Ltd., Japan) and mixing to uniformity to obtain solutions used as gas chromatography analysis samples.

(2) Quantitative Analysis

Analyses were performed for each standard and quantitative analyses were performed on the analysis sample solutions based on the resulting calibration curve.

Example 1

Step (1-1): Production of Bis(3-methylbutyl) Carbonate 625 g (2.7 mol) of di-n-butyl tin oxide (Sankyo Organic Chemicals Co., Ltd., Japan) and 2020 g (22.7 mol) of 3-methyl-1-butanol (Kuraray Co., Ltd., Japan) were placed in a 5000 mL volumetric pear-shaped flask. The flask was connected to an evaporator (R-144, Shibata Co., Ltd., Japan) to which was connected an oil bath (OBH-24, Masuda Corp., Japan) equipped with a temperature controller, a vacuum pump (G-50A, Ulvac Inc., Japan) and a vacuum controller (VC-10S, Okano Seisakusho Co., Ltd.). The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to about 145° C., the flask was immersed in the oil bath and rotation of the evaporator was started. After heating for about 40 minutes in the presence of atmospheric pressure nitrogen with the purge valve of the evaporator left open, distillation of 3-methyl-1-butanol containing water began. After maintaining in this state for 7 hours, the purge valve was closed, pressure inside the system was gradually reduced, and excess 3-methyl-1-butanol was distilled with the pressure inside the system at 74 to 35 kPa. After the fraction no longer appeared, the flask was taken out of the oil bath. After allowing the flask to cool to the vicinity of room temperature (25° C.), the flask was taken out of the oil bath, the purge valve was opened gradually and the pressure inside the system was returned to atmospheric pressure. 1173 g of reaction liquid were obtained in the flask. Based on the results of $^{119}$Sn-, $^{1}$H- and $^{13}$C-NMR analyses, 1,1,3,3-tetra-n-butyl-1,3-bis(3-methyl-butyloxy) distannoxane was confirmed to have been obtained at a yield of 99% based on di-n-butyl tin oxide. The same procedure was then repeated 12 times to obtain a total of 10335 g of 1,1,3,3-tetra-n-butyl-1,3-bis(3-methylbutyloxy) distannoxane.

Bis(3-methylbutyl) carbonate was produced in a continuous production apparatus like that shown in FIG. 1. 1,1,3,3-Tetra-n-butyl-1,3-bis(3-methylbutyloxy) distannoxane produced in the manner described above was supplied at the rate of 4388 g/hr from a transfer line 4 into a column-type reaction vessel 102 packed with Metal Gauze CY Packing (Sulzer Chemtech Ltd., Switzerland) and having an inner diameter of 151 mm and effective length of 5040 mm, and 3-methyl-1-butanol purified with a distillation column 101 was supplied at the rate of 14953 g/hr from a transfer line 2. The liquid temperature inside reaction vessel 102 was controlled to 160° C. by a heater and a reboiler 112, and the pressure was adjusted to about 120 kPa-G with a pressure control valve. The residence time in the reaction vessel was about 17 minutes. 3-methyl-1-butanol containing water at the rate of 15037 g/hr from the top of the reaction vessel via a transfer line 6, and 3-methyl-1-butanol at the rate of 825 g/hr via feed line 1, were pumped to distillation column 101 packed with Metal Gauze CY Packing and provided with a reboiler 111 and a condenser 121 to carry out distillative purification. In the top of distillation column 101, a fraction containing a high concentration of water was condensed by condenser 121 and recovered from a recovery line 3. Purified 3-methyl-1-butanol was pumped to column-type reaction vessel 102 via transfer line 2 located in the lower portion of distillation column 101. An alkyl tin alkoxide catalyst composition containing di-n-butyl-bis(3-methylbutyloxy) tin and 1,1,3,3-tetra-n-butyl-1,3-bis(3-methylbutyloxy) distannoxane was obtained from the lower portion of column-type reaction vessel 102, and supplied to a thin film distillation apparatus 103 (Kobelco Eco-Solutions Co., Ltd., Japan) via a transfer line 5. The 3-methyl-1-butanol was distilled off in thin film distillation apparatus 103 and returned to column-type reaction vessel 102 via a condenser 123, a transfer line 8 and transfer line 4. The alkyl tin alkoxide catalyst composition was pumped from the lower portion of thin film distillation apparatus 103 via a transfer line 7 and supplied to an autoclave 104 while adjusting the flow rate of di-n-butyl-bis(3-methylbutyloxy) tin and 1,1,3,3-tetra-n-butyl-1,3-bis(3-methylbutyloxy) distannoxane to about 5130 g/hr. Carbon dioxide was supplied to the autoclave by a transfer line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing bis(3-methylbutyl) carbonate. This reaction liquid was transferred to a decarbonization tank 105 via a transfer line 10 and a control valve to remove residual carbon dioxide, and the carbon dioxide was recovered from a transfer line 11. Subsequently, the reaction liquid was transferred to a thin film distillation apparatus 106 (Kobelco Eco-Solutions Co., Ltd., Japan) set to about 142° C. and about 0.5 kPa via a transfer line 12 and supplied while adjusting the flow rate of 1,1,3,3-tetra-n-butyl-1,3-bis(3-methylbutyloxy) distannoxane to about 4388 g/hr to obtain a fraction containing bis(3-methylbutyl) carbonate. On the other hand, the evaporation residue was circulated to column-type reaction vessel 102 via transfer line 13 and transfer line 4 while adjusting the flow rate of 1,1,3,3-tetra-n-butyl-1,3-bis(3-methylbutyloxy) distannoxane to about 4388 g/hr. The fraction containing bis(3-methylbutyl) carbonate was supplied to a distillation column 107 packed with Metal Gauze CY packing and equipped with a reboiler 117 and a condenser 127 via a condenser 126 and a transfer line 14 at the rate of 959 g/hr followed by distillative purification to obtain 99 wt % bis(3-methylbutyl) carbonate from a recovery line 16 at the rate of 944 g/hr. When the alkyl tin alkoxide catalyst composition of a transfer line 13 was analyzed by $^{119}$Sn-, $^{1}$H- and $^{13}$C-NMR analysis, it was found to contain 1,1,3,3-tetra-n-butyl-1,3-bis(3-methylbutyloxy) distannoxane but not contain di-n-butyl-bis(3-methylbutyloxy) tin. After carrying out the above-mentioned continuous operation for about 240 hours, alkyl tin alkoxide catalyst composition was extracted from an extraction line 16 at the rate of 18 g/hr, while 1,1,3,3-tetra-n-butyl-1,3-bis(3-methylbutyloxy) distannoxane produced according to the above process was supplied from a feed line 17 at the rate of 18 g/hr.

Step (1-2): Production of N,N'-hexanediyl-bis-carbamic Acid Bis(3-methylbutyl) Ester 1537 g (7.6 mol) of bis(3-methylbutyl) carbonate obtained in step (1-1) and 220.8 g (1.9 mol) of hexamethylene diamine (Aldrich Corp., USA) were placed in a 5 L volumetric fourth-mouth flask, a stirrer was placed in the flask, and a Dimroth condenser and three-way valve were attached to the flask. After replacing the inside of the system with nitrogen, the flask was immersed in an oil bath (OBH-24, Masuda Corp., Japan) heated to 80° C. followed by the addition of 18.3 g of sodium methoxide (25% methanol solution, Aldrich Corp., USA) with a syringe to start the reaction. Samples of the reaction liquid were suitably collected and subjected to NMR analysis, and the reaction was terminated at the point hexamethylene diamine was no longer detected.

The resulting solution was housed in an acidic sulfonic acid ion exchange resin (Amberlyst-15, spherical, Rohm and Haas Co., USA) adjusted by removing the moisture and supplied to a column warmed to 65° C. by an external jacket to neutralize the sodium methoxide in the solution.

As a result of analyzing the solution by liquid chromatography, the solution was found to contain 36.7% by weight of N,N'-hexanediyl-bis-carbamic acid bis(3-methylbutyl) ester.

Step (1-3): Preparation of Composition

The solution obtained in step (1-2) and 2218 g of 2,4-di-tert-amylphenol (Tokyo Chemical Industry Co., Ltd., Japan) were mixed to obtain a homogeneous solution. The solution was supplied to a molecular distillation apparatus (MS-300, Sibata Scientific Technology, Ltd., Japan) at the rate of 300 g/Hr and low boiling point components were removed at a temperature of about 130° C. and pressure of about 0.13 kPa to obtain 1097 g of a distillate. As a result of analyzing by gas chromatography, the distillate was determined to be a solution containing 69.2% by weight of bis(3-methylbutyl) carbonate and 29.0% by weight of 3-methyl-1-butanol. In addition, when the distillation residue obtained in the flask was analyzed by liquid chromatography, the distillation residue was determined to contain 22.7% by weight of N,N'-hexanediyl-bis-carbamic acid bis(3-methylbutyl) ester, and the yield of N,N'-hexanediyl-bis-carbamic acid bis(3-methylbutyl) ester based on hexamethylene diamine was 98%. The composition had a stoichiometric ratio of N,N'-hexanediyl-bis-carbamic acid bis(3-methylbutyl) ester and 2,4-di-tert-amylphenol of 1:5.0. This composition was a liquid at 130° C., and after maintaining at 130° C. under a nitrogen atmosphere for 10 days, the concentration of N,N'-hexanediyl-bis-carbamic acid bis(3-methylbutyl) ester was 22.6% by weight.

Example 2

Step (2-1): Production of Bis(3-methylbutyl) Carbonate

Bis(3-methylbutyl) carbonate was produced using the same method as Step (1-1) of Example 1.

Step (2-2): Production of N,N'-hexanediyl-bis-carbamic Acid Bis(3-methylbutyl) Ester A solution containing 31.3% by weight of N,N'-hexanediyl-bis-carbamic acid bis(3-methylbutyl) ester was obtained by carrying out the same method as step (1-2) of Example 1 with the exception of using 2039 g (10.1 mol) of the bis(3-methylbutyl) carbonate obtained in step (2-1), using 244 g (2.1 mol) of hexamethylene diamine, and using 20.3 g of sodium methoxide (25% methanol solution).

Step (2-3): Production of Composition 1097 g of a distillate were obtained by carrying out the same method as step (1-3) of Example 1 with the exception of using the solution obtained in step (2-2) and 3560 g of 2-phenylphenol (Tokyo Chemical Industry Co., Ltd., Japan) instead of 2,4-di-tert-amylphenol. As a result of analyzing by gas chromatography, the distillate was found to be a solution containing 75.1% by weight of bis(3-methylbutyl) carbonate and 22.0% by weight of 3-methyl-1-butanol. In addition, as a result of analyzing by liquid chromatography, the distillation residue in the flask was found to contain 16.9% by weight of N,N'-hexanediyl-bis-carbamic acid bis(3-methylbutyl) ester, and the yield of N,N'-hexanediyl-bis-carbamic acid bis(3-methylbutyl) ester based on hexamethylene diamine was 97%. This solution was a composition in which the stoichiometric ratio of N,N'-hexanediyl-bis-carbamic acid bis(3-methylbutyl) ester and 2-phenylphenol was 1:9.9. This composition was a liquid at 130° C., and after maintaining at 130° C. under a nitrogen atmosphere for 10 days, the concentration of N,N'-hexanediyl-bis-carbamic acid bis(3-methylbutyl) ester was 16.9% by weight.

Example 3

Step (3-1): Production of Bis(3-methylbutyl) Carbonate

Bis(3-methylbutyl) carbonate was produced using the same method as Step (1-1) of Example 1.

Step (3-2): Production of N,N'-hexanediyl-bis-carbamic Acid Bis(3-methylbutyl) Ester A solution containing 28.4% by weight of N,N'-hexanediyl-bis-carbamic acid bis(3-methylbutyl) ester was obtained by carrying out the same method as step (1-2) of Example 1 with the exception of using 2630 g (13.0 mol) of the bis(3-methylbutyl) carbonate obtained in step (3-1), using 291 g (2.5 mol) of hexamethylene diamine, and using 24.1 g of sodium methoxide (25% methanol solution).

Step (3-3): Production of Composition 2068 g of a distillate were obtained by carrying out the same method as step (1-3) of Example 1 with the exception of using the solution obtained in step (3-2) and 2401 g of 2,4-bis(α,α-dimethylbenzyl)phenol (Tokyo Chemical Industry Co., Ltd., Japan) instead of 2,4-di-tert-amylphenol. As a result of analyzing by gas chromatography, the distillate was found to be a solution containing 79.3% by weight of bis(3-methylbutyl) carbonate and 20.3% by weight of 3-methyl-1-butanol. In addition, as a result of analyzing by liquid chromatography, the distillation residue in the flask was found to contain 25.5% by weight of N,N'-hexanediyl-bis-carbamic acid bis(3-methylbutyl) ester, and the yield of N,N'-hexanediyl-bis-carbamic acid bis(3-methylbutyl) ester based on hexamethylene diamine was 97%. This composition was a composition in which the stoichiometric ratio of N,N'-hexanediyl-bis-carbamic acid bis(3-methylbutyl) ester and 2,4-bis(α,α-dimethylbenzyl)phenol was 1:3.0. This composition was a liquid at 130° C., and after maintaining at 130° C. under a nitrogen atmosphere for 10 days, the concentration of N,N'-hexanediyl-bis-carbamic acid bis(3-methylbutyl) ester was 25.3% by weight.

Example 4

Step (4-1): Production of
N,N'-hexanediyl-bis-carbamic Acid Dimethyl Ester

A solution containing 33.4% by weight of N,N'-hexanediyl-bis-carbamic acid dimethyl ester was obtained by carrying out the same method as step (1-2) of Example 1 with the exception of using 1517 g (16.8 mol) of dimethyl carbonate (Aldrich Corp., USA) instead of bis(3-methylbutyl) carbonate, using 325 g (2.8 mol) of hexamethylene diamine, and using 5.4 g of sodium methoxide (25% methanol solution).

Step (4-2): Production of Composition 1326 g of a distillate were obtained by carrying out the same method as step (1-3) of Example 1 with the exception of using the solution obtained in step (4-1) and 6493 g of 2,6-xylenol (Tokyo Chemical Industry Co., Ltd., Japan) instead of 2,4-di-tert-amylphenol, and making the pressure inside the apparatus 13.1 kPa. As a result of analyzing by gas chromatography, the distillate was found to be a solution containing 77.9% by weight of dimethyl carbonate and 12.8% by weight of methanol. In addition, as a result of analyzing by liquid chromatography, the distillation residue obtained in the flask was found to contain 8.8% by weight of N,N'-hexanediyl-bis-carbamic acid dimethyl ester, and the yield of N,N'-hexanediyl-bis-carbamic acid dimethyl ester based on hexamethylene diamine was 95%. This solution was a composition in which the stoichiometric ratio of N,N'-hexanediyl-bis-carbamic acid dimethyl ester and 2,6-xylenol was 1:19.6. This composition was a liquid at 130° C., and after maintaining at 130° C. under a nitrogen atmosphere for 10 days, the concentration of N,N'-hexanediyl-bis-carbamic acid dimethyl ester was 8.8% by weight.

Example 5

Step (5-1): Production of
N,N'-hexanediyl-bis-carbamic Acid Dimethyl Ester

A solution containing 44.6% by weight of N,N'-hexanediyl-bis-carbamic acid dimethyl ester was obtained by carrying out the same method as step (1-2) of Example 1 with the exception of using 1113 g (12.3 mol) of dimethyl carbonate (Aldrich Corp., USA) instead of bis(3-methylbutyl) carbonate, using 325 g (2.8 mol) of hexamethylene diamine, and using 5.4 g of sodium methoxide (25% methanol solution).

Step (5-2): Production of Composition 1086 g of a distillate were obtained by carrying out the same method as step (1-3) of Example 1 with the exception of using the solution obtained in step (5-1) and 13915 g of 2,4,6-trimethyphenol (Aldrich Corp., USA) instead of 2,4-di-tert-amylphenol, and making the pressure inside the apparatus 13.1 kPa. As a result of analyzing by gas chromatography, the distillate was found to be a solution containing 54.4% by weight of dimethyl carbonate and 15.7% by weight of methanol. In addition, as a result of analyzing by liquid chromatography, the distillation residue obtained in the flask was found to contain 4.4% by weight of N,N'-hexanediyl-bis-carbamic acid dimethyl ester, and the yield of N,N'-hexanediyl-bis-carbamic acid dimethyl ester based on hexamethylene diamine was 96%. This solution was a composition in which the stoichiometric ratio of N,N'-hexanediyl-bis-carbamic acid dimethyl ester and 2,4,6-trimethylphenol was 1:37.1. This composition was a liquid at 130° C., and after maintaining at 130° C. under a nitrogen atmosphere for 10 days, the concentration of N,N'-hexanediyl-bis-carbamic acid dimethyl ester was 4.3% by weight.

Example 6

Step (6-1): Production of
N,N'-hexanediyl-bis-carbamic Acid Dimethyl Ester

A solution containing 22.5% by weight of N,N'-hexanediyl-bis-carbamic acid dimethyl ester was obtained by carrying out the same method as step (1-2) of Example 1 with the exception of using 1987 g (22.0 mol) of dimethyl carbonate instead of bis(3-methylbutyl) carbonate, using 256 g (2.2 mol) of hexamethylene diamine, and using 4.2 g of sodium methoxide (25% methanol solution).

Step (6-2): Production of Composition 2234 g of a distillate were obtained by carrying out the same method as step (1-3) of Example 1 with the exception of using the solution obtained in step (6-1) and 11092 g of 2-ethoxyphenol (Aldrich Corp., USA) instead of 2,4-di-tert-amylphenol, and making the pressure inside the apparatus 13.1 kPa. As a result of analyzing by gas chromatography, the distillate was found to be a solution containing 69.0% by weight of dimethyl carbonate and 5.9% by weight of methanol. In addition, as a result of analyzing by liquid chromatography, the distillation residue obtained in the flask was found to contain 4.5% by weight of N,N'-hexanediyl-bis-carbamic acid dimethyl ester, and the yield of N,N'-hexanediyl-bis-carbamic acid dimethyl ester based on hexamethylene diamine was 96%. This solution was a composition in which the stoichiometric ratio of N,N'-hexanediyl-bis-carbamic acid dimethyl ester and 2-ethoxyphenol was 1:36.1. This composition was a liquid at 130° C., and after maintaining at 130° C. under a nitrogen atmosphere for 15 days, the concentration of N,N'-hexanediyl-bis-carbamic acid dimethyl ester was 4.3% by weight.

Example 7

Step (7-1): Production of Dibutyl Carbonate 692 g (2.78 mol) of di-n-butyl tin oxide and 2000 g (27 mol) of 1-butanol (Wako Pure Chemical Industries, Ltd., Japan) were placed in a 3000 mL volumetric pear-shaped flask. The flask containing the mixture in the form of a white slurry was connected to an evaporator to which was connected an oil bath equipped with a temperature controller, a vacuum pump and a vacuum controller. The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to about 126° C., the flask was immersed in the oil bath and rotation of the evaporator was started. After stirring and heating for about 30 minutes at normal pressure with the purge valve of the evaporator left open, the mixture boiled and distillation of a low boiling point component began. After maintaining in this state for 8 hours, the purge valve was closed, pressure inside the system was gradually reduced, and remaining low boiling point component was distilled with the pressure inside the system at 76 to 54 kPa. After the low boiling point component no longer appeared, the flask was taken out of the oil bath. The reaction liquid had become a clear liquid. Subsequently, the flask was taken out of the oil bath, the purge valve was opened gradually and the pressure inside the system was returned to normal pressure. 952 g of reaction liquid were obtained in the flask. Based on the results of $^{119}$Sn-, $^{1}$H- and $^{13}$C-NMR analyses, the product 1,1,3,3-tetra-n-butyl-1,3-di(n-butyloxy) distannoxane was obtained at a yield of 99% based on di-n-butyl tin oxide. The same procedure was then repeated 12 times to obtain a total of 11480 g of 1,1,3,3-tetra-n-butyl-1,3-di(n-butyloxy) distannoxane.

Carbonic acid ester was produced in a continuous production apparatus like that shown in FIG. 1. 1,1,3,3-tetra-n-butyl-1,3-di(n-butyloxy) distannoxane produced in the manner described above was supplied at the rate of 4201 g/hr from a feed line 4 into a column-type reaction vessel 102 packed with Mellapak 750Y Packing (Sulzer Chemtech Ltd., Switzerland) and having an inner diameter of 151 mm and effective length of 5040 mm, and 1-butanol purified with a distillation column 101 was supplied at the rate of 24717 g/hr from a feed line 2. The liquid temperature inside reaction vessel 102 was controlled to 160° C. by a heater and a reboiler 112, and the pressure was adjusted to about 250 kPa-G with a pressure control valve. The residence time in the reaction vessel was about 10 minutes. 1-Butanol containing water at the rate of 24715 g/hr from the top of the reaction vessel via a transfer line 6, and 1-butanol at the rate of 824 g/hr via feed line 1, were pumped to distillation column 101 packed with Metal Gauze CY Packing (Sulzer Chemtech Ltd., Switzerland) and provided with reboiler 111 and condenser 121 to carry out distillative purification. In the top of distillation column 101, a fraction containing a high concentration of water was condensed by condenser 121 and recovered from a transfer line 3. Purified 1-butanol was pumped via transfer line 2 located in the lower portion of distillation column 101. An alkyl tin alkoxide catalyst composition containing di-n-butyl-tin-di-n-butoxide and 1,1,3,3-tetra-n-butyl-1,3-di(n-butyloxy) distannoxane was obtained from the lower portion of column-type reaction vessel 102, and supplied to a thin film distillation apparatus 103 (Kobelco Eco-Solutions Co., Ltd., Japan) via a transfer line 5. The 1-butanol was distilled off in thin film distillation apparatus 103 and returned to column-type reaction vessel 102 via condenser 123, transfer line 8 and transfer line 4. The alkyl tin alkoxide catalyst composition was pumped from the lower portion of thin film distillation apparatus 103 via transfer line 7 and supplied to autoclave 104 while adjusting the flow rate of the active components in the form of dibutyl tin dibutoxide and 1,1,3,3-tetra-n-butyl-1,3-di(n-butyloxy) distannoxane to about 4812 g/hr. Carbon dioxide was supplied to the autoclave by a feed line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing dibutyl carbonate. This reaction liquid was transferred to decarbonization tank 105 via transfer line 10 and a control valve to remove residual carbon dioxide, and the carbon dioxide was recovered from transfer line 11. Subsequently, the reaction liquid was pumped to thin film distillation apparatus 106 (Kobelco Eco-Solutions Co., Ltd., Japan) set to about 140° C. and about 1.4 kPa via transfer line 12 and supplied while adjusting the flow rate of 1,1,3,3-tetra-n-butyl-1,3-di(n-butyloxy) distannoxane to about 4201 g/hr to obtain a fraction containing dibutyl carbonate. On the other hand, the evaporation residue was circulated column-type reaction vessel 102 via transfer line 13 and transfer line 4 while adjusting the flow rate of 1,1,3,3-tetra-n-butyl-1,3-di(n-butyloxy) distannoxane to about 4201 g/hr. The fraction containing dibutyl carbonate was supplied to distillation column 107 packed with Metal Gauze CY packing (Sulzer Chemtech Ltd., Switzerland) and equipped with reboiler 117 and condenser 127 via condenser 126 and transfer line 14 at the rate of 830 g/hr followed by distillative purification to obtain 99% by weight dibutyl carbonate from transfer line 16 at the rate of 814 g/hr. When the alkyl tin alkoxide catalyst composition of transfer line 13 was analyzed by $^{119}$Sn-, $^{1}$H- and $^{13}$C-NMR analysis, it was found to contain 1,1,3,3-tetra-n-butyl-1,3-di(n-butyloxy) distannoxane but not contain di-n-butyl tin-di-n-butoxide. After carrying out the above-mentioned continuous operation for about 600 hours, alkyl tin alkoxide catalyst composition was extracted from extraction line 16 at the rate of 16 g/hr, while 1,1,3,3-tetra-n-butyl-1,3-di(n-butyloxy) distannoxane produced according to the above process was supplied from feed line 17 at the rate of 16 g/hr.

Step (7-2): Production of
N,N'-hexanediyl-bis-carbamic Acid Dibutyl Ester

A solution containing 18.7% by weight of N,N'-hexanediyl-bis-carbamic acid dibutyl ester was obtained by carrying out the same method as step (1-2) of Example 1 with the exception of using 2760 g (15.8 mol) of dibutyl carbonate obtained in step (7-1) instead of bis(3-methylbutyl) carbonate, using 209 g (1.8 mol) of hexamethylene diamine, and using 10.4 g of sodium methoxide (25% methanol solution).

Step (7-3): Production of Composition 2241 g of a distillate were obtained by carrying out the same method as step (1-3) of Example 1 with the exception of using the solution obtained in step (7-2) and 3957 g of 2,6-dimethoxyphenol (Aldrich Corp., USA) instead of 2,4-di-tert-amylphenol, and making the pressure inside the apparatus 13.1 kPa. As a result of analyzing by gas chromatography, the distillate was found to be a solution containing 85.1% by weight of dibutyl carbonate and 5.4% by weight of 1-butanol. In addition, as a result of analyzing by liquid chromatography, the distillation residue obtained in the flask was found to contain 12.3% by weight of N,N'-hexanediyl-bis-carbamic acid dibutyl ester, and the yield of N,N'-hexanediyl-bis-carbamic acid dibutyl ester based on hexamethylene diamine was 95%. This solution was a composition in which the stoichiometric ratio of N,N'-hexanediyl-bis-carbamic acid dibutyl ester and 2,6-dimethoxyphenol was 1:14.1. This composition was a liquid at 130° C., and after maintaining at 130° C. under a nitrogen atmosphere for 12 days, the concentration of N,N'-hexanediyl-bis-carbamic acid dibutyl ester was 12.3% by weight.

Example 8

Step (8-1): Production of Dibutyl Carbonate

Dibutyl carbonate was produced using the same method as step (7-1) of Example 7.

Step (8-2): Production of N,N'-hexanediyl-bis-carbamic Acid Dibutyl Ester

A solution containing 28.8% by weight of N,N'-hexanediyl-bis-carbamic acid dibutyl ester was obtained by carrying out the same method as step (1-2) of Example 1 with the exception of using 1821 g (10.5 mol) of dibutyl carbonate obtained in step (8-1) instead of bis(3-methylbutyl) carbonate, using 221 g (1.9 mol) of hexamethylene diamine, and using 11.0 g of sodium methoxide (25% methanol solution).

Step (8-3): Production of Composition 1488 g of a distillate were obtained by carrying out the same method as step (1-3) of Example 1 with the exception of using the solution obtained in step (8-2) and 8710 g of 4-nonylphenol (Aldrich Corp., USA) instead of 2,4-di-tert-amylphenol, and making the pressure inside the apparatus 13.1 kPa. As a result of analyzing by gas chromatography, the distillate was found to be a solution containing 75.2% by weight of dibutyl carbonate and 17.7% by weight of 1-butanol. In addition, as a result of analyzing by liquid chromatography, the distillation residue obtained in the flask was found to contain 6.2% by weight of N,N'-hexanediyl-bis-carbamic acid dibutyl ester, and the yield of N,N'-hexanediyl-bis-carbamic acid dibutyl ester based on hexamethylene diamine was 83%. This solution was a composition in which the stoichiometric ratio of N,N'-hexanediyl-bis-carbamic acid dibutyl ester and 4-nonylphenol was 1:24.7. This composition was a liquid at 70° C., and after maintaining at 70° C. under a nitrogen atmosphere for 70 days, the concentration of N,N'-hexanediyl-bis-carbamic acid dibutyl ester was 6.2% by weight.

Example 9

Step (9-1): Production of Bis(3-methylbutyl) Carbonate

Bis(3-methylbutyl) carbonate was produced using the same method as step (1-1) of Example 1.

Step (9-2): Production of 3-((3-methylbutyl)oxycarbonylamino-methyl)-3,5,5-trimethylcyclohexylcarbamic Acid (3-methylbutyl) Ester 2549 g (12.6 mol) of bis(3-methylbutyl) carbonate obtained in step (9-1) and 358 g (2.1 mol) of 3-aminomethyl-3,5,5-trimethylcyclohexylamine (Aldrich Corp., USA) were placed in a 5 L volumetric fourth-mouth flask, a stirrer was placed in the flask, and a Dimroth condenser and three-way valve were attached to the flask. After replacing the inside of the system with nitrogen, the flask was immersed in an oil bath (OBH-24, Masuda Corp., Japan) heated to 80° C. followed by the addition of 20.3 g of sodium methoxide (25% methanol solution) with a syringe to start the reaction. Samples of the reaction liquid were suitably collected and subjected to NMR analysis, and the reaction was terminated at the point 3-aminomethyl-3,5,5-trimethylcyclohexylamine was no longer detected.

The resulting solution was housed in a basic sulfonic acid ion exchange resin (Amberlyst-15, spherical, Rohm and Haas Co., USA) adjusted by removing the moisture and supplied to a column warmed to 65° C. by an external jacket to neutralize the sodium methoxide in the solution.

As a result of analyzing the solution by liquid chromatography, the solution was found to contain 28.2% by weight of 3-((3-methylbutyl)oxycarbonylamino-methyl)-3,5,5-trimethylcyclohexylcarbamic acid (3-methylbutyl) ester.

Step (9-3): Preparation of Composition

The solution obtained in step (9-2) and 4654 g of 2,4-di-tert-amylphenol were mixed to obtain a homogeneous solution. The solution was supplied to a molecular distillation apparatus (MS-300, Sibata Scientific Technology, Ltd., Japan) at the rate of 300 g/Hr and low boiling point components were removed at a temperature of about 130° C. and pressure of about 0.13 kPa to obtain 2398 g of a distillate. As a result of analyzing by gas chromatography, the distillate was determined to be a solution containing 68.4% by weight of bis(3-methylbutyl) carbonate and 14.3% by weight of 3-methyl-1-butanol. In addition, when the distillation residue obtained in the flask was analyzed by liquid chromatography, the distillation residue was determined to contain 15.6% by weight of 3-((3-methylbutyl) oxycarbonylamino-methyl)-3,5,5-trimethylcyclohexylcarbamic acid (3-methylbutyl) ester and the yield of 3-((3-methylbutyl)oxycarbonylamino-methyl)-3,5,5-trimethylcyclohexylcarbamic acid (3-methylbutyl) ester based on 3-aminomethyl-3,5,5-trimethylcyclohexylamine was 96%. The composition had a stoichiometric ratio of 3-((3-methylbutyl)oxycarbonylamino-methyl)-3,5,5-trimethylcyclohexylcarbamic acid (3-methylbutyl) ester and 2,4-di-tert-amylphenol of 1:9.1. This composition was a liquid at 80° C., and after maintaining at 80° C. under a nitrogen atmosphere for 100 days, the concentration of 3-((3-methylbutyl)oxycarbonylamino-methyl)-3,5,5-trimethylcyclohexylcarbamic acid (3-methylbutyl) ester was 15.5% by weight.

Example 10

Step (10-1): Production of Bis(3-methylbutyl) Carbonate

Bis(3-methylbutyl) carbonate was produced using the same method as step (1-1) of Example 1.

Step (10-2): Production of 3-((3-methylbutyl)oxycarbonylamino-methyl)-3,5,5-trimethylcyclohexylcarbamic Acid (3-methylbutyl) Ester A solution containing 33.0% by weight of 3-((3-methylbutyl)oxycarbonylamino-methyl)-3,5,5-trimethylcyclohexylcarbamic acid (3-methylbutyl) ester was obtained by carrying out the same method as step (9-2) of Example 9 with the exception of using 2124 g (10.5 mol) of the bis(3-methylbutyl) carbonate obtained in step (10-1), using 358 g (2.1 mol) of 3-aminomethyl-3,5,5-trimethylcyclohexylamine, and using 20.3 g of sodium methoxide (25% methanol solution).

Step (10-3): Production of Composition 1618 g of a distillate were obtained by carrying out the same method as step (9-3) of Example 9 with the exception of using the solution obtained in step (10-2) and 2625 g of 2,4-bis(α,α-dimethylbenzyl)phenol instead of 2,4-di-tert-amylphenol. As a result of analyzing by gas chromatography, the distillate was found to be a solution containing 76.1% by weight of bis(3-methylbutyl) carbonate and 21.5% by weight of 3-methyl-1-butanol. In addition, as a result of analyzing by liquid chromatography, the distillation residue in the flask was found to contain 23.2% by weight of 3-((3-methylbutyl)oxycarbonylamino-methyl)-3,5,5-trimethylcyclohexylcarbamic acid (3-methylbutyl) ester, and the yield of 3-((3-methylbutyl)oxycarbonylamino-methyl)-3,5,5-trimethylcyclohexylcarbamic acid (3-methylbutyl) ester based on 3-aminomethyl-3,5,5-trimethylcyclohexylamine was 95%. This solution was a composition in which the stoichiometric ratio of 3-((3-methylbutyl)oxycarbonylamino-methyl)-3,5,5-trimethylcyclohexylcarbamic acid (3-methylbutyl) ester and 2,4-bis(α,α-dimethylbenzyl)phenol was 1:3.9. This composition was a liquid at 170° C., and after maintaining at 170° C. under a nitrogen atmosphere for 3 days, the concentration of 3-((3-methylbutyl)oxycarbonylamino-methyl)-3,5,5-trimethylcyclohexylcarbamic acid (3-methylbutyl) ester was 23.1% by weight.

Example 11

Step (11-1): Production of 3-(methyloxycarbonylamino-methyl)-3,5,5-trimethylcyclohexylcarbamic Acid Methyl Ester A solution containing 38.2% by weight of 3-(methyloxycarbonylamino-methyl)-3,5,5-trimethylcyclohexylcarbamic acid methyl ester was obtained by carrying out the same method as step (9-2) of Example 9 with the exception of using 1820 g (20.2 mol) of dimethyl carbonate instead of bis(3-methylbutyl) carbonate, using 545 g (3.2 mol) of 3-aminomethyl-3,5,5-trimethylcyclohexylamine, and using 12.3 g of sodium methoxide (25% methanol solution).

Step (11-2): Production of Composition 2027 g of a distillate were obtained by carrying out the same method as step (9-3) of Example 9 with the exception of using the solution obtained in step (11-1) and 16270 g of 2,6-xylenol instead of 2,4-di-tert-amylphenol, and making the pressure inside the apparatus 13.1 kPa. As a result of analyzing by gas chromatography, the distillate was found to be a solution containing 59.0% by weight of dimethyl carbonate and 9.6% by weight of methanol. In addition, as a result of analyzing by liquid chromatography, the distillation residue obtained in the flask was found to contain 5.1% by weight of 3-(methyloxycarbonylamino-methyl)-3,5,5-trimethylcyclohexylcarbamic acid methyl ester, and the yield of 3-(methyloxycarbonylamino-methyl)-3,5,5-trimethylcyclohexylcarbamic acid methyl ester based on 3-aminomethyl-3,5,5-trimethylcyclohexylamine was 95%. This solution was a composition in which the stoichiometric ratio of 3-(methyloxycarbonylamino-methyl)-3,5,5-trimethylcyclohexylcarbamic acid methyl ester and 2,6-xylenol was 1:43.3. This composition was a liquid at 130° C., and after maintaining at 130° C. under a nitrogen atmosphere for 10 days, the concentration of 3-(methyloxycarbonylamino-methyl)-3,5,5-trimethylcyclohexylcarbamic acid methyl ester was 5.1% by weight.

Example 12

Step (12-1): Production of 3-(methyloxycarbonylamino-methyl)-3,5,5-trimethylcyclohexylcarbamic Acid Methyl Ester A solution containing 46.7% by weight of 3-(methyloxycarbonylamino-methyl)-3,5,5-trimethylcyclohexylcarbamic acid methyl ester was obtained by carrying out the same method as step (9-2) of Example 9 with the exception of using 1214 g (13.4 mol) of dimethyl carbonate instead of bis(3-methylbutyl) carbonate, using 478 g (2.8 mol) of 3-aminomethyl-3,5,5-trimethylcyclohexylamine, and using 10.8 g of sodium methoxide (25% methanol solution).

Step (12-2): Production of Composition 1427 g of a distillate were obtained by carrying out the same method as step (9-3) of Example 9 with the exception of using the solution obtained in step (12-1) and 11960 g of 2,4,6-trimethylphenol instead of 2,4-di-tert-amylphenol, and making the pressure inside the apparatus 13.1 kPa. As a result of analyzing by gas chromatography, the distillate was found to be a solution containing 71.2% by weight of dimethyl carbonate and 17.1% by weight of methanol. In addition, as a result of analyzing by liquid chromatography, the distillation residue obtained in the flask was found to contain 6.0% by weight of 3-(methyloxycarbonylamino-methyl)-3,5,5-trimethylcyclohexylcarbamic acid methyl ester, and the yield of 3-(methyloxycarbonylamino-methyl)-3,5,5-trimethylcyclohexylcarbamic acid methyl ester based on 3-aminomethyl-3,5,5-trimethylcyclohexylamine was 94%. This solution was a composition in which the stoichiometric ratio of 3-(methyloxycarbonylamino-methyl)-3,5,5-trimethylcyclohexylcarbamic acid methyl ester and 2,4,6-trimethylphenol was 1:32.7. This composition was a liquid at 150° C., and after maintaining at 150° C. under a nitrogen atmosphere for 2 days, the concentration of 3-(methyloxycarbonylamino-methyl)-3,5,5-trimethylcyclohexylcarbamic acid methyl ester was 6.0% by weight.

Example 13

Step (13-1): Production of Dibutyl Carbonate

Dibutyl carbonate was produced using the same method as step (7-1) of Example 7.

Step (13-2): Production of 3-(butyloxycarbonylamino-methyl)-3,5,5-trimethylcyclohexylcarbamic Acid Butyl Ester A solution containing 35.6% by weight of 3-(butyloxycarbonylamino-methyl)-3,5,5-trimethylcyclohexylcarbamic acid butyl ester was obtained by carrying out the same method as step (9-2) of Example 9 with the exception of using 2342 g (13.4 mol) of the dibutyl carbonate obtained in step (13-1), using 477 g (2.8 mol) of 3-aminomethyl-3,5,5-trimethylcyclohexylamine, and using 20.3 g of sodium methoxide (25% methanol solution).

Step (13-3): Production of Composition 1633 g of a distillate were obtained by carrying out the same method as step (9-3) of Example 9 with the exception of using the solution obtained in step (13-2) and 5805 g of 4-nonylphenol instead of 2,4-di-tert-amylphenol. As a result of analyzing by gas chromatography, the distillate was found to be a solution containing 82.6% by weight of dibutyl carbonate and 10.4% by weight of 1-butanol. In addition, as a result of analyzing by liquid chromatography, the distillation residue in the flask was found to contain 14.1% by weight of 3-(butyloxycarbonylamino-methyl)-3,5,5-trimethylcyclohexylcarbamic acid butyl ester and the yield of 3-((butyloxycarbonylamino-methyl)-3,5,5-trimethylcyclohexylcarbamic acid butyl ester based on 3-aminomethyl-3,5,5-trimethylcyclohexylamine was 90%. This solution was a composition in which the stoichiometric ratio of 3-(butyloxycarbonylamino-methyl)-3,5,5-trimethylcyclohexylcarbamic acid butyl ester and 4-nonylphenol was 1:10.2. This composition was a liquid at 30° C., and after maintaining at 30° C. under a nitrogen atmosphere for 100 days, the concentration of 3-(butyloxycarbonylamino-methyl)-3,5,5-trimethylcyclohexylcarbamic acid butyl ester was 13.9% by weight.

Example 14

Step (14-1): Production of Dibutyl Carbonate

Dibutyl carbonate was produced using the same method as step (7-1) of Example 7.

Step (14-2): Production of 3-(butyloxycarbonylamino-methyl)-3,5,5-trimethylcyclohexylcarbamic Acid Butyl Ester A solution containing 28.3% by weight of 3-(butyloxycarbonylamino-methyl)-3,5,5-trimethylcyclohexylcarbamic acid butyl ester was obtained by carrying out the same method as step (9-2) of Example 9 with the exception of using 3403 g (19.5 mol) of the dibutyl carbonate obtained in step (14-1), using 528 g (3.1 mol) of 3-aminomethyl-3,5,5-trimethylcyclohexylamine, and using 12.0 g of sodium methoxide (25% methanol solution).

Step (14-3): Production of Composition 2814 g of a distillate were obtained by carrying out the same method as step (9-3) of Example 9 with the exception of using the solution obtained in step (14-2) and 9443 g of 2,4-dimethoxyphenol instead of 2,4-di-tert-amylphenol. As a result of analyzing by gas chromatography, the distillate was found to be a solution containing 81.0% by weight of dibutyl carbonate and 15.3% by weight of 1-butanol. In addition, as a result of analyzing by liquid chromatography, the distillation residue in the flask was found to contain 10.3% by weight of 3-(butyloxycarbonylamino-methyl)-3,5,5-trimethylcyclohexylcarbamic acid butyl ester and the yield of 3-((butyloxycarbonylamino-methyl)-3,5,5-trimethylcyclohexylcarbamic acid butyl ester based on 3-aminomethyl-3,5,5-trimethylcyclohexylamine was 94.1%. This solution was a composition in which the stoichiometric ratio of 3-(butyloxycarbonylamino-methyl)-3,5,5-trimethylcyclohexylcarbamic acid butyl ester and 2,4-dimethoxyphenol was 1:20.8. This composition was a liquid at 30° C., and after maintaining at 30° C. under a nitrogen atmosphere for 90 days, the concentration of 3-(butyloxycarbonylamino-methyl)-3,5,5-trimethylcyclohexylcarbamic acid butyl ester was 10.0% by weight.

Example 15

Step (15-1): Production of Dibutyl Carbonate

Dibutyl carbonate was produced using the same method as step (7-1) of Example 7.

Step (15-2): Production of Dibutyl-4,4'-methylene-dicyclohexylcarbamate 2305 g (13.2 mol) of dibutyl carbonate obtained in step (15-1) and 442 g (2.1 mol) of 4,4'-methylenebis(cyclohexylamine) (Aldrich Corp., USA) were placed in a 5 L volumetric fourth-mouth flask, a stirrer was placed in the flask, and a Dimroth condenser and three-way valve were attached to the flask. After replacing the inside of the system with nitrogen, the flask was immersed in an oil bath heated to 80° C. followed by the addition of 20.3 g of sodium methoxide (25% methanol solution) with a syringe to start the reaction. Samples of the reaction liquid were suitably collected and subjected to NMR analysis, and the reaction was terminated at the point 4,4'-methylenebis(cyclohexylamine) was no longer detected.

The resulting solution was housed in a basic sulfonic acid ion exchange resin (Amberlyst-15, spherical, Rohm and Haas Co., USA) adjusted by removing the moisture and supplied to a column warmed to 65° C. by an external jacket to neutralize the sodium methoxide in the solution.

As a result of analyzing the solution by liquid chromatography, the solution was found to contain 30.8% by weight of dibutyl-4,4'-methylene-dicyclohexylcarbamate.

Step (15-3): Preparation of Composition

The solution obtained in step (15-2) and 6023 g of 2-tert-amylphenol were mixed to obtain a homogeneous solution. The solution was supplied to a molecular distillation apparatus (MS-300, Sibata Scientific Technology, Ltd., Japan) at the rate of 300 g/Hr and low boiling point components were removed at a temperature of about 130° C. and pressure of about 0.13 kPa to obtain 1977 g of a distillate. As a result of analyzing by gas chromatography, the distillate was determined to be a solution containing 78.2% by weight of dibutyl carbonate and 15.2% by weight of 1-butanol. In addition, when the distillation residue obtained in the flask was analyzed by liquid chromatography, the distillation residue was determined to contain 12.4% by weight of dibutyl-4,4'-methylene-dicyclohexylcarbamate and the yield of dibutyl-4,4'-methylene-dicyclohexylcarbamate based on 4,4'-methylenebis(cyclohexylamine) was 97%. The composition had a stoichiometric ratio of dibutyl-4,4'-methylene-dicyclohexylcarbamate and 2-tert-amylphenol of 1:17.6. This composition was a liquid at 30° C., and after maintaining at 30° C. under a nitrogen atmosphere for 85 days, the concentration of dibutyl-4,4'-methylene-dicyclohexylcarbamate was 12.2% by weight.

Example 16

Step (16-1): Production of Bis(3-methylbutyl) Carbonate

Bis(3-methylbutyl) carbonate was produced using the same method as step (1-1) of Example 1.

Step (16-2): Production of Bis(3-methylbutyl)-4,4'-methylene-dicyclohexyl Carbamate A solution containing 34.7% by weight of bis(3-methylbutyl)-4,4'-methylene-dicyclohexyl carbamate was obtained by carrying out the same method as step (15-2) of Example 15 with the exception of using 2270 g (11.2 mol) of bis(3-methylbutyl) carbonate instead of dibutyl carbonate, using 463 g (2.2 mol) of 4,4'-methylenebis(cyclohexylamine) (Aldrich Corp., USA), and using 21.2 g of sodium methoxide (25% methanol solution).

Step (16-3): Production of Composition 1775 g of a distillate were obtained by carrying out the same method as step (15-3) of Example 15 with the exception of using the solution obtained in step (16-2) and using 2476 g of 2,4-di-tert-amylphenol instead of 2-tert-amylphenol. As a result of analyzing by gas chromatography, the distillate was found to be a solution containing 75.7% by weight of bis(3-methylbutyl) carbonate and 16.9% by weight of 3-methyl-1-butanol. In addition, as a result of analyzing by liquid chromatography, the distillation residue obtained in the flask was found to contain 27.5% by weight of bis(3-methylbutyl)-4,4'-methylene-dicyclohexyl carbamate, and the yield of bis(3-methylbutyl)-4,4'-methylene-dicyclohexyl carbamate based on 4,4'-methylenebis(cyclohexylamine) was 96%. This solution was a composition in which the stoichiometric ratio of bis(3-methylbutyl)-4,4'-methylene-dicyclohexyl carbamate and 2,4-di-tert-amylphenol was 1:4.7. This composition was a liquid at 30° C., and after maintaining at 30° C. under a nitrogen atmosphere for 85 days, the concentration of bis(3-methylbutyl)-4,4'-methylene-dicyclohexyl carbamate was 27.2% by weight.

Example 17

Step (17-1): Production of Dimethyl-4,4'-methylene-dicyclohexyl Carbamate

A solution containing 48.3% by weight of dimethyl-4,4'-methylene-dicyclohexyl carbamate was obtained by carrying out the same method as step (15-2) of Example 15 with the exception of using 1150 g (12.7 mol) of dimethyl carbonate instead of dibutyl carbonate, using 547 g (2.6 mol) of 4,4'-methylenebis(cyclohexylamine) (Aldrich Corp., USA), and using 25.1 g of sodium methoxide (25% methanol solution).

Step (17-2): Production of Composition 1045 g of a distillate were obtained by carrying out the same method as step (15-3) of Example 15 with the exception of using the solution obtained in step (17-1) and using 5287 g of 2,4-diisopropylphenol instead of 2-tert-amylphenol. As a result of analyzing by gas chromatography, the distillate was found to be a solution containing 63.8% by weight of dimethyl carbonate and 15.1% by weight of methanol. In addition, as a result of analyzing by liquid chromatography, the distillation residue obtained in the flask was found to contain 13.6% by weight of dimethyl-4,4'-methylene-dicyclohexyl carbamate, and the yield of dimethyl-4,4'-methylene-dicyclohexyl carbamate based on 4,4'-methylenebis(cyclohexylamine) was 95%. This solution was a composition in which the stoichiometric ratio of dimethyl-4,4'-methylene-dicyclohexyl carbamate and 2,4-diisopropylphenol was 1:11.5. This composition was a liquid at 30° C., and after maintaining at 30° C. under a nitrogen atmosphere for 98 days, the concentration of dimethyl-4,4'-methylene-dicyclohexyl carbamate was 13.2% by weight.

Example 18

Step (18-1): Production of Dimethyl-4,4'-methylene-dicyclohexyl Carbamate

A solution containing 42.6% by weight of dimethyl-4,4'-methylene-dicyclohexyl carbamate was obtained by carrying out the same method as step (15-2) of Example 15 with the exception of using 1625 g (18.0 mol) of dimethyl carbonate instead of dibutyl carbonate, using 631 g (3.0 mol) of 4,4'-methylenebis(cyclohexylamine) (Aldrich Corp., USA), and using 17.4 g of sodium methoxide (25% methanol solution).

Step (18-2): Production of Composition 1699 g of a distillate were obtained by carrying out the same method as step (15-3) of Example 15 with the exception of using the solution obtained in step (18-1) and using 9600 g of 2,6-xylenol instead of 2-tert-amylphenol. As a result of analyzing by gas chromatography, the distillate was found to be a solution containing 62.6% by weight of dimethyl carbonate and 10.9% by weight of methanol. In addition, as a result of analyzing by liquid chromatography, the distillation residue obtained in the flask was found to contain 9.4% by weight of dimethyl-4,4'-methylene-dicyclohexyl carbamate, and the yield of dimethyl-4,4'-methylene-dicyclohexyl carbamate based on 4,4'-methylenebis(cyclohexylamine) was 97%. This solution was a composition in which the stoichiometric ratio of dimethyl-4,4'-methylene-dicyclohexyl carbamate and 2,6-xylenol was 1:25.7. This composition was a liquid at 130° C., and after maintaining at 130° C. under a nitrogen atmosphere for 3 days, the concentration of dimethyl-4,4'-methylene-dicyclohexyl carbamate was 9.2% by weight.

Example 19

Step (19-1): Production of Bis(3-methylbutyl) Carbonate

Bis(3-methylbutyl) carbonate was produced using the same method as step (1-1) of Example 1.

Step (19-2): Production of Bis(3-methylbutyl)-4,4'-methylene-dicyclohexyl Carbamate A solution containing 29.5% by weight of bis(3-methylbutyl)-4,4'-methylene-dicyclohexyl carbamate was obtained by carrying out the same method as step (15-2) of Example 15 with the exception of using 3010 g (14.9 mol) of bis(3-methylbutyl) carbonate obtained in step (19-1) instead of dibutyl carbonate, using 505 g (2.4 mol) of 4,4'-methylenebis(cyclohexylamine), and using 23.1 g of sodium methoxide (25% methanol solution).

Step (19-3): Production of Composition 2511 g of a distillate were obtained by carrying out the same method as step (15-3) of Example 15 with the exception of using the solution obtained in step (19-2) and using 5492 g of 2-phenylphenol instead of 2-tert-amylphenol. As a result of analyzing by gas chromatography, the distillate was found to be a solution containing 79.0% by weight of bis(3-methylbutyl) carbonate and 16.1% by weight of 3-methyl-1-butanol. In addition, as a result of analyzing by liquid chromatography, the distillation residue obtained in the flask was found to contain 15.0% by weight of bis(3-methylbutyl)-4,4'-methylene-dicyclohexyl carbamate, and the yield of bis(3-methylbutyl)-4,4'-methylene-dicyclohexyl carbamate based on 4,4'-methylenebis(cyclohexylamine) was 91.2%. This solution was a composition in which the stoichiometric ratio of bis(3-methylbutyl)-4,4'-methylene-dicyclohexyl carbamate and 2-phenylphenol was 1:14.1. This composition was a liquid at 150° C., and after maintaining at 150° C. under a nitrogen atmosphere for 1 day, the concentration of bis(3-methylbutyl)-4,4'-methylene-dicyclohexyl carbamate was 13.3% by weight.

Example 20

Step (20-1): Production of Dibutyl Carbonate

Dibutyl carbonate was produced using the same method as step (7-1) of Example 7.

Step (20-2): Production of Dibutyl-4,4'-methylene-dicyclohexyl Carbamate

A solution containing 33.0% by weight of dibutyl-4,4'-methylene-dicyclohexyl carbamate was obtained by carrying out the same method as step (15-2) of Example 15 with the exception of using 3133 g (18.0 mol) of dibutyl carbonate obtained in step (20-1), using 652 g (3.1 mol) of 4,4'-methylenebis(cyclohexylamine), and using 29.9 g of sodium methoxide (25% methanol solution).

Step (20-3): Production of Composition 2533 g of a distillate were obtained by carrying out the same method as step (15-3) of Example 15 with the exception of using the solution obtained in step (20-2) and using 4025 g of 4-tert-butylphenol instead of 2-tert-amylphenol. As a result of analyzing by gas chromatography, the distillate was found to be a solution containing 78.8% by weight of dibutyl carbonate and 17.4% by weight of 1-butanol. In addition, as a result of analyzing by liquid chromatography, the distillation residue obtained in the flask was found to contain 21.4% by weight of dibutyl-4,4'-methylene-dicyclohexyl carbamate, and the yield of dibutyl-4,4'-methylene-dicyclohexyl carbamate based on 4,4'-methylenebis(cyclohexylamine) was 87.4%. This solution was a composition in which the stoichiometric ratio of dibutyl-4,4'-methylene-dicyclohexyl carbamate and 4-tert-butylphenol was 1:9.7. This composition was a liquid at 100° C., and after maintaining at 100° C. under a nitrogen atmosphere for 30 days, the concentration of dibutyl-4,4'-methylene-dicyclohexyl carbamate was 21.0% by weight.

Example 21

Step (21-1): Production of Bis(3-methylbutyl) Carbonate

Bis(3-methylbutyl) carbonate was produced using the same method as step (1-1) of Example 1.

Step (21-2): Production of Toluene-2,4-Dicarbamic Acid Bis(3-methylbutyl) Ester 1529 g (7.6 mol) of bis(3-methylbutyl) carbonate obtained in step (21-1) and 257 g (2.1 mol) of 2,4-toluenediamine (Aldrich Corp., USA) were placed in a 5 L volumetric fourth-mouth flask, a stirrer was placed in the flask, and a Dimroth condenser and three-way valve were attached to the flask. After replacing the inside of the system with nitrogen, the flask was immersed in an oil bath heated to 80° C. followed by the addition of 28.4 g of sodium methoxide (25% methanol solution) with a syringe to start the reaction. Samples of the reaction liquid were suitably collected and subjected to NMR analysis, and the reaction was terminated at the point 2,4-toluenediamine was no longer detected.

The resulting solution was housed in a basic sulfonic acid ion exchange resin (Amberlyst-15, spherical, Rohm and Haas Co., USA) adjusted by removing the moisture and supplied to a column warmed to 65° C. by an external jacket to neutralize the sodium methoxide in the solution.

As a result of analyzing the solution by liquid chromatography, the solution was found to contain 39.8% by weight of toluene-2,4-dicarbamic acid bis(3-methylbutyl) ester.

Step (21-3): Preparation of Composition

The solution obtained in step (21-2) and 5411 g of 2,6-xylenol were mixed to obtain a homogeneous solution. The solution was supplied to a molecular distillation apparatus (MS-300, Sibata Scientific Technology, Ltd., Japan) at the rate of 300 g/Hr and low boiling point components were removed at a temperature of about 130° C. and pressure of about 0.13 kPa to obtain 1461 g of a distillate. As a result of analyzing by gas chromatography, the distillate was determined to be a solution containing 46.4% by weight of bis(3-methylbutyl) carbonate and 23.9% by weight of 3-methyl-1-butanol. In addition, when the distillation residue obtained in the flask was analyzed by liquid chromatography, the distillation residue was determined to contain 12.3% by weight of toluene-2,4-dicarbamic acid bis(3-methylbutyl) ester and the yield of toluene-2,4-dicarbamic acid bis(3-methylbutyl) ester based on 2,4-toluenediamine was 95%. The composition had a stoichiometric ratio of toluene-2,4-dicarbamic acid bis(3-methylbutyl) ester and 2,6-xylenol of 1:20.3. This composition was a liquid at 120° C., and after maintaining at 120° C. under a nitrogen atmosphere for 2 days, the concentration of toluene-2,4-dicarbamic acid bis(3-methylbutyl) ester was 12.1% by weight.

Example 22

Step (22-1): Production of Toluene-2,4-Dicarbamic Acid Dimethyl Ester

A solution containing 33.1% by weight of toluene-2,4-dicarbamic acid dimethyl ester was obtained by carrying out the same method as step (21-2) of Example 21 with the exception of using 1422 g (15.8 mol) of dimethyl carbonate instead of bis(3-methylbutyl) carbonate, using 305 g (2.5 mol) of 2,4-toluenediamine, and using 33.8 g of sodium methoxide (25% methanol solution).

Step (22-2): Production of Composition 1179 g of a distillate were obtained by carrying out the same method as step (21-3) of Example 21 with the exception of using the solution obtained in step (22-1) and using 5554 g of 2,4-bis(α,α-dimethylbenzyl) phenol instead of 2,6-xylenol. As a result of analyzing by gas chromatography, the distillate was found to be a solution containing 81.2% by weight of dimethyl carbonate and 13.0% by weight of methanol. In addition, as a result of analyzing by liquid chromatography, the distillation residue obtained in the flask was found to contain 9.4% by weight of toluene-2,4-dicarbamic acid dimethyl ester, and the yield of toluene-2,4-dicarbamic acid dimethyl ester based on 2,4-toluenediamine was 96%. This solution was a composition in which the stoichiometric ratio of toluene-2,4-dicarbamic acid dimethyl ester and 2,4-bis(α,α-dimethylbenzyl) phenol was 1:6.9. This composition was a liquid at 130° C., and after maintaining at 130° C. under a nitrogen atmosphere for 1 day, the concentration of toluene-2,4-dicarbamic acid dimethyl ester was 12.8% by weight.

Example 23

Step (23-1): Production of Bis(3-methylbutyl) Carbonate

Bis(3-methylbutyl) carbonate was produced using the same method as step (1-1) of Example 1.

Step (23-2): Production of N,N'-(4,4'-methanediyl-diphenyl)-biscarbamic Acid Bis(3-methylbutyl) Ester 2634 g (13.0 mol) of bis(3-methylbutyl) carbonate obtained in step (23-1) and 416.3 g (2.1 mol) of 4,4'-methylenedianiline (Aldrich Corp., USA) were placed in a 5 L volumetric fourth-mouth flask, a stirrer was placed in the flask, and a Dimroth condenser and three-way valve were attached to the flask. After replacing the inside of the system with nitrogen, the flask was immersed in an oil bath heated to 80° C. followed by the addition of 16.2 g of sodium methoxide (25% methanol solution) with a syringe to start the reaction. Samples of the reaction liquid were suitably collected and subjected to NMR analysis, and the reaction was terminated at the point 4,4'-methylenedianiline was no longer detected.

The resulting solution was housed in a basic sulfonic acid ion exchange resin (Amberlyst-15, spherical, Rohm and Haas Co., USA) adjusted by removing the moisture and supplied to a column warmed to 65° C. by an external jacket to neutralize the sodium methoxide in the solution.

As a result of analyzing the solution by liquid chromatography, the solution was found to contain 28.6% by weight of N,N'-(4,4'-methanediyl-diphenyl)-biscarbamic acid bis(3-methylbutyl) ester.

Step (23-3): Preparation of Composition

The solution obtained in step (23-2) and 2339 g of 2,4-di-tert-amylphenol were mixed to obtain a homogeneous solution. The solution was supplied to a molecular distillation apparatus (MS-300, Sibata Scientific Technology, Ltd., Japan) at the rate of 300 g/Hr and low boiling point components were removed at a temperature of about 130° C. and pressure of about 0.13 kPa to obtain 2341 g of a distillate. As a result of analyzing by gas chromatography, the distillate was determined to be a solution containing 74.5% by weight of bis(3-methylbutyl) carbonate and 14.9% by weight of 3-methyl-1-butanol. In addition, when the distillation residue obtained in the flask was analyzed by liquid chromatography, the distillation residue was determined to contain 28.6% by weight of N,N'-(4,4'-methanediyl-diphenyl)-biscarbamic acid bis(3-methylbutyl) ester, and the yield of N,N'-(4,4'-methanediyl-diphenyl)-biscarbamic acid bis(3-methylbutyl) ester based on 4,4'-methylenedianiline was 95%. The composition had a stoichiometric ratio of N,N'-(4,4'-methanediyl-diphenyl)-biscarbamic acid bis(3-methylbutyl) ester and 2,4-di-tert-amylphenol of 1:4.5. This composition was a liquid at 30° C., and after maintaining at 30° C. under a nitrogen atmosphere for 10 days, the concentration of N,N'-(4,4'-methanediyl-diphenyl)-biscarbamic acid bis(3-methylbutyl) ester was 28.3% by weight.

Example 24

Step (24-1): Production of Dibutyl Carbonate

Dibutyl carbonate was produced using the same method as step (7-1) of Example 7.

Step (24-2): Production of N,N'-(4,4'-methanediyl-diphenyl)-biscarbamic Acid Dibutyl Ester A solution containing 36.9% by weight N,N'-(4,4'-methanediyl-diphenyl)-biscarbamic acid dibutyl ester was obtained by carrying out the same method as step (23-2) of Example 23 with the exception of using 1622 g (9.3 mol) of dibutyl carbonate instead of bis(3-methylbutyl) carbonate, using 377 g (1.9 mol) of 4,4'-methylenedianiline, and using 11.0 g of sodium methoxide (25% methanol solution).

Step (24-3): Production of Composition 1430 g of a distillate were obtained by carrying out the same method as step (23-3) of Example 23 with the exception of using the solution obtained in step (24-2) and using 1988 g of 2,4,6-trimethylphenol instead of 2,4-di-tert-amylphenol. As a result of analyzing by gas chromatography, the distillate was found to be a solution containing 66.5% by weight of dibutyl carbonate and 18.8% by weight of 1-butanol. In addition, as a result of analyzing by liquid chromatography, the distillation residue obtained in the flask was found to contain 28.8% by weight of N,N'-(4,4'-methanediyl-diphenyl)-biscarbamic acid dibutyl ester, and the yield of N,N'-(4,4'-methanediyl-diphenyl)-biscarbamic acid dibutyl ester based on 4,4'-methylenedianiline was 96%.

This solution was a composition in which the stoichiometric ratio of N,N'-(4,4'-methanediyl-diphenyl)-biscarbamic acid dibutyl ester and 2,4,6-trimethylphenol was 1:7.2. This composition was a liquid at 120° C., and after maintaining at 120° C. under a nitrogen atmosphere for 3 days, the concentration of N,N'-(4,4'-methanediyl-diphenyl)-biscarbamic acid dibutyl ester was 28.2% by weight.

Example 25

Production of Hexamethylene Diisocyanate from N,N'-hexanediyl-bis-carbamic Acid Bis(3-methylbutyl) Ester/2,4-di-tert-amylphenol Composition 58.7 g of dibutyl tin dilaurate (Wako Pure Chemical Industries, Ltd., Japan) were added to the composition obtained in step (1-3) of Example 1 to obtain a homogeneous solution.

A thermal decomposition reaction was carried out in a reaction apparatus as shown in FIG. 2 using this solution.

A thin film distillation apparatus 202 (Kobelco Eco-Solutions Co., Ltd., Japan) having a heat-conducting surface area of 0.2 m$^2$ was heated to 200° C. and the pressure within the thin film distillation apparatus was set to about 1.3 kPa. The above solution was placed in a feed tank 201 and supplied to the thin film distillation apparatus at the rate of about 980 g/hr via a line 21. A liquid component was extracted from a line 23 provided in the bottom of thin film distillation apparatus 202 and returned to feed tank 201 via a line 24. A gaseous component containing hexamethylene diisocyanate, 3-methyl-1-butanol and 2,4-di-tert-amylphenol was extracted from a line 22 provided in the upper portion of thin film distillation apparatus 202. The gaseous component was introduced into a distillation column 203 followed by separation of the 3-methyl-1-butanol, and a portion of a high boiling point component was returned to feed tank 201 through a line 26 provided in the bottom of distillation column 203 via line 24. A gaseous component containing hexamethylene diisocyanate and 2,4-di-tert-amylphenol was extracted from a line 27 provided in distillation column 203, and introduced to a distillation column 204. Hexamethylene diisocyanate was separated in distillation column 204. After reacting for 13 hours, 294 g of a solution were recovered from line 32. As a result of analyzing the solution by $^1$H- and $^{13}$C-NMR analysis, the solution was found to contain 99% by weight of hexamethylene diisocyanate. The yield based on hexamethylene diamine was 91.9%. In addition, there were no substances observed to be adhered to the inside of the thin film evaporation apparatus.

Example 26

Production of Hexamethylene Diisocyanate from N,N'-hexanediyl-bis-carbamic Acid Bis(3-methylbuty) Ester/2-phenylphenol Composition 301 g of a solution were recovered from line 32 by carrying out the same method as Example 25 with the exception of using the composition obtained in step (2-3) of Example 2 instead of the composition obtained in step (1-3) of Example 1, and using 64.2 g of dibutyl tin dilaurate (laboratory grade). As a result of analyzing the solution by $^1$H- and $^{13}$C-NMR analysis, the solution was found to contain 99% by weight of hexamethylene diisocyanate. The yield based on hexamethylene diamine was 85.2%. In addition, there were no substances observed to be adhered to the inside of the thin film evaporation apparatus.

Example 27

Production of Hexamethylene Diisocyanate from N,N'-hexanediyl-bis-carbamic Acid Bis(3-methylbuty) Ester/2,4-bis(α,α-dimethylbenzyl) Phenol Composition 378 g of a solution were recovered from line 32 by carrying out the same method as Example 25 with the exception of using the composition obtained in step (3-3) of Example 3 instead of the composition obtained in step (1-3) of Example 1, and using 76.4 g of dibutyl tin dilaurate (laboratory grade). As a result of analyzing the solution by $^1$H- and $^{13}$C-NMR analysis, the solution was found to contain 99% by weight of hexamethylene diisocyanate. The yield based on hexamethylene diamine was 90.0%. In addition, there were no substances observed to be adhered to the inside of the thin film evaporation apparatus.

Example 28

Production of Hexamethylene Diisocyanate from N,N'-hexanediyl-bis-carbamic Acid Bis(3-methylbuty) Ester/2,6-xylenol Composition Step (28-1): Production of N,N'-hexanediyl-bis-carbamic Acid Di(2,6-dimethylphenyl) Ester by Transesterification A transesterification reaction was carried out in a reaction apparatus as shown in FIG. 3.

83.9 g of dibutyl tin dilaurate were added to the composition obtained in step (4-3) of Example 4 to obtain a homogeneous solution. The solution was introduced into a feed tank 401. A thin film distillation apparatus 402 (Kobelco Eco-Solutions Co., Ltd., Japan) having a heat-conducting surface area of 0.2 m$^2$ was heated to 240° C. and the inside of the thin film distillation apparatus was replaced with nitrogen at atmospheric pressure. The solution was supplied to the thin film distillation apparatus at the rate of about 1200 g/hr via a line 41. A mixed gas containing 3-methyl-1-butanol and 2,6-xylenol was extracted from a line 45 provided in the upper portion of the thin film distillation apparatus 402 and supplied to a distillation column 403 packed with Metal Gauze CY Packing (Sulzer Chemtech Ltd., Switzerland). 3-methyl-1-butanol and 2,6-xylenol were separated in distillation column 403, and the 2,6-xylenol was returned to the upper portion of thin film distillation apparatus 402 from a line 46 provided in the bottom of distillation column 403. A reaction liquid was extracted from a line 42 provided in the bottom of the thin film distillation apparatus 402 and returned to feed tank 401 via a line 43.

After carrying out this step for 62 hours, a reaction liquid was extracted from a line 44. 6926 g of reaction liquid were extracted and 166 g of a solution were recovered from a line 47 provided in the upper portion of a distillation column 203.

When the extracted reaction liquid was analyzed by liquid chromatography, the reaction liquid was found to contain 15.2% by weight of N,N'-hexanediyl-bis-carbamic acid bis (2,6-dimethylphenyl) ester. In addition, when the solution recovered from line 47 was analyzed by $^1$H- and $^{13}$C-NMR analysis, the solution was found to contain 98% by weight of methanol.

Step (28-2): Production of Hexamethylene Diisocyanate by Thermal Decomposition of N,N'-hexanediyl-bis-carbamic Acid Di(2,6-dimethylphenyl) Ester A thermal decomposition reaction was carried out in a reaction apparatus as shown in FIG. 2.

A thin film distillation apparatus 202 (Kobelco Eco-Solutions Co., Ltd., Japan) having a heat-conducting surface area of 0.2 m$^2$ was heated to 200° C. and the pressure within the thin film distillation apparatus was set to about 1.3 kPa. The solution obtained in step (28-1) was introduced into a feed tank 201 and supplied to the thin film distillation apparatus at the rate of about 680 g/hr via line 21. A liquid component was extracted from line 23 provided in the bottom of thin film distillation apparatus 202 and returned to feed tank 201 via line 24. A gaseous component containing hexamethylene diisocyanate and 2,6-dimethylphenol was extracted from line 22 provided in the upper portion of thin film distillation apparatus 202. The gaseous component was introduced into distillation column 203 followed by separation of the hexamethylene diisocyanate and 2,6-dimethylphenol, the 2,6-dimethylphenol was extracted from a line 25 after passing through the top of distillation column 203, and a gaseous component containing hexamethylene diisocyanate was extracted from a line 27 provided in distillation column 203. On the other hand, a high boiling point component was extracted from line 26 provided in the bottom of the distillation column, and a portion thereof was returned to feed tank 201 via line 24. The gaseous component containing hexamethylene diisocyanate extracted from line 27 was transferred to distillation column 204, and the hexamethylene diisocyanate was separated by distillation in distillation column 204. A high boiling point component was extracted from line 31 provided in distillation column 204, and a portion thereof was returned to feed tank 201 via line 24. On the other hand, a gaseous component was extracted from line 30, and hexamethylene diisocyanate was extracted from line 32 after passing through a condenser. After reacting for 11 hours, 416 g of a solution containing 99% by weight of hexamethylene diisocyanate were recovered from line 32. The yield based on hexamethylene diamine was 88.4%.

Example 29

Production of Hexamethylene Diisocyanate Using N,N'-hexanediyl-bis-carbamic Acid Dimethyl Ester/2,4,6-trimethylphenol Composition 84.9 g of dibutyl tin dilaurate were added to the composition obtained in step (5-2) to obtain a homogeneous solution.

A thermal decomposition reaction was carried out in a reaction apparatus as shown in FIG. 4 using this solution.

A thin film distillation apparatus 502 (Kobelco Eco-Solutions Co., Ltd., Japan) having a heat-conducting surface area of 0.2 m$^2$ was heated to 200° C. and the pressure within the thin film distillation apparatus was set to about 1.3 kPa. The above solution was placed in a feed tank 501 and supplied to the thin film distillation apparatus at the rate of about 980 g/hr via a line 51. A liquid component was extracted from a line 53 provided in the bottom of thin film distillation apparatus 502 and returned to feed tank 501 via a line 54. A gaseous component containing hexamethylene diisocyanate, methanol and 2,4,6-trimethylphenol was extracted from a line 52 provided in the upper portion of thin film distillation apparatus 502. The gaseous component was introduced into a distillation column 503 followed by separation of the methanol, and a portion of a high boiling point component was returned to feed tank 501 through a line 56 provided in the bottom of distillation column 503 via line 54. A gaseous component containing hexamethylene diisocyanate and 2,4,6-trimethylphenol was extracted from a line 57 provided in distillation column 503, and introduced to a distillation column 504. 2,4,6-trimethylphenol was separated in distillation column 504 and recovered from a line 62. A gaseous component containing hexamethylene diisocyanate was extracted from a line 64 provided in distillation column 504 and introduced into a distillation column 505. The hexamethylene diisocyanate was separated by distillation in distillation column 505 and recovered from a line 67. After reacting for 13 hours, 430 g of a solution were recovered from line 67. As a result of analyzing the solution by $^1$H- and $^{13}$C-NMR analysis, the solution was found to contain 99% by weight of hexamethylene diisocyanate. The yield based on hexamethylene diamine was 91.2%. In addition, there were no substances observed to be adhered to the inside of the thin film evaporation apparatus.

Example 30

Production of Hexamethylene Diisocyanate Using N,N'-hexanediyl-bis-carbamic Acid Dimethyl Ester/2-ethoxyphenol Composition 330 g of a solution were recovered from line 67 by carrying out the same method as Example 29 with the exception of using the composition obtained in step (6-2) instead of the composition obtained in step (5-2), and using 66.7 g of dibutyl tin dilaurate. As a result of analyzing the solution by $^1$H- and $^{13}$C-NMR analysis, the solution was found to contain 99% by weight of hexamethylene diisocyanate. The yield based on hexamethylene diamine was 89.3%. In addition, there were no substances observed to be adhered to the inside of the thin film evaporation apparatus.

Example 31

Production of Hexamethylene Diisocyanate from N,N'-hexanediyl-bis-carbamic Acid Dibutyl Ester/2,6-dimethoxyphenol Composition Step (31-1): Production of N,N'-hexanediyl-bis-carbamic Acid Bis(2,6-dimethoxyphenyl) Ester by Transesterification A transesterification reaction was carried out in a reaction apparatus as shown in FIG. 3.

4088 g of a reaction liquid were recovered from line 44 by carrying out the same method as step (28-1) of Example 28 with the exception of using the composition obtained in step (7-3) of Example 7 instead of the composition obtained in step (4-3) of Example 4, and using 54.0 g of dibutyl tin dilaurate. As a result of analyzing the reaction liquid by liquid chromatography, the reaction liquid was found to contain 19.1% by weight of N,N'-hexanediyl-bis-carbamic acid bis(2,6-dimethoxyphenol) ester. In addition, as a result of analyzing the solution recovered from line 47 by $^1$H- and $^{13}$C-NMR analysis, the solution was found to contain 96% by weight of butanol.

Step (31-2): Production of Hexamethylene Diisocyanate by Thermal Decomposition of N,N'-hexanediyl-bis-carbamic Acid Bis(2,6-dimethoxyphenyl) Ester 267 g of a solution containing 99% by weight of hexamethylene diisocyanate were recovered from line 32 by carrying out the same method as step (28-2) of Example 28 with the exception of using the solution obtained in step (31-1) instead of the solution obtained in step (28-1). The yield based on hexamethylene diamine was 88.4%.

Example 32

Production of Hexamethylene Diisocyanate from N,N'-hexanediyl-bis-carbamic Acid Dibutyl Ester/4-nonylphenol Composition 257 g of a solution were recovered from line 32 by carrying out the same method as Example 25 with the exception of using the composition obtained in step (8-3) of Example 8 instead of the composition obtained in step (1-3) of Example 1, and using 56.8 g of dibutyl tin dilaurate (laboratory grade). As a result of analyzing the solution by $^1$H- and $^{13}$C-NMR analysis, the solution was found to contain 99% by weight of hexamethylene diisocyanate. The yield based on hexamethylene diamine was 80.4%. In addition, there were no substances observed to be adhered to the inside of the thin film evaporation apparatus.

Example 33

Production of Isophorone Diisocyanate from 3-((3-methylbutyl)oxycarbonyl-amino-methyl)-3,5,5-trimethylcyclohexylcarbamic Acid (3-methylbutyl) Ester/2,4-di-tert-amylphenol Composition 390 g of a solution were recovered from line 32 by carrying out the same method as Example 25 with the exception of using the composition obtained in step (9-3) of Example 9 instead of the composition obtained in step (1-3) of Example 1, and using 62.7 g of dibutyl tin dilaurate (laboratory grade). As a result of analyzing the solution by $^1$H- and $^{13}$C-NMR analysis, the solution was found to contain 99% by weight of isophorone diisocyanate. The yield based on 3-aminomethyl-3,5,5-trimethylcyclohexylamine was 85.1%. In addition, there were no substances observed to be adhered to the inside of the thin film evaporation apparatus.

Example 34

Production of Isophorone Diisocyanate from 3-((3-methylbutyl)oxycarbonyl-amino-methyl)-3,5,5-trimethylcyclohexylcarbamic Acid (3-methylbutyl) Ester/2,4-bis(α,α-dimethylbenzyl) Phenol Composition 392 g of a solution were recovered from line 32 by carrying out the same method as Example 25 with the exception of using the composition obtained in step (10-3) of Example 10 instead of the composition obtained in step (1-3) of Example 1, and using 62.6 g of dibutyl tin dilaurate (laboratory grade). As a result of analyzing the solution by $^1$H- and $^{13}$C-NMR analysis, the solution was found to contain 99% by weight of isophorone diisocyanate. The yield based on 3-aminomethyl-3,5,5-trimethylcyclohexylamine was 84.0%. In addition, there were no substances observed to be adhered to the inside of the thin film evaporation apparatus.

Example 35

Production of Isophorone Diisocyanate from 3-(methyloxycarbonylamino-methyl)-3,5,5-trimethylcyclohexylcarbamic Acid Methyl Ester/2,6-Dimethylphenol Composition 588 g of a solution were recovered from line 67 by carrying out the same method as Example 29 with the exception of using the composition obtained in step (11-2) instead of the composition obtained in step (5-2), and using 96.1 g of dibutyl tin dilaurate. As a result of analyzing the solution by $^1$H- and $^{13}$C-NMR analysis, the solution was found to contain 99% by weight of isophorone diisocyanate. The yield based on 3-aminomethyl-3,5,5-trimethylcyclohexylamine was 82.7%. In addition, there were no substances observed to be adhered to the inside of the thin film evaporation apparatus.

Example 36

Production of Isophorone Diisocyanate from 3-(methyloxycarbonylamino-methyl)-3,5,5-trimethylcyclohexylcarbamic Acid Methyl Ester/2,4,6-trimethylphenol Composition Step (36-1): Production of 3-((2,4,6-trimethylphenyl)oxycarbonylamino-methyl)-3,5,5-trimethylcyclohexylcarbamic Acid (2,4,6-trimethylphenyl) Ester by Transesterification A transesterification reaction was carried out in a reaction apparatus as shown in FIG. 3.

12410 g of a reaction liquid were recovered from line 44 by carrying out the same method as step (28-1) of Example 28 with the exception of using the composition obtained in step (12-2) of Example 12 instead of the composition obtained in step (4-3) of Example 4, and using 83.2 g of dibutyl tin dilaurate. As a result of analyzing the reaction liquid by liquid chromatography, the reaction liquid was found to contain 10.1% by weight of 3-((2,4,6-trimethylphenyl)oxycarbonylamino-methyl)-3,5,5-trimethylcyclohexylcarbamic acid (2,4,6-trimethylphenyl) ester. In addition, as a result of analyzing the solution recovered from line 47 by $^1$H- and $^{13}$C-NMR analysis, the solution was found to contain 98% by weight of methanol.

Step (36-2): Production of Isophorone Diisocyanate by Thermal Decomposition of 3-((2,4,6-trimethylphenyl)oxycarbonylamino-methyl)-3,5,5-trimethylcyclohexylcarbamic Acid (2,4,6-trimethylphenyl) Ester 544 g of a solution containing 99% by weight of isophorone diisocyanate were recovered from line 32 by carrying out the same method as step (28-2) of Example 28 with the exception of using the solution obtained in step (36-1)

instead of the solution obtained in step (28-1). The yield based on 3-amino-methyl-3,5,5-trimethylcyclohexylamine was 87.5%.

Example 37

Production of Isophorone Diisocyanate from 3-(butyloxycarbonylamino-methyl)-3,5,5-trimethylcyclohexylcarbamic Acid Butyl Ester/4-nonylphenol Composition Step (37-1): Production of 3-((4-nonylphenyl)oxycarbonylamino-methyl)-3,5,5-trimethylcyclohexylcarbamic Acid (4-nonylphenyl) Ester by Transesterification A transesterification reaction was carried out in a reaction apparatus as shown in FIG. 3.

83.2 g of dibutyl tin dilaurate were added to the composition obtained in step (13-3) of Example 13 to obtain a homogeneous solution. The solution was placed in feed tank 401. Thin film distillation apparatus 402 (Kobelco Eco-Solutions Co., Ltd., Japan) having a heat-conducting surface area of 0.2 m$^2$ was heated to 240° C. and the inside of the thin film distillation apparatus was replaced with nitrogen at atmospheric pressure. The solution was supplied to the thin film distillation apparatus at the rate of about 1200 g/hr via feed line 41. A mixed gas containing 1-butanol and 4-nonylphenol was extracted from line 45 provided in the upper portion of the thin film distillation apparatus 402 and supplied to distillation column 403 packed with Metal Gauze CY Packing (Sulzer Chemtech Ltd., Switzerland). 1-Butanol and 4-nonylphenol were separated in distillation column 403, and the 4-nonylphenol was returned to the upper portion of thin film distillation apparatus 402 from line 46 provided in the bottom of distillation column 403. A reaction liquid was extracted from line 42 provided in the bottom of the thin film distillation apparatus 402 and returned to feed tank 401 via line 43.

After carrying out this step for 62 hours, a reaction liquid was extracted from line 44. 6419 g of reaction liquid were extracted and 575 g of a solution were recovered from line 47 provided in the upper portion of a distillation column 403.

When the extracted reaction liquid was analyzed by liquid chromatography, the reaction liquid was found to contain 24.5% by weight of 3-((4-nonylphenyl)oxycarbonylamino-methyl)-3,5,5-trimethylcyclohexylcarbamic acid (4-nonylphenyl) ester. In addition, when the solution recovered from line 47 was analyzed by $^1$H- and $^{13}$C-NMR analysis, the solution was found to contain 98% by weight of 1-butanol.

Step (37-2): Production of Isophorone Diisocyanate by Thermal Decomposition of 3-((4-nonylphenyl)oxycarbonylamino-methyl)-3,5,5-trimethylcyclohexylcarbamic Acid (4-nonylphenyl) Ester A thermal decomposition reaction was carried out in a reaction apparatus as shown in FIG. 5.

A thin film distillation apparatus 702 (Kobelco Eco-Solutions Co., Ltd., Japan) having a heat-conducting surface area of 0.2 m$^2$ was heated to 200° C. and the pressure within the thin film distillation apparatus was set to about 1.3 kPa. The solution obtained in step (37-2) was placed in a feed tank 701 and supplied to the thin film distillation apparatus at the rate of about 980 g/hr via a line 71. A liquid component was extracted from a line 73 provided in the bottom of thin film distillation apparatus 702 and returned to feed tank 701 via a line 74. A gaseous component containing isophorone diisocyanate and 4-nonylphenol was extracted from a line 72 provided in the upper portion of thin film distillation apparatus 702. The gaseous component was introduced into a distillation column 703, the isophorone diisocyanate and 4-nonylphenol were separated, and a portion of the 4-nonylphenol was returned to feed tank 701 through line 74 via a line 76 provided in the bottom of distillation column 703. After reacting for 13 hours, 484 g of a solution were recovered from a line 75. As a result of analyzing by $^1$H- and $^{13}$C-NMR analysis, the solution was found to contain 99% by weight of isophorone diisocyanate. The yield based on 3-aminomethyl-3,5,5-trimethylcyclohexylamine was 77.8%.

Example 38

Production of Isophorone Diisocyanate from 3-(butyloxycarbonylamino-methyl)-3,5,5-trimethylcyclohexylcarbamic Acid Butyl Ester/2,6-dimethoxyphenol Composition Step (38-1): Production of 3-((2,6-dimethoxyphenyl)oxycarbonylamino-methyl)-3,5,5-trimethylcyclohexylcarbamic Acid (2,6-dimethoxyphenyl) Ester by Transesterification A transesterification reaction was carried out in a reaction apparatus as shown in FIG. 3.

10121 g of a reaction liquid were recovered from line 44 by carrying out the same method as step (28-1) of Example 28 with the exception of using the composition obtained in step (14-3) of Example 14 instead of the composition obtained in step (4-3) of Example 4, and using 92.1 g of dibutyl tin dilaurate. As a result of analyzing the reaction liquid by liquid chromatography, the reaction liquid was found to contain 14.7% by weight of 3-((2,6-dimethoxyphenyl)oxycarbonylamino-methyl)-3,5,5-trimethylcyclohexylcarbamic acid (2,6-dimethoxyphenyl) ester produced by the transesterification reaction. In addition, as a result of analyzing the solution recovered from line 47 by $^1$H- and $^{13}$C-NMR analysis, the solution was found to contain 98% by weight of 1-butanol.

Step (38-2): Production of Isophorone Diisocyanate by Thermal Decomposition of 3-((2,6-dimethoxyphenyl)oxycarbonylamino-methyl)-3,5,5-trimethylcyclohexylcarbamic Acid (2,6-dimethoxyphenyl) Ester 579 g of a solution containing 99% by weight of isophorone diisocyanate were recovered from line 32 by carrying out the same method as step (28-2) of Example 28 with the exception of using the solution obtained in step (38-1) instead of the solution obtained in step (28-1). The yield based on 3-aminomethyl-3,5,5-trimethylcyclohexylamine was 84.0%.

Example 39

Production of 4,4'-methylenebis(cyclohexylisocyanate) Using Dibutyl-4,4'-methylene-dicyclohexyl Carbamate/2-tert-amylphenol Composition 481 g of a solution were recovered from line 67 by carrying out the same method as Example 29 with the exception of using the composition obtained in step (15-3) instead of the composition obtained in step (5-2), and using 64.4 g of dibutyl tin dilaurate. As a result of analyzing the solution by $^1$H- and $^{13}$C-NMR analysis, the solution was found to contain 99% by weight of 4,4'-methylenebis(cyclohexyldiisocyanate). The yield based on 4,4'-methylenebis(cyclohexylamine) was 87.3%. In addition, there were no substances observed to be adhered to the inside of the thin film evaporation apparatus following the reaction.

Example 40

Production of 4,4'-methylenebis(cyclohexylisocyanate) Using Bis(3-methylbutyl)-4,4'-methylene-dicyclohexyl Carbamate/2,4-di-tert-amylphenol Composition 498 g of a solution were recovered from line 67 by carrying out the same method as Example 29 with the exception of using the composition obtained in step (16-3) instead of the composition obtained in step (5-2), and using 66.7 g of dibutyl tin dilaurate. As a result of analyzing the solution by $^1$H- and $^{13}$C-NMR analysis, the solution was found to contain 99% by weight of 4,4'-methylenebis(cyclohexyldiisocyanate). The yield based on 4,4'-methylenebis(cyclohexylamine) was 86.4%. In addition, there were no substances observed to be adhered to the inside of the thin film evaporation apparatus following the reaction.

Example 41

Production of 4,4'-methylenebis(cyclohexylisocyanate) Using Dimethyl-4,4'-methylene-dicyclohexyl Carbamate/2,6-diisopropylphenol Composition 577 g of a solution were recovered from line 67 by carrying out the same method as Example 29 with the exception of using the composition obtained in step (17-2) instead of the composition obtained in step (5-2), and using 78.1 g of dibutyl tin dilaurate. As a result of analyzing the solution by $^1$H- and $^{13}$C-NMR analysis, the solution was found to contain 99% by weight of 4,4'-methylenebis(cyclohexyldiisocyanate). The yield based on 4,4'-methylenebis(cyclohexylamine) was 84.6%. In addition, there were no substances observed to be adhered to the inside of the thin film evaporation apparatus following the reaction.

Example 42

Production of 4,4'-methylenebis(cyclohexylisocyanate) from Dimethyl-4,4'-methylene-dicyclohexyl Carbamate/2,6-dimethylphenol Composition Step (42-1): Production of Bis(2,6-dimethylphenyl)-4,4'-methylenedicyclohexyl Carbamate by Transesterification A transesterification reaction was carried out in a reaction apparatus as shown in FIG. 3.
5832 g of a reaction liquid were recovered from line 44 by carrying out the same method as step (28-1) of Example 28 with the exception of using the composition obtained in step (18-2) of Example 18 instead of the composition obtained in step (4-3) of Example 4, and using 78.1 g of dibutyl tin dilaurate. As a result of analyzing the reaction liquid by liquid chromatography, the reaction liquid was found to contain 25.2% by weight of bis(2,6-dimethylphenyl)-4,4'-methylene-dicyclohexyl carbamate. In addition, as a result of analyzing the solution recovered from line 47 by $^1$H- and $^{13}$C-NMR analysis, the solution was found to contain 96% by weight of methanol.

Step (42-2): Production of Hexamethylene Diisocyanate by Thermal Decomposition of Bis(2,6-dimethylphenyl)-4,4'-methylene-dicyclohexyl Carbamate 603 g of a solution containing 99% by weight of 4,4'-methylenebis (cyclohexyldiisocyanate) were recovered from line 32 by carrying out the same method as step (28-2) of Example 28 with the exception of using the solution obtained in step (42-1) instead of the solution obtained in step (28-1). The yield based on 4,4'-methylenebis(cyclohexylamine) was 88.5%.

Example 43

Production of 4,4'-methylenebis(cyclohexylisocyanate) from Bis(3-methylbutyl)-4,4'-methylene-dicyclohexyl Carbamate/2-phenylphenol Composition Step (43-1): Production of Bis(2-phenylphenyl)-4,4'-methylenedicyclohexyl Carbamate by Transesterification A transesterification reaction was carried out in a reaction apparatus as shown in FIG. 3.
6091 g of a reaction liquid were recovered from line 44 by carrying out the same method as step (28-1) of Example 28 with the exception of using the composition obtained in step (19-3) of Example 19 instead of the composition obtained in step (4-3) of Example 4, and using 72.8 g of dibutyl tin dilaurate. As a result of analyzing the reaction liquid by liquid chromatography, the reaction liquid was found to contain 25.2% by weight of bis(2-phenylphenyl)-4,4'-methylene-dicyclohexyl carbamate. In addition, as a result of analyzing the solution recovered from line 47 by $^1$H- and $^{13}$C-NMR analysis, the solution was found to contain 96% by weight of 3-methyl-1-butanol.

Step (43-2): Production of Hexamethylene Diisocyanate by Thermal Decomposition of Bis(2-phenylphenyl)-4,4'-methylene-dicyclohexyl Carbamate 517 g of a solution containing 99% by weight of 4,4'-methylenebis (cyclohexyldiisocyanate) were recovered from line 32 by carrying out the same method as step (28-2) of Example 28 with the exception of using the solution obtained in step (43-1) instead of the solution obtained in step (28-1). The yield based on 4,4'-methylenebis(cyclohexylamine) was 82.0%.

Example 44

Production of 4,4'-methylenebis(cyclohexylisocyanate) Using Dibutyl-4,4'-methylene-dicyclohexyl Carbamate/4-tert-butylphenol Composition 630 g of a solution were recovered from line 67 by carrying out the same method as Example 29 with the exception of using the composition obtained in step (20-3)

instead of the composition obtained in step (5-2), and using 92.6 g of dibutyl tin dilaurate. As a result of analyzing the solution by $^1$H- and $^{13}$C-NMR analysis, the solution was found to contain 99% by weight of 4,4'-methylenebis(cyclohexyldiisocyanate). The yield based on 4,4'-methylenebis (cyclohexylamine) was 77.5%. In addition, there were no substances observed to be adhered to the inside of the thin film evaporation apparatus following the reaction.

Example 45

Production of 2,4-Toluenediisocyanate Using Toluene-2,4-Dicarbamic Acid Bis(3-methylbutyl) Ester/2,6-dimethylphenol Composition 325 g of a solution were recovered from line 67 by carrying out the same method as Example 29 with the exception of using the composition obtained in step (21-3) instead of the composition obtained in step (5-2), and using 63.6 g of dibutyl tin dilaurate. As a result of analyzing the solution by $^1$H- and $^{13}$C-NMR analysis, the solution was found to contain 99% by weight of 2,4-toluenediisocyanate. The yield based on 2,4-toluenediamine was 89.1%. In addition, there were no substances observed to be adhered to the inside of the thin film evaporation apparatus following the reaction.

Example 46

Production of 2,4-Toluenediisocyanate Using Toluene-2,4-Dicarbamic Acid Dimethyl Ester/2,4-bis(α,α-dimethylbenzyl) Phenol Composition Step (46-1): Production of Toluene-2,4-Dicarbamic Acid Bis(2,4-bis(α,α-dimethylbenzyl)phenyl) Ester by Transesterification A transesterification reaction was carried out in a reaction apparatus as shown in FIG. 3.

5433 g of a reaction liquid were recovered from line 44 by carrying out the same method as step (37-1) of Example 37 with the exception of using the composition obtained in step (22-2) of Example 22 instead of the composition obtained in step (13-3) of Example 13, and using 46.3 g of dibutyl tin dilaurate.

As a result of analyzing the extracted reaction liquid by liquid chromatography, the reaction liquid was found to contain 14.9% by weight of toluene-2,4-dicarbamic acid bis(2,4-bis(α,α-dimethylbenzyl)phenyl) ester. In addition, as a result of analyzing the solution recovered from line 47 by $^1$H- and $^{13}$C-NMR analysis, the solution was found to contain 98% by weight of methanol.

Step (46-2): Production of 2,4-Toluenediisocyanate by Thermal Decomposition Toluene-2,4-Dicarbamic Acid Bis(2,4-bis(α,α-dimethylbenzyl)phenyl) Ester 319 g of a solution were recovered from line 75 by carrying out the same method as step (37-2) of Example 37 with the exception of using the solution obtained in step (38-1) instead of the solution obtained in step (37-1). As a result of analyzing the solution by $^1$H- and $^{13}$C-NMR analysis, the solution was found to contain 99% by weight of 2,4-toluenediisocyanate. The yield based on 2,4-toluenediamine was 87.3%.

Example 47

Production of 4,4'-methylenebis(Phenylisocyanate) Using N,N'-(4,4'-methanediyl-diphenyl)-biscarbamic Acid Bis(3-methylbutyl) Ester/2,4-di-tert-amylphenol Composition 469 g of a solution were recovered from line 67 by carrying out the same method as Example 29 with the exception of using the composition obtained in step (23-3) instead of the composition obtained in step (5-2), and using 63.0 g of dibutyl tin dilaurate. As a result of analyzing the solution by $^1$H- and $^{13}$C-NMR analysis, the solution was found to contain 99% by weight of 4,4'-methylenebis(phenylisocyanate). The yield based on 4,4'-methylenedianiline was 89.3%. In addition, there were no substances observed to be adhered to the inside of the thin film evaporation apparatus following the reaction.

Example 48

Production 4,4'-methylenebis(Phenylisocyanate) Using N,N'-(4,4'-methanediyl-diphenyl)-biscarbamic Acid Dibutyl Ester/2,4,6-trimethylphenol Composition Step (48-1): Production of N,N'-(4,4'-methanediyl-diphenyl)-biscarbamic Acid Bis(2,4,6-trimethylphenyl) Ester by Transesterification A transesterification reaction was carried out in a reaction apparatus as shown in FIG. 3.

2321 g of a reaction liquid were recovered from line 44 by carrying out the same method as step (28-1) of Example 28 with the exception of using the composition obtained in step (24-3) of Example 24 instead of the composition obtained in step (4-3) of Example 4, and using 57.6 g of dibutyl tin dilaurate. As a result of analyzing the extracted reaction liquid by liquid chromatography, the reaction liquid was found to contain 39.0% by weight of N,N'-(4,4'-methanediyl-diphenyl)-biscarbamic acid bis(2,4,6-trimethylphenyl) ester. In addition, as a result of analyzing the solution recovered from line 47 by $^1$H- and $^{13}$C-NMR analysis, the solution was found to contain 98% by weight of 1-butanol.

Step (48-2): Production of 4,4'-methylenebis(Phenylisocyanate) by Thermal Decomposition of N,N'-(4,4'-methanediyl-diphenyl)-biscarbamic Acid Bis (2,4,6-Triphenyl) Ester 420 g of a solution containing 99% by weight of 4,4'-methylenebis (phenylisocyanate) were recovered from line 32 by carrying out the same method as step (28-2) of Example 28 with the exception of using the solution obtained in step (48-1) instead of the solution obtained in step (28-1). The yield based on 4,4'-methylenedianiline was 88.3%. In addition, there were no substances observed to be adhered to the inside of the thin film evaporation apparatus following the reaction.

Example 49

Production of hexamethylene diisocyanate was carried out in a reaction apparatus as shown in FIG. 6

Step (49-1): N,N'-hexanediyl-bis-carbamic Acid Bis (3-methylbutyl) Ester Production Step A stirring tank 801 (internal volume: 30 L) was heated to 80° C. Bis(3-methylbutyl) carbonate, produced using the same method as step (1-1) of Example 1 and preheated to 80° C., was transferred to the stirring tank 801 from a line 80 at the rate of 1820 g/hr with a line 82 closed, and a mixed solution of hexamethylene diamine, 3-methyl-1-butanol and sodium methoxide (28% methanol solution) (mixing ratio: hexamethylene diamine 50 parts/3-methyl-1-butanol 50 parts/sodium methoxide 4.2 parts) was simultaneously transferred from a line 81 at the rate of 209 g/hr. After 5 hours, line 82 was opened with a line 83 closed, and the solution was housed in a basic sulfonic acid ion exchange resin (Amberlyst-15, spherical, Rohm and Haas Co., USA) adjusted by removing the moisture and supplied to an ion exchange resin column 812 maintained at 80° C. by an external jacket to neutralize the sodium methoxide, followed by transferring to a tank 802 through a line 83. Lines 82 and 83 were maintained at 80° C. to prevent precipitation of solids from the reaction liquid.

When the reaction liquid transferred to tank 802 was analyzed by liquid chromatography, the reaction liquid was found to contain 29.7% by weight of N,N'-hexanediyl-bis-carbamic acid bis(3-methylbutyl) ester.

Step (49-2): Low Boiling Point Component Distillation Step

The reaction liquid produced in step (49-1) was transferred from tank 802 to stirring tank 803 maintained at 80° C. through line 84 at the rate of 130 g/hr. 2,4-Di-tert-amylphenol heated to 80° C. was simultaneously added to stirring tank 803 from a line 85 at the rate of 131 g/hr to obtain a homogeneous solution. The solution was transferred to a thin film distillation apparatus 804 (Kobelco Eco-Solutions Co., Ltd., Japan, heat-conducting surface area of 0.2 m$^2$) heated to 150° C. and set to an internal pressure of 0.1 kPa through a line 86 maintained at 80° C. at the rate of 261 g/hr where a low boiling point component contained in the solution were distilled off. The low boiling point component that had been distilled off was extracted from the thin film distillation apparatus 804 from a line 87. On the other hand, a high boiling point component was extracted from the thin film distillation apparatus 804 via a line 88 maintained at 80° C., and transferred to a tank 805 maintained at 80° C. Dibutyl tin dilaurate was added to tank 805 from line 89 at the rate of 16.7 g/hr.

When the solution stored in the tank 805 was analyzed by liquid chromatography, the solution was found to contain 24.1% by weight of N,N'-hexanediyl-bis-carbamic acid bis (3-methylbutyl) ester.

Step (49-3): Hexamethylene Diisocyanate Production Step by Thermal Decomposition of N,N'-hexanediyl-bis-carbamic Acid Bis(3-methylbutyl) Ester The solution stored in tank 805 was supplied to a thin film distillation apparatus 806 (Kobelco Eco-Solutions Co., Ltd., Japan, heat-conducting surface area of 0.1 m$^2$) heated to 200° C. and set to an internal pressure of about 1.3 kPa via line 90 at the rate of 800 g/hr. A gaseous component containing hexamethylene diisocyanate, 3-methyl-1-butanol and 2,4-di-tert-amylphenol was extracted from a line 95 provided in the upper portion of the thin film distillation apparatus 806. The gaseous component was introduced into a distillation column 807 to separate the 3-methyl-1-butanol, and a portion of a high boiling point component was returned to thin film distillation apparatus 806 via a line 94 provided in the bottom of distillation column 807 after passing through a line 93. A gaseous component containing hexamethylene diisocyanate and 2,4-di-tert-amylphenol was extracted from a line 97 provided in distillation column 807 and introduced into a distillation column 810. The hexamethylene diisocyanate was separated in this distillation column 810. After reacting for 12 hours, a solution was recovered from a line 99 at the rate of about 88 g/hr, and as a result of analyzing by $^1$H- and $^{13}$C-NMR analysis, the solution was found to contain 99% by weight of hexamethylene diisocyanate. The yield based on hexamethylene diamine was 92%. In addition, there were no substances observed to be adhered to the inside of the thin film evaporation apparatus following the reaction.

Example 50

Step (50-1): Production of Bis(3-methylbutyl) Carbonate 688 g (3.0 mol) of di-n-butyl tin oxide (Sankyo Organic Chemicals Co., Ltd., Japan) and 2222 g (25.0 mol) of 3-methyl-1-butanol (Kuraray Co., Ltd., Japan) were placed in a 5000 mL volumetric pear-shaped flask. The flask was connected to an evaporator (R-144, Shibata Co., Ltd., Japan) to which was connected an oil bath (OBH-24, Masuda Corp., Japan) equipped with a temperature controller, a vacuum pump (G-50A, ULVAC Inc., Japan) and a vacuum controller (VC-10S, Okano Seisakusho Co., Ltd.). The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to about 145° C., the flask was immersed in the oil bath and rotation of the evaporator was started. After heating for about 40 minutes in the presence of atmospheric pressure nitrogen with the purge valve of the evaporator left open, distillation of 3-methyl-1-butanol containing water began. After maintaining in this state for 7 hours, the purge valve was closed, pressure inside the system was gradually reduced, and excess 3-methyl-1-butanol was distilled with the pressure inside the system at 74 to 35 kPa. After the fraction no longer appeared, the flask was taken out of the oil bath. After allowing the flask to cool to the vicinity of room temperature (25° C.), the flask was taken out of the oil bath, the purge valve was opened gradually and the pressure inside the system was returned to atmospheric pressure. 1290 g of reaction liquid were obtained in the flask. Based on the results of $^{119}$Sn-, $^1$H- and $^{13}$C-NMR analyses, 1,1,3,3-tetra-n-butyl-1,3-bis(3-methylbutyloxy) distannoxane was confirmed to have been obtained at a yield of 99% based on di-n-butyl tin oxide. The same procedure was then repeated 12 times to obtain a total of 11368 g of 1,1,3,3-tetra-n-butyl-1,3-bis(3-methylbutyloxy) distannoxane.

Bis(3-methylbutyl) carbonate was produced in a continuous production apparatus like that shown in FIG. 7. 1,1,3, 3-Tetrabutyl-1,3-bis(3-methylbutyloxy) distannoxane produced in the manner described above was supplied at the rate of 4388 g/hr from a transfer line A4 into a column-type reaction vessel A102 packed with Metal Gauze CY Packing (Sulzer Chemtech Ltd., Switzerland) and having an inner diameter of 151 mm and effective length of 5040 mm. On the other hand, 3-methyl-1-butanol was supplied to a distillation column A101 from a tank A100 by line A1, and the 3-methyl-1-butanol purified in distillation column A101 was supplied at the rate of 14953 g/hr to column-type reaction vessel A102 from a line A2. The liquid temperature inside reaction vessel A102 was controlled to 160° C. by a heater and a reboiler A133, and the pressure was adjusted to about 120 kPa-G with a pressure control valve. The residence time in the reaction vessel was about 17 minutes. 3-methyl-1-butanol containing water at the rate of 15037 g/hr from the top of the reaction vessel via a transfer line A6, and 3-methyl-1-butanol at the rate of 825 g/hr via feed line A1, were pumped to distillation column A101 packed with Metal Gauze CY Packing and provided with a reboiler A132 and a condenser A131 to carry out distillative purification. In the top of distillation column A101, a fraction containing a high concentration of water was condensed by condenser A121 and recovered from a recovery line A3. Purified 3-methyl-1-butanol was pumped to column-type reaction vessel A102 via transfer line A2 located in the lower portion of distillation column A101. An alkyl tin alkoxide catalyst composition containing di-n-butyl-bis(3-methylbutyloxy) tin and 1,1,3,3-tetra-n-butyl-1,3-bis(3-methylbutyloxy) distannoxane was obtained from the lower portion of column-type reaction vessel A102, and supplied to a thin film evaporation apparatus A103 (Kobelco Eco-Solutions Co., Ltd., Japan) via a transfer line A5. The 3-methyl-1-butanol was distilled off in thin film evaporation apparatus A103 and returned to column-type reaction vessel A102 via a condenser A134, a transfer line A8 and transfer line A4. The alkyl tin alkoxide catalyst composition was pumped from the lower portion of thin film evaporation apparatus A103 via a transfer line A7 and supplied to an autoclave A104 while adjusting the flow rate of di-n-butyl-bis(3-methylbutyloxy) tin and 1,1,3,3-tetra-n-butyl-1,3-bis(3-methylbutyloxy) distannoxane to about 5130 g/hr. Carbon dioxide was supplied to the autoclave by a transfer line A9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing bis(3-methylbutyl) carbonate. This reaction liquid was transferred to a decarbonization tank A105 via a transfer line A10 and a control valve to remove residual carbon dioxide, and the carbon dioxide was recovered from a transfer line A11. Subsequently, the reaction liquid was transferred to a thin film evaporation apparatus (Kobelco Eco-Solutions Co., Ltd., Japan) A106 set to about 142° C. and about 0.5 kPa via a transfer line A12 and supplied while adjusting the flow rate of 1,1,3,3-tetra-n-butyl-1,3-bis(3-methylbutyloxy) distannoxane to about 4388 g/hr to obtain a fraction containing bis(3-methylbutyl) carbonate. On the other hand, the evaporation residue was circulated to column-type reaction vessel A102 via transfer line A13 and transfer line A4 while adjusting the flow rate of 1,1,3,3-tetrabutyl-1,3-bis(3-methylbutyloxy) distannoxane to about 4388 g/hr. The fraction containing bis(3-methylbutyl) carbonate was supplied to a distillation column A107 packed with Metal Gauze CY packing and equipped with a reboiler A136 and a condenser A137 via a condenser A135 and a transfer line A14 at the rate of 959 g/hr followed by distillative purification to obtain 99 wt % bis(3-methylbutyl) carbonate from a recovery line A15 at the rate of 944 g/hr. The bis(3-methylbutyl) carbonate was stored in a tank A108. When the alkyl tin alkoxide catalyst composition of a transfer line A13 was analyzed by $^{119}$Sn-, $^{1}$H- and $^{13}$C-NMR analysis, it was found to contain 1,1,3,3-tetra-n-butyl-1,3-bis(3-methylbutyloxy) distannoxane but not contain di-n-butyl-bis(3-methylbutyloxy) tin. After carrying out the above-mentioned continuous operation for about 240 hours, alkyl tin alkoxide catalyst composition was extracted from an extraction line A16 at the rate of 20 g/hr, while 1,1,3,3-tetra-n-butyl-1,3-bis(3-methylbutyloxy) distannoxane produced according to the above process was supplied from a feed line A17 at the rate of 20 g/hr.

Step (50-2): N,N'-hexanediyl-bis-carbamic Acid Bis(3-methylbutyl) Ester Production Step A stirring tank A110 was heated to 80° C. Bis(3-methylbutyl) carbonate was transferred to the stirring tank A110 from a tank A108 by a line A21 at the rate of 1214 g/hr with a line A22 closed, and a mixed solution of hexamethylene diamine, 3-methyl-1-butanol and sodium methoxide (28% methanol solution) (mixing ratio: hexamethylene diamine 50 parts/3-methyl-1-butanol 50 parts/sodium methoxide 0.42 parts) was simultaneously transferred from a line A20 at the rate of 234 g/hr. After 4 hours, line A22 was opened with a line A23 closed, and transfer of the reaction liquid was started to a stirring tank A111 maintained at 80° C. at the rate of 1448 g/hr. Line A22 was maintained at 80° C. to prevent precipitation of solids from the solution. At the same time, 2,4-di-tert-amylphenol was transferred from a tank A109 to stirring tank A111 through a line A25 at the rate of 2225 g/hr to obtain a homogeneous solution in stirring tank A111. The solution was then stored in a stirring tank A112 maintained at a temperature of 80° C. via line A23.

When the mixed liquid transferred to tank A112 was analyzed by liquid chromatography, the mixed liquid was found to contain 9.2% by weight of N,N'-hexanediyl-bis-carbamic acid bis(3-methylbutyl) ester.

Step (50-3): Low Boiling Point Component Distillation Step

A thin film distillation apparatus A113 (Kobelco Eco-Solutions Co., Ltd., Japan, heat-conducting surface area of 0.2 m$^2$) was heated to 150° C. and set to an internal pressure of about 0.1 kPa.

The solution stored in tank A112 was transferred to thin film distillation apparatus A113 by line A24 maintained at 80° C. at the rate of 3673 g/hr where a low boiling point component contained in the solution was distilled off. The low boiling point component which was distilled off was extracted from the thin film distillation apparatus A113 through a line A27. The extracted low boiling point component was introduced into a distillation column A118 to carry out distillative separation, and 3-methyl-1-butanol was recovered from a line A30 and stored in a tank A100. On the other hand, a high boiling point component was extracted from the thin film distillation apparatus A113 by a line A26 maintained at 150° C., and transferred to a stirring tank A114 maintained at 80° C. Dibutyl tin dilaurate was simultaneously transferred to stirring tank A114 from a line A31 at the rate of 29 g/hr to obtain a homogeneous solution.

The mixed liquid prepared in the stirring tank A114 was transferred to a tank A115 by a line A32 with a line A33 closed and stored in tank A115. When the solution stored in tank A115 was analyzed by liquid chromatography, the solution was found to contain 13.4% by weight of N,N'-hexanediyl-bis-carbamic acid bis(3-methylbutyl) ester.

Step (50-4): N,N'-hexanediyl-bis-carbamic Acid Bis(2,4-di-tert-amylphenyl) Ester Production Step by Transesterification A thin film distillation apparatus A116 (Kobelco Eco-Solutions Co., Ltd., Japan, heat-conducting surface area of 0.2 m$^2$) was heated to 240° C.

A transesterification reaction was carried out by transferring a mixed liquid of N,N'-hexanediyl-bis-carbamic acid bis(3-methylbutyl) ester, 2,4-di-tert-amylphenol and dibutyl tin dilaurate stored in tank A115 to thin film distillation apparatus A116 via a line A33 at the rate of 2436 g/hr with a line A36 closed. A mixed gas containing 3-methyl-1-butanol and 2,4-di-tert-amylphenol was extracted from a line A37 provided in the upper portion of the thin film distillation apparatus A116, and supplied to a distillation column A119. The 3-methyl-1-butanol and 2,4-di-tert-amylphenol were separated in the distillation column A119, and the 3-methyl-1-butanol was extracted by line A39 and stored in tank A100 via line A40. On the other hand, the 2,4-di-tert-amylphenol was returned to the upper portion of thin film distillation apparatus A116 via a line A38 provided in the bottom of distillation column A119. A reaction liquid was extracted from a line A34 provided in the bottom of the thin film distillation apparatus A116, and supplied to thin film distillation apparatus A116 via a line A35. When the N,N'-hexanediyl-bis-carbamic acid bis(2,4-di-tert-amylphenyl) ester in the reaction liquid extracted from line A35 reached 25.2% by weight, line A36 was opened with line A41 closed and the reaction liquid was transferred to a tank A121.

Step (50-5): Hexamethylene Diisocyanate Production Step by Thermal Decomposition of N,N'-hexanediyl-bis-carbamic Acid Bis(2,4-di-tert-amylphenyl) Ester The solution stored in tank A121 was supplied to a thin film distillation apparatus A122 (Kobelco Eco-Solutions Co., Ltd., Japan, heat-conducting surface area of 0.1 m²) heated to 200° C. and set to an internal pressure of about 1.3 kPa via line A41 at the rate of 2306 g/hr. A gaseous component containing hexamethylene diisocyanate was extracted from a line A43 provided in the upper portion of the thin film distillation apparatus A122 and supplied to distillation column A123. Distillative separation was carried out in distillation column A123 and hexamethylene diisocyanate was recovered from line A45 at the rate of 447 g/hr.

A high boiling point component separated with distillation column A123 was extracted from line A47 and introduced into a distillation column A126 via a line A48. 2,4-di-tert-amylphenol was separated from the high boiling point component in the distillation column A126 and transferred to tank A109 by line A49.

Although the above series of steps were carried out to recover 643 kg of hexamethylene diisocyanate, there were no substances observed to be adhered to the inside of the thin film distillation apparatus following the reaction.

Comparative Example 1

Step (A-1): Production of Bis(3-methylbutyl) Carbonate

Bis(3-methylbutyl) carbonate was produced using the same method as step (1-1) of Example 1.

Step (A-2): Production of N,N'-hexanediyl-bis-carbamic Acid Bis(3-methylbutyl) Ester A solution containing 37.7% by weight of N,N-hexanediyl-bis-carbamic acid bis(3-methylbutyl) ester was obtained by carrying out the same method as step (1-2) of Example 1 with the exception of using 1537 g (7.6 mol) of bis(3-methylbutyl) carbonate obtained in step (A-1), using 232 g (2.0 mol) of hexamethylene diamine, and using 19.3 g of sodium methoxide (25% methanol solution).

Step (A-3): Distillation of Low Boiling Point Component

The solution obtained in step (A-2) was placed in a 10 L volumetric flask equipped with a three-way valve, condenser, distillate collector and thermometer followed by replacing the inside of the flask with nitrogen in a vacuum. The flask was immersed in an oil bath heated to 130° C. Distillation was carried out while gradually reducing the pressure within the apparatus to a final pressure within the apparatus of 0.13 kPa. 1078 g of a distillate were obtained. As a result of analyzing by gas chromatography, the distillate was found to be a solution containing 68.1% by weight of bis(3-methylbutyl) carbonate and 31.5% by weight of 3-methyl-1-butanol. As a result of analyzing by liquid chromatography, the distillation residue obtained in the flask was found to contain 59.8% by weight of N,N'-hexanediyl-bis-carbamic acid bis(3-methylbutyl) ester, and the yield of N,N'-hexanediyl-bis-carbamic acid bis(3-methylbutyl) ester based on hexamethylene diamine was 60.3%. The distillation residue was a liquid at 160° C. After maintaining at 160° C. for 1 day, the concentration of N,N'-hexanediyl-bis-carbamic acid bis(3-methylbutyl) ester in the distillation residue was 32.2% by weight.

Comparative Example 2

Step (B-1): Production of N,N'-hexanediyl-bis-carbamic Acid Dimethyl Ester

A solution containing 34.1% by weight of N,N-hexanediyl-bis-carbamic acid dimethyl ester was obtained by carrying out the same method as step (1-2) of Example 1 with the exception of using 1625 g (18.0 mol) of dimethyl carbonate instead of bis(3-methylbutyl) carbonate, using 349 g (3.0 mol) of hexamethylene diamine, and using 28.9 g of sodium methoxide (25% methanol solution).

Step (B-2): Distillation of Low Boiling Point Component 3972 g of a distillate were obtained by carrying out the same method as step (1-3) of Example 1 with the exception of using the solution obtained in step (B-1) and 2702 g of toluene (Wako Pure Chemical Industries, Ltd., Japan) instead of 2,4-di-tert-amylphenol. As a result of analyzing by gas chromatography, the distillate was found to contain 27.5% by weight of dimethyl carbonate, 4.7% by weight of methanol and 67.7% by weight of toluene. As a result of analyzing by liquid chromatography, the distillation residue obtained in the flask was found to contain 67.3% by weight of N,N'-hexanediyl-bis-carbamic acid dimethyl ester, and the yield of N,N'-hexanediyl-bis-carbamic acid dimethyl ester based on hexamethylene diamine was 70.5%. The distillation residue was a liquid at 50° C. After maintaining at 50° C. for 10 days, the concentration of N,N'-hexanediyl-bis-carbamic acid dimethyl ester in the distillation residue was 31.6% by weight.

Comparative Example 3

Step (C-1): Production of Dibutyl Carbonate

Dibutyl carbonate was produced using the same method as step (7-1) of Example 7.

Step (C-2): Production of N,N'-hexanediyl-bis-carbamic Acid Dibutyl Ester

A solution containing 27.4% by weight of N,N-hexanediyl-bis-carbamic acid dibutyl ester was obtained by carrying out the same method as step (1-2) of Example 1 with the exception of using 2324 g (13.3 mol) of dibutyl carbonate produced in step (C-1) instead of bis(3-methylbutyl) carbonate, using 267 g (2.3 mol) of hexamethylene diamine, and using 13.3 g of sodium methoxide (25% methanol solution).

Step (C-3): Preparation of Composition 1901 g of a distillate were obtained by carrying out the same method as step (1-3) of Example 1 with the exception of using the solution obtained in step (C-1) and 2850 g of benzylbutyl phthalic acid (Wako Pure Chemical Industries, Ltd., Japan) instead of 2,4-di-tert-amylphenol. As a result of analyzing by gas chromatography, the distillate was found to contain 78.4% by weight of dibutyl carbonate and 16.8% by weight of 1-butanol. In addition, as a result of analyzing by liquid chromatography, the distillation residue obtained in the flask was found to contain 14.9% by weight of N,N'-hexanediyl-bis-carbamic acid dibutyl ester, and the yield of N,N'-hexanediyl-bis-carbamic acid dibutyl ester based on hexamethylene diamine was 71.3%. The distillation residue was a liquid at 70° C. After maintaining at 70° C. for 1 day, the concentration of N,N'-hexanediyl-bis-carbamic acid dibutyl ester in the distillation residue was 8.6% by weight.

Comparative Example 4

Step (D-1): Production of Bis(3-methylbutyl) Carbonate

Bis(3-methylbutyl) carbonate was produced using the same method as step (1-1) of Example 1.

Step (D-2): Production of N,N'-hexanediyl-bis-carbamic Acid Bis(3-methylbutyl) Ester A solution containing 29.4% by weight of N,N-hexanediyl-bis-carbamic acid bis(3-methylbutyl) ester was obtained by carrying out the same method as step (1-2) of Example 1 with the exception of using 1922 g (9.5 mol) of bis(3-methylbutyl) carbonate obtained in step (D-1), using 221 g (1.9 mol) of hexamethylene diamine, and using 18.3 g of sodium methoxide (25% methanol solution).

Step (D-3): Preparation of Composition 4190 g of a distillate were obtained by carrying out the same method as step (1-3) of Example 1 with the exception of using the solution obtained in step (D-2) and 3117 g of 2,6-dimethylphenol instead of 2,4-di-tert-amylphenol. As a result of analyzing by gas chromatography, the distillate was found to contain 27.8% by weight of bis(3-methylbutyl) carbonate, 8.1% by weight of 3-methyl-1-butanol and 64.4% by weight of 2,6-dimethylphenol. In addition, as a result of analyzing by liquid chromatography, the distillation residue obtained in the flask was found to contain 80.7% by weight of N,N'-hexanediyl-bis-carbamic acid bis(3-methylbutyl) ester, and the yield of N,N'-hexanediyl-bis-carbamic acid bis(3-methylbutyl) ester based on hexamethylene diamine was 85.1%. The distillation residue was a liquid at 150° C. After maintaining at 150° C. for 1 day, the concentration of N,N'-hexanediyl-bis-carbamic acid bis(3-methylbutyl) ester in the distillation residue was 42.1% by weight.

INDUSTRIAL APPLICABILITY

The composition according to the present invention is able to inhibit a thermal denaturation reaction of carbamic acid ester. In addition, since isocyanate production process using this composition enables isocyanates to be efficiently produced without using highly toxic phosgene, the composition according to the present invention and the isocyanate production process using this composition are highly useful industrially and have high commercial value.

BRIEF DESCRIPTION OF REFERENCE NUMERALS

Figure 1:
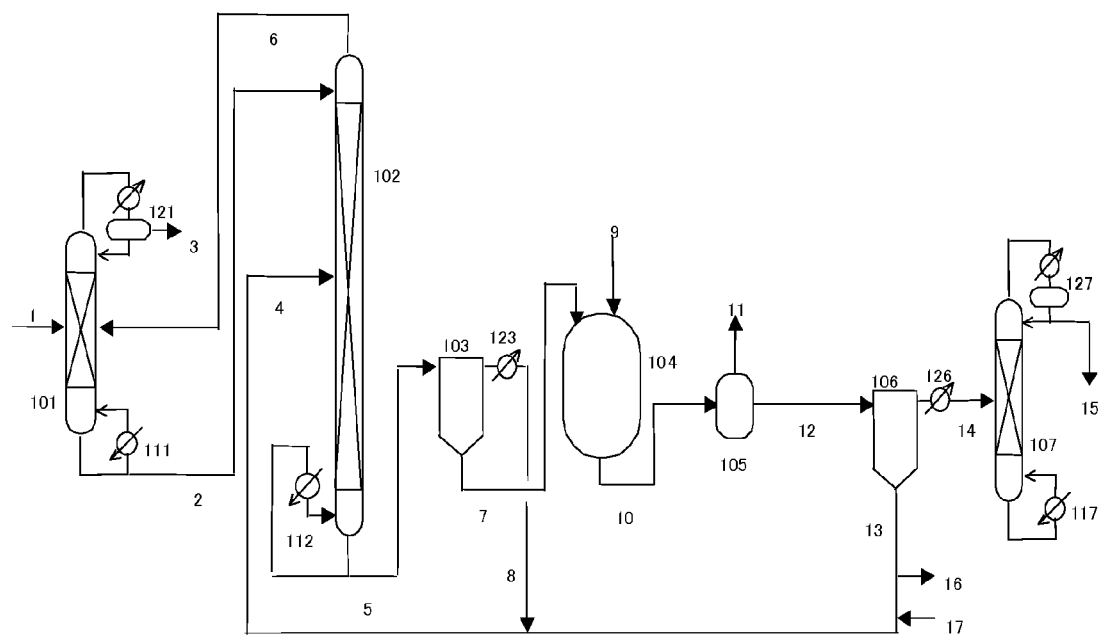
FIG. 1 illustrates a schematic drawing showing a continuous production apparatus for producing carbonic acid ester used in an embodiment of the present invention.

In FIG. 1

Figure 2:
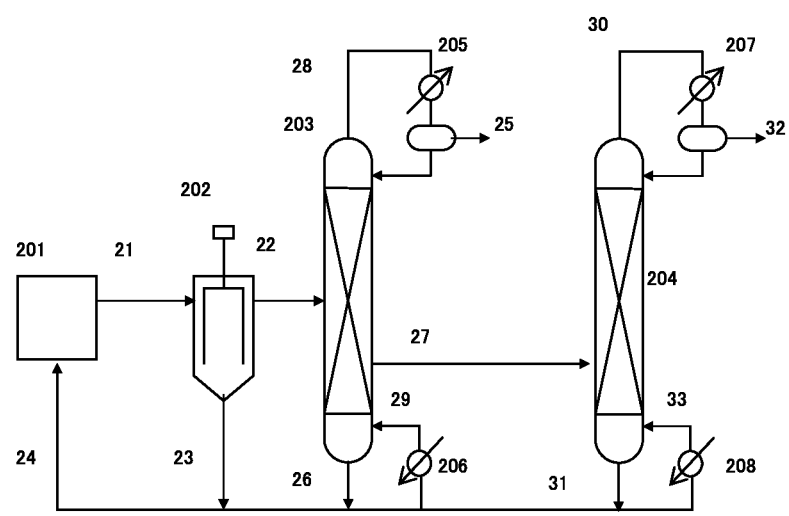
FIG. 2 illustrates a schematic drawing showing an isocyanate production apparatus used in an embodiment of the present invention.

101, 107: distillation column, 102: column-type reaction vessel, 103, 106: thin film distillation apparatus, 104: autoclave, 105: decarbonization tank, 111, 112, 117: reboiler, 121, 123, 126, 127: condenser, 1, 9: feed line, 2, 4, 5, 6, 7, 8, 10, 11, 12, 13, 14: transfer line, 3, 15: recovery line, 16: extraction line, 17: feed line, In FIG. 2

Figure 3:
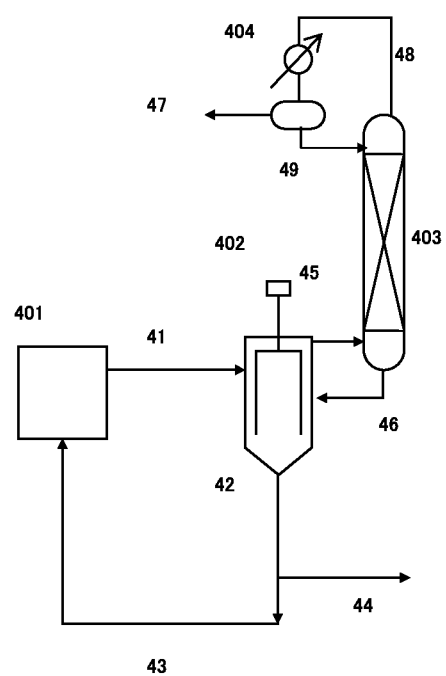
FIG. 3 illustrates a schematic drawing showing a transesterification reaction apparatus used in an embodiment of the present invention.

201: tank, 202: thin film distillation apparatus, 203, 204: distillation column, 205, 207: condenser, 206, 208: reboiler, 21, 22, 23, 24, 25, 26, 27, 28, 29, 30, 31, 32, 33: transfer line, In FIG. 3

Figure 4:
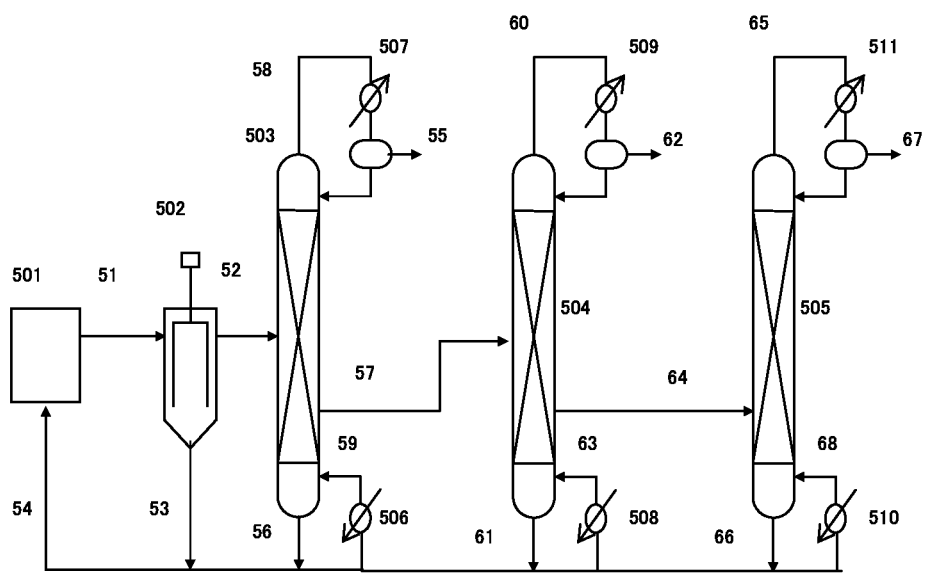
FIG. 4 illustrates a schematic drawing showing an isocyanate production apparatus used in an embodiment of the present invention.

401: tank, 402: thin film distillation apparatus, 403: distillation column, 404: condenser, 41, 42, 43, 44, 45, 46, 47, 48, 49: transfer line In FIG. 4

Figure 5:
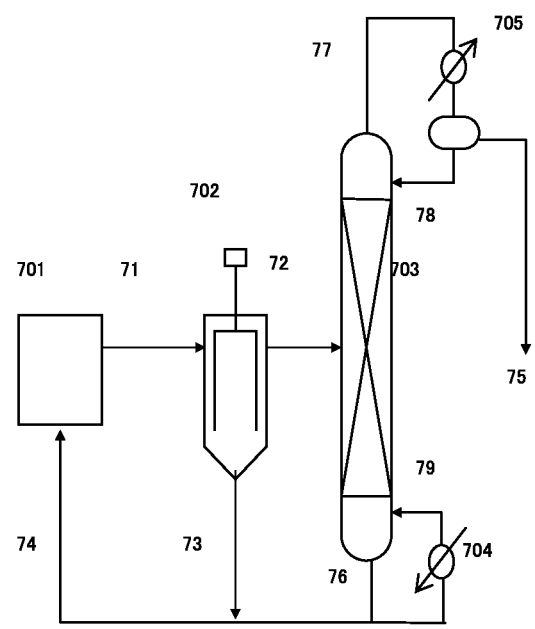
FIG. 5 illustrates a schematic drawing showing an isocyanate production apparatus used in an embodiment of the present invention.

501: tank, 502: thin film distillation apparatus, 503, 504, 505: distillation column, 507, 509, 511: condenser, 506, 508, 510: reboiler, 51, 52, 53, 54, 55, 56, 57, 58, 59, 60, 61, 62, 63, 64, 65, 66, 67, 68: transfer line In FIG. 5

Figure 6:
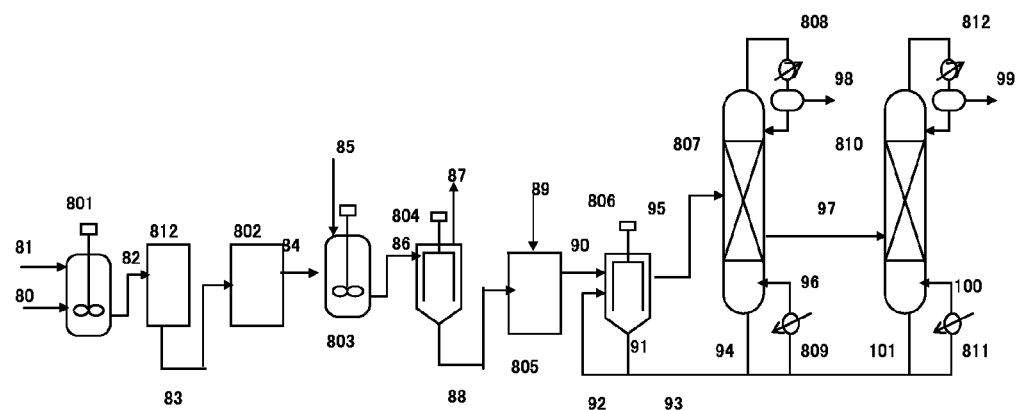
FIG. 6 illustrates a schematic drawing showing a continuous isocyanate production apparatus used in an embodiment of the present invention.

701: tank, 702: thin film distillation apparatus, 703: distillation column, 704: reboiler, 705: condenser, 71, 72, 73, 74, 75, 76, 77, 78, 79: transfer line In FIG. 6

Figure 7:
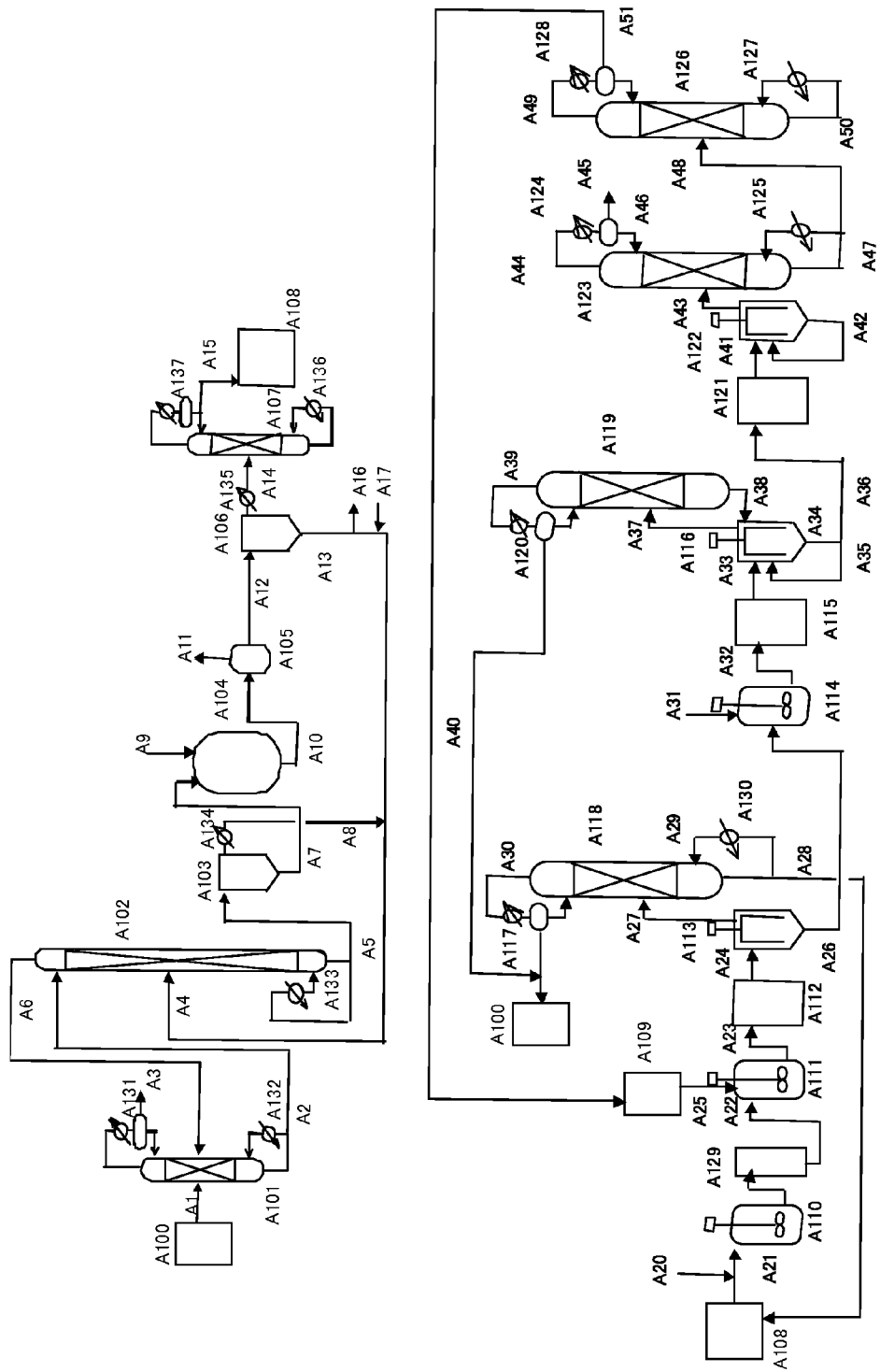
FIG. 7 illustrates a schematic drawing showing a continuous isocyanate production apparatus used in an embodiment of the present invention.
Figure 8:
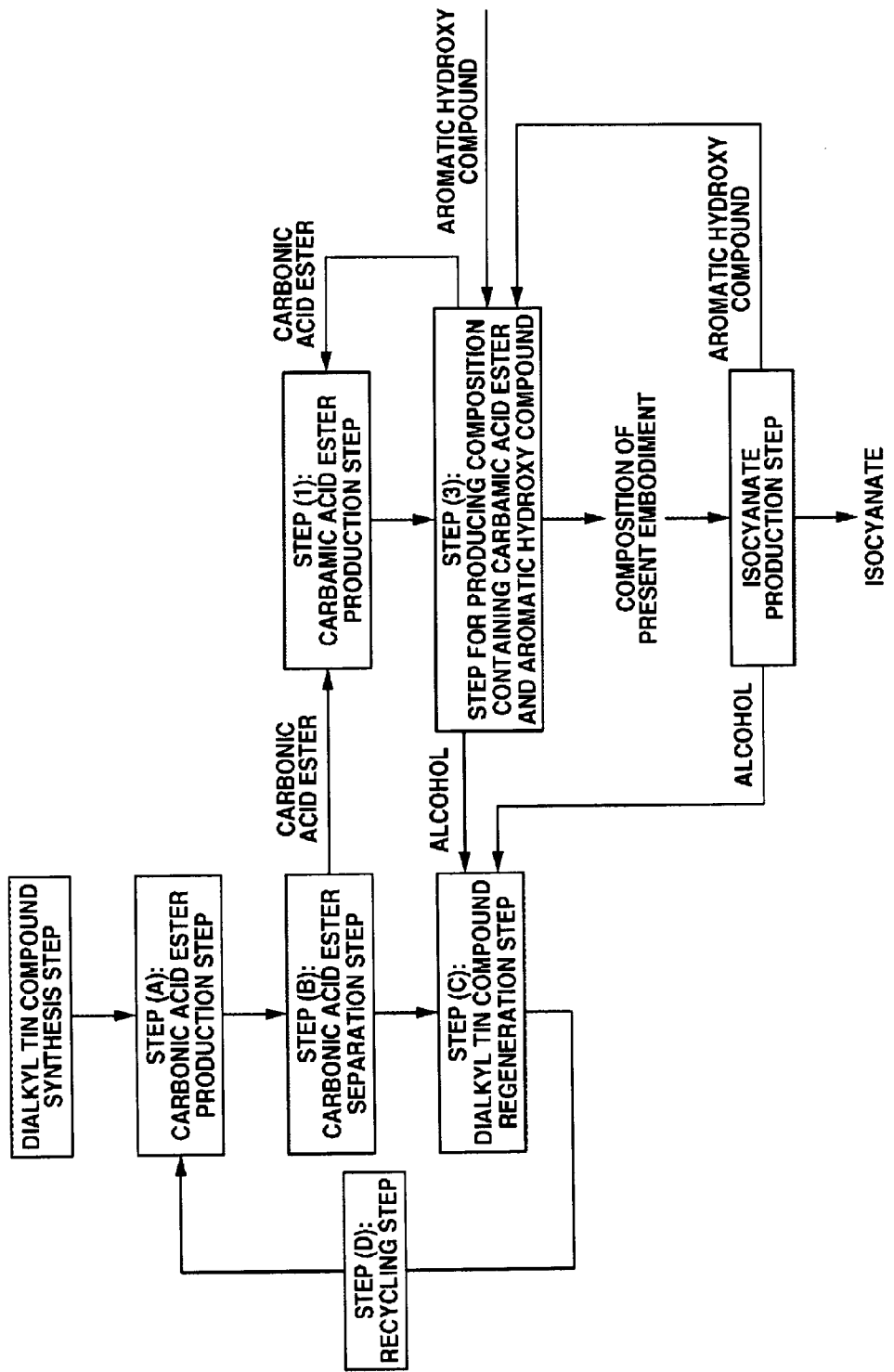
FIG. 8 illustrates the process flow of an example of a modified process for producing isocyanate according to an embodiment of the present invention.

801, 803: stirring tank, 812: ion exchange resin column, 802, 805: tank, 804, 806: thin film distillation apparatus, 807, 810: distillation column, 808, 812: condenser, 809, 811: reboiler, 80, 81, 82, 83, 84, 85, 86, 87, 88, 89, 90, 91, 92, 93, 94, 95, 96, 97, 98, 99, 100, 101: transfer line In FIG. 7

A100, A108, A019, A112, A115, A121: tank, A101, A107, A118, A119, A123, A126: distillation column, A102: column-type reaction vessel, A103, A016, A113, A116, A122: thin film distillation apparatus, A104: autoclave, A105: decarbonization tank, A110, A111, A114, stirring tank, A129: ion exchange resin column, A132, A133, A136, A130, A125, A127: reboiler, A131, A137, A134, A135, A117, A120, A124, A128: condenser, A1, A2, A3, A4, A5, A6, A7, A8, A9, A10, A11, A12, A13, A14, A15, A16, A17, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51: transfer line

We claim:

1. A composition for transfer and storage of a carbamic acid ester comprising:
    a carbamic acid ester; and
    an aromatic hydroxy compound,
wherein:
    when the number of moles of an ester group constituting the carbamic acid ester is defined as A, and the number of moles of the aromatic hydroxy compound is defined as B, then a ratio of B to A is within a range of from 0.1 to 50,
    a melting point of the carbamic acid ester is 200° C. or lower, and
    a melting point of the aromatic hydroxy compound is 190° C. or lower,
wherein the carbamic acid ester is a compound represented by formula (17):

(17)

where $R^7$ is an aliphatic group having 1 to 20 carbon atoms and containing atoms selected from carbon atoms and oxygen atoms;
    $R^{11}$ is an aliphatic group having 1 to 10 carbon atoms or an aromatic group having 6 to 20 carbon atoms, where the aliphatic group and the aromatic group contain atoms selected from carbon atoms and oxygen atoms; and
    n is an integer from 2 to 10.

* * * * *